US012607589B2

(12) United States Patent
Grinstaff et al.

(10) Patent No.: US 12,607,589 B2
(45) Date of Patent: Apr. 21, 2026

(54) METHODS, ASSAYS AND SYSTEMS FOR DETECTION OF A TARGET ANALYTE

(71) Applicant: Sorrento Therapeutics, Inc., San Diego, CA (US)

(72) Inventors: Mark William Grinstaff, Brookline, MA (US); Scott Edward Schaus, Boston, MA (US); Jane P. Bearinger, Berwyn, PA (US); Augustus Lang, Jamaica Plains, MA (US); Ziad Al-Shamsie, San Diego, CA (US); Dylann Ceriani, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 158 days.

(21) Appl. No.: 18/261,325

(22) PCT Filed: Jan. 13, 2022

(86) PCT No.: PCT/US2022/012370
§ 371 (c)(1),
(2) Date: Jul. 13, 2023

(87) PCT Pub. No.: WO2022/155380
PCT Pub. Date: Jul. 21, 2022

(65) Prior Publication Data
US 2024/0302317 A1 Sep. 12, 2024

Related U.S. Application Data

(60) Provisional application No. 63/137,085, filed on Jan. 13, 2021, provisional application No. 63/150,990, (Continued)

(51) Int. Cl.
*G01N 27/327* (2006.01)
*C12Q 1/00* (2006.01)
(Continued)

(52) U.S. Cl.
CPC ......... *G01N 27/3275* (2013.01); *C12Q 1/005* (2013.01); *G01N 27/3271* (2013.01); (Continued)

(58) Field of Classification Search
None
See application file for complete search history.

(56) References Cited

U.S. PATENT DOCUMENTS

| | | | |
|---|---|---|---|
| 2003/0082601 A1* | 5/2003 | Dill | .................... G01N 33/5438 435/7.5 |
| 2006/0211061 A1 | 9/2006 | Haik | |
| 2024/0011990 A1* | 1/2024 | Sankar | ............. G01N 33/54386 |

FOREIGN PATENT DOCUMENTS

| | | |
|---|---|---|
| WO | WO 03/019147 | 3/2003 |
| WO | WO 2008/045799 | 4/2008 |

OTHER PUBLICATIONS

Z.P. Aguilar, et al., "Self-contained microelectrochemical immunoassay for small volumes using mouse IgG as a model system", Analytical Chemistry, 74(14): p. 3321-3329, Jul. 2022.*
(Continued)

*Primary Examiner* — J. Christopher Ball
(74) *Attorney, Agent, or Firm* — King & Spalding LLP

(57) ABSTRACT

The strip systems, methods, devices and associated kits disclosed herein are used to determine the presence and/or level a target analyte(s) in sample (e.g., a biological sample such as saliva or nasal swab) wherein the target analyte(s) may be a microorganism (e.g., a whole virus) or molecule (e.g., a viral antigen) associated with a healthy state, disease or injury or otherwise altered physiological condition. In certain embodiments, the systems, methods, devices and kits provide one or more improved properties relative to the lateral flow protein and other assays known in the art for the detection, including but not limited to, assay time, ease of use, risk of infection, accuracy, specificity, selectivity, limit
(Continued)

Qualitative or Quantitative Sensing Embodiment ~ ELECTROCHEMICAL DETECTION
F1= diluted sample with target in buffer of detection of the assay, quantitative detection and the effect of common interferents to the sensor output, cost, simplicity or a combination thereof. In certain embodiments, the systems, assays, methods and kids are multiplexed, i.e., permit detection or monitoring of more than one target analyte (e.g., two different viruses or a virus and a bacterium).

19 Claims, 61 Drawing Sheets

Related U.S. Application Data filed on Feb. 18, 2021, provisional application No. 63/156,666, filed on Mar. 4, 2021, provisional application No. 63/156,663, filed on Mar. 4, 2021, provisional application No. 63/170,426, filed on Apr. 2, 2021, provisional application No. 63/208,694, filed on Jun. 9, 2021, provisional application No. 63/221,375, filed on Jul. 13, 2021, provisional application No. 63/271,544, filed on Oct. 25, 2021, provisional application No. 63/272,065, filed on Oct. 26, 2021.

(51) Int. Cl.
| | | |
|---|---|---|
| *G01N 33/569* | (2006.01) | |
| *G01N 33/68* | (2006.01) | |
| *G01N 33/74* | (2006.01) | |

(52) U.S. Cl.
CPC ... *G01N 33/56983* (2013.01); *G01N 33/6869* (2013.01); *G01N 33/74* (2013.01); *G01N 2333/165* (2013.01); *G01N 2333/5412* (2013.01); *G01N 2333/5756* (2013.01); *G01N 2469/10* (2013.01)

(56) References Cited

OTHER PUBLICATIONS

D. Ogasawara, et al., "Electrochemical microdevice with separable electrode and antibody chips for simultaneous detection of pepsinogens 1 and 2", Biosensors & Bioelectronics, 21(9): p. 1784-1790, Mar. 2006.*
International Search Report for PCT/US2022/012370, issued May 4, 2022.
Cho, I.-H. et al., "Current technologies of electrochemical immunosensors : perspective on signal amplification", Sensors, 2018, vol. 17, Article No. 207(pp. 1-18).
Mansuriya, B. D. et al., "Graphene quantum dot-based electrochemical immunosensors for biomedical applications", Materials, Published online: Dec. 23, 2019, vol. 13, Article No. 96 (pp. 1-30).

* cited by examiner

Qualitative or Quantitative Sensing Embodiment – ELECTROCHEMICAL DETECTION
F1= diluted sample with target
in buffer Schematics of detection cartridge which affords sample insertion at proximal end, mixing channels for reagents, glucose pod chamber and waste chamber.

electrochemical detection reader

Strip may include sample prep components 80, such as diluters, filters to remove unwanted materials or inhibitors, sample integrators, intensifiers, mixers, etc. These may involve blister packs, pods, caps, reagents, molded or cut/ etched features, etc. Positioning may be proximal, distal, or elsewhere appropriate. Materials may create flow paths, microfluidic channels, mixing, split flow channels that may incorporate different reagents (F1, F2, etc.) Alternatively, separate sample prep components may be used

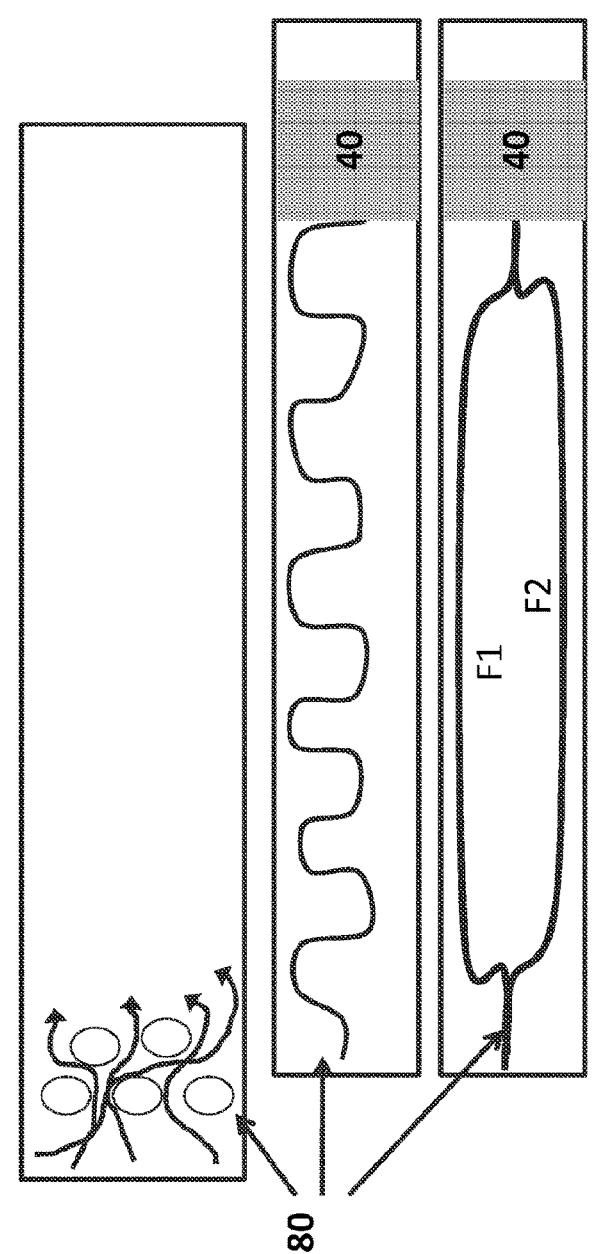

80

40

40

F1

F2

Different materials may be used or wells may be created to increase residence time of reagents on immobilization pad.

Blister packs or pods may be incorporated to add secondary flow solution (F2₁, F2₂, etc.)

Various electrode configurations may be utilized with the strip

Figure 5

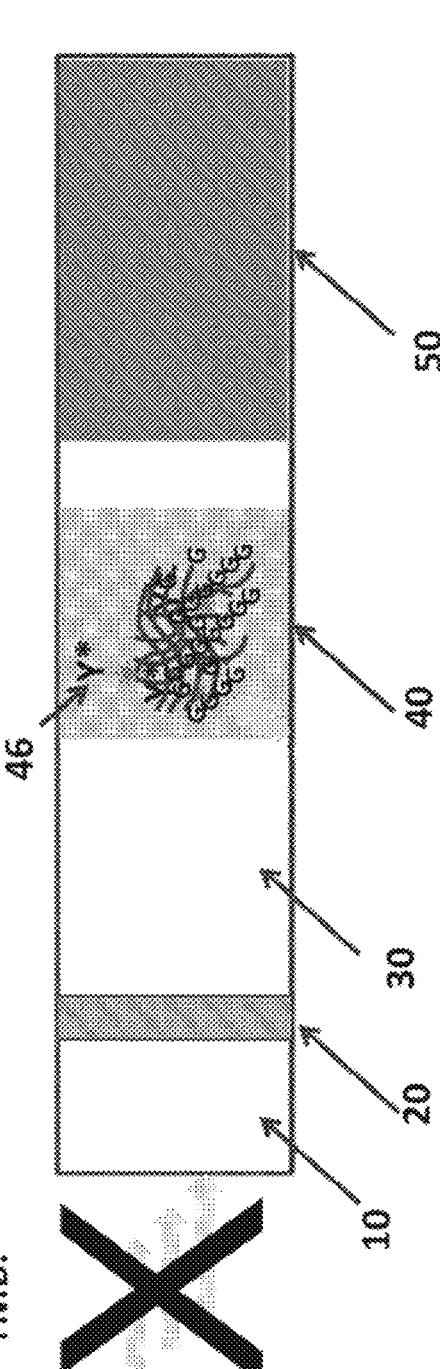

A gel, such as a loosely crosslinked hydrogel saturated with glucose, may be used to facilitate $H_2O_2$ generation and current production on top of a working electrode and immobilization pad construct that includes immobilized target linked to GOx. Placement of such a gel would preclude $F2_1/F2_2/$etc. and would aid to retain glucose in desired area of interest for chemical measurement. Gel components may enable reactions, accelerate reactions, stabilize reactions, etc. For example, gel components may include HRP and TMB.

Remove flow step and enable H2O2 production via gel in proximity of bound target/ GOx

Figure 9 designs may include different materials for sample pad, conjugate pad, absorptive pad, etc.

Cap
contains
buffer

Foam collects sample – when cap
closes down on foam, Diluted
sample is released into fluidic
pathway

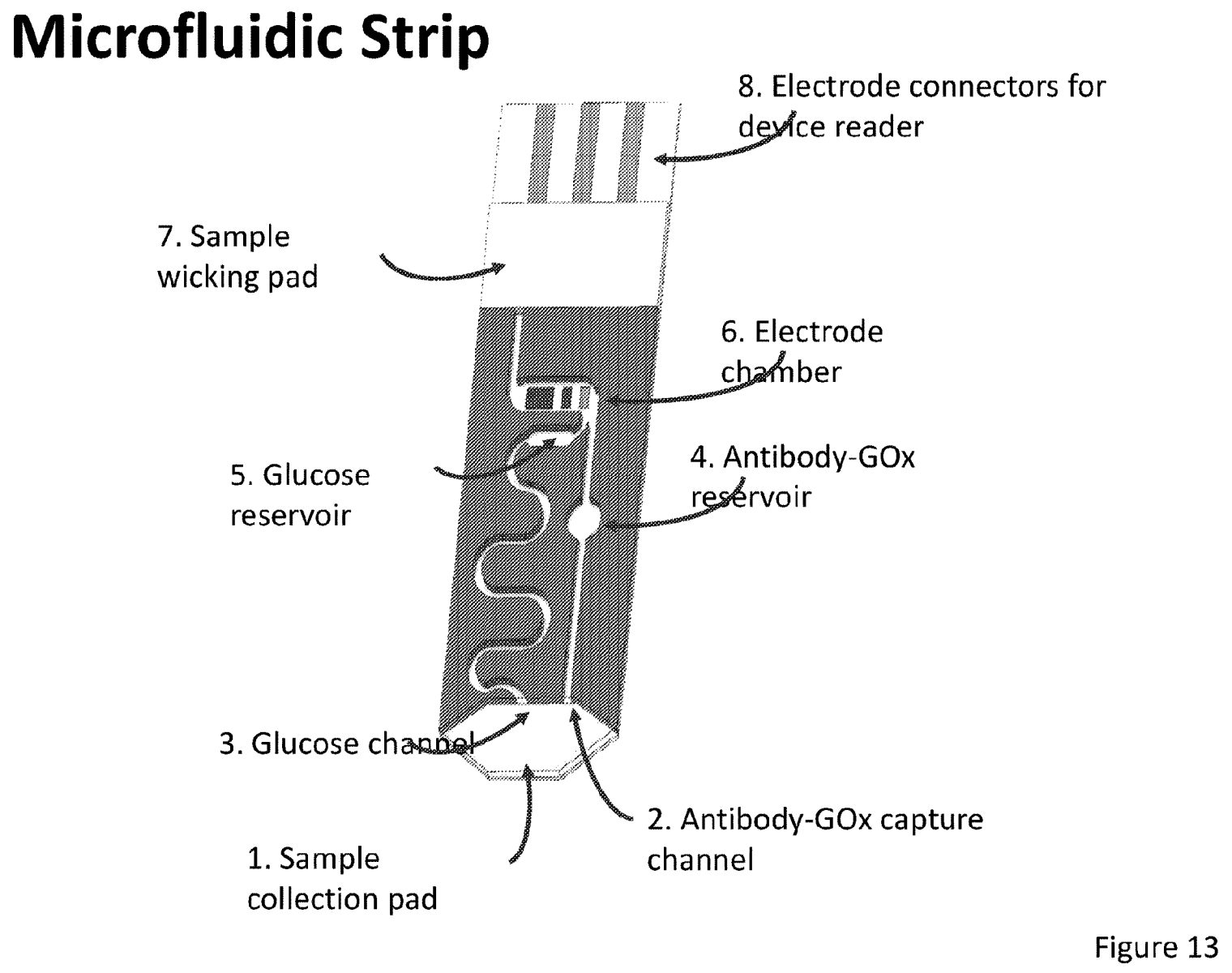

Microfluidic Strip

8. Electrode connectors for device reader

6. Electrode chamber

4. Antibody-GOx reservoir

2. Antibody-GOx capture channel

7. Sample wicking pad

5. Glucose reservoir

3. Glucose channel

1. Sample collection pad

Figure 13

Exemplary electrochemical detection of H1N1
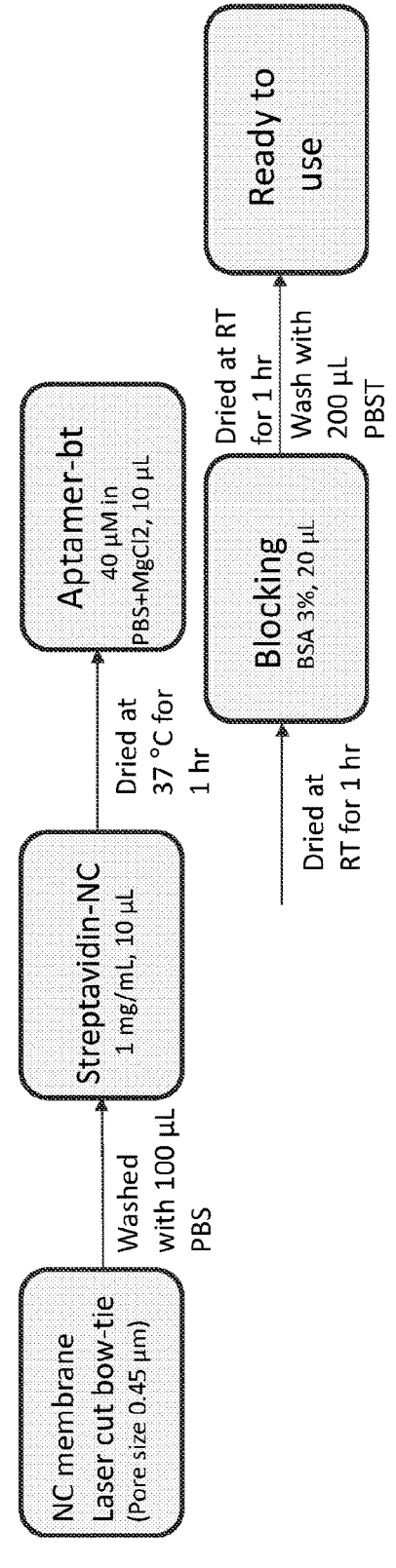
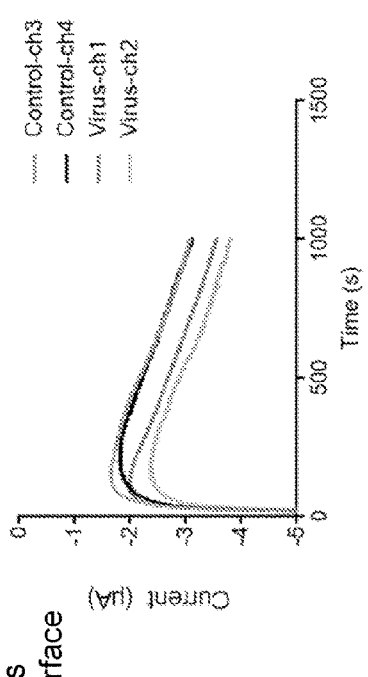
Nitrocellulose membrane
- 0.45 um pores (ideal for proteins > 20 kDa)
- Thickness ~130 um
1) Bow-tie with streptavidin+aptamer
2) Mix Antibody-Gox and virus
3) Add them to the sensor surface
4) Incubate for 3 min
5) Pipette out the sample
6) Add glucose and measure
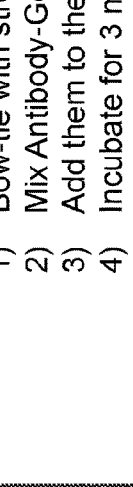
3 electrode system with
Strip chemistry on top of
Working electrode
Figure 14

Different [virus] of CoV-2 in buffer

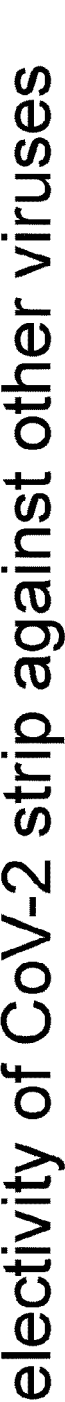
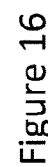
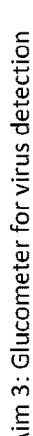
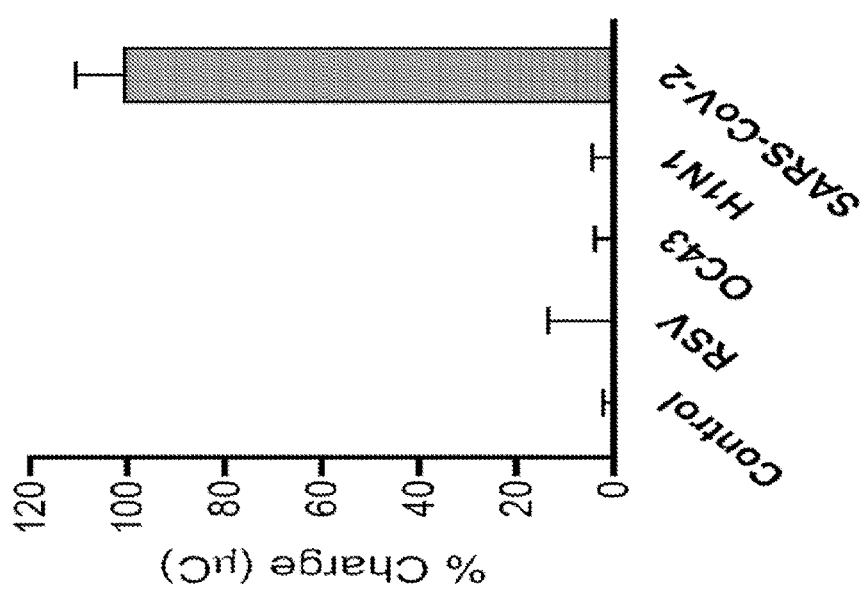
Selectivity of CoV-2 strip against other viruses
- Control: No virus
- OC43: Human Coronavirus
- RSV: causes common Cold
Figure 16
Aim 3: Glucometer for virus detection

H1N1
- 0.03 mg/mL HRP + 1mM TMB + 2% DMSO+ 500 mM glucose
- 30 uL of Virus + Ab-Gox (0.1 mg/mL) incubated for 5 mir
- Pipetted off and the dye+glucose solution was added
- 0.03 mg/mL HRP + 10mM TMB + 20% DMSO+ 500 mM glucose
- 30 uL of Virus (10^5) + Ab-Gox (0.1 mg/mL) incubated for 5 min
- Pipetted off and the dye+glucose solution was added
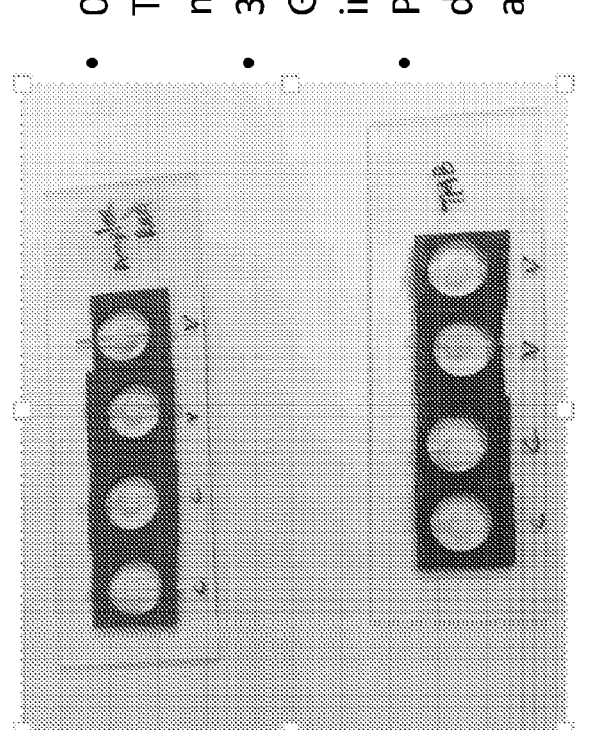
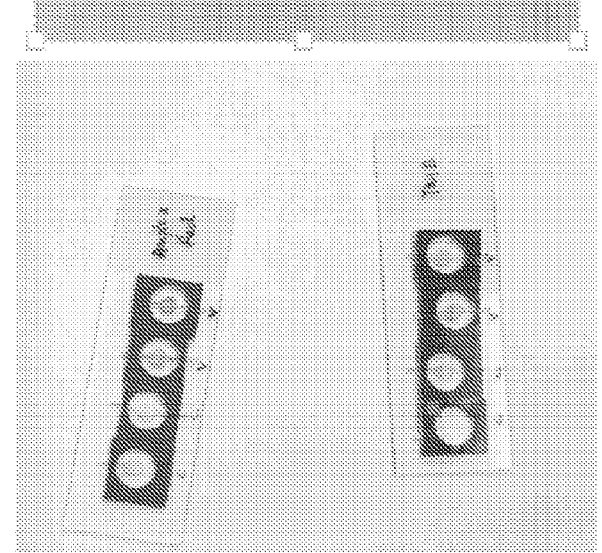
Figure 18

OPN
3/23/2021 OPN
Dye Solution: TMB (0.2 mM), HRP (1 µg/mL), glucose (0.5 M) Citrate (pH 5.5)    1 min
0 ng/mL                    375 ng/mL
Dye Solution: TMB (0.2 mM), Ab-HRP (2 µg/mL), glucose (0.5 M) Citrate (pH 5.5)    1 min
0 ng/mL                    375 ng/mL
Strip = NC/Ab1 (ab8448, abcam)/BSA
Sample = 1 µg/mL Ab-GOx (ab69498, abcam) in PBS +/- OPN (ab92964)
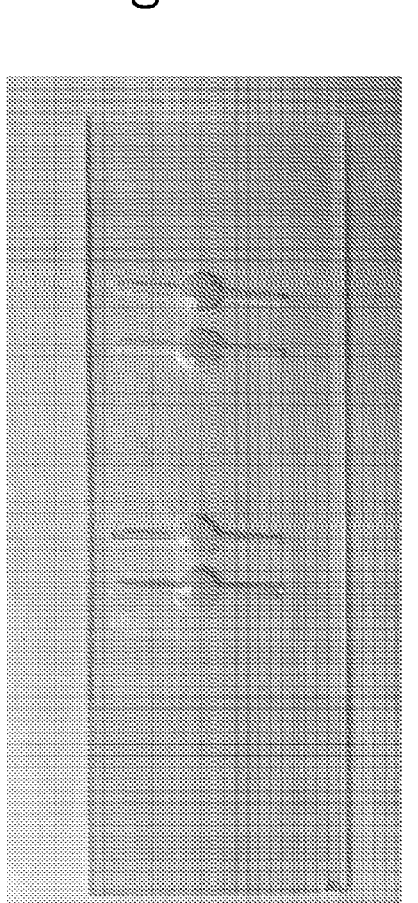
OPN 10x
Figure 19

OPN Detection
Strip = NC/Ab1 (ab8448, abcam)/BSA
Sample = 1 µg/mL Ab-GOx (ab69498, abcam) in PBS +/- OPN (ab92964)
Dye solution = TMB (1mM), HRP (10 µg/mL), glucose (0.5 M), citrate buffer (2% DMSO final)
1 min
2 min
3750
0
OPN (ng/mL)
*3/25/21 (9:55 pm)*
Strip = NC/Ab1 (ab8448, abcam)/BSA
Sample = 1 µg/mL Ab-GOx (ab69498, abcam), 0.2% BSA in PBS +/- OPN (ab92964)
Dye solution = TMB (1mM), HRP (10 µg/mL), glucose (0.5 M), 0.2 % BSA, citrate buffer (2% DMSO final)
1 min
2 min
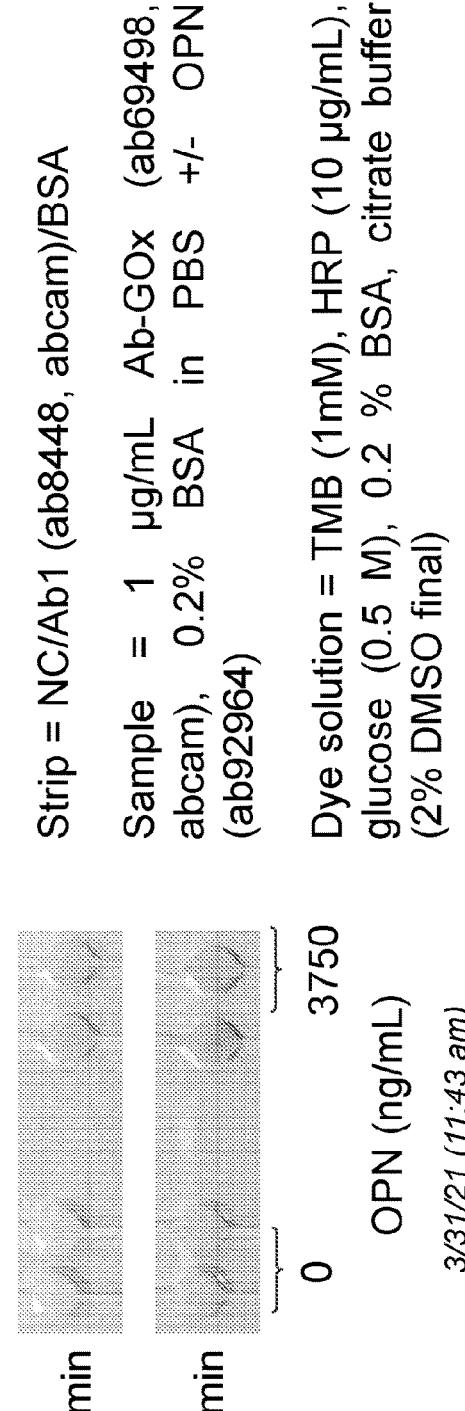
3750
0
OPN (ng/mL)
*3/31/21 (11:43 am)*
Figure 20

Electrochemical 'bowtie' prototype configuration presently used by Virex

Optical 'bowtie' prototype configuration by Virex

Sample + reagents are added to immobilization region disposable test

Waterproof barrier

Immobilization region
Which may comprise waterproof base

Optical 'bowtie' prototype configuration by Virex

Immobilization pad

Waterproof barrier

Chamber lies within waterproof barrier
And comprises waterproof base

Immobilization pad

General binding sites, in this case: streptavidin

General binding sites, in this case: Streptavidin labeled beads

Generic binding construct, such as streptavidin, may be in the form of lines, entire region, gradients, patterns, topographies, etc. that may assist in quantification of target Lateral flow device cartridge
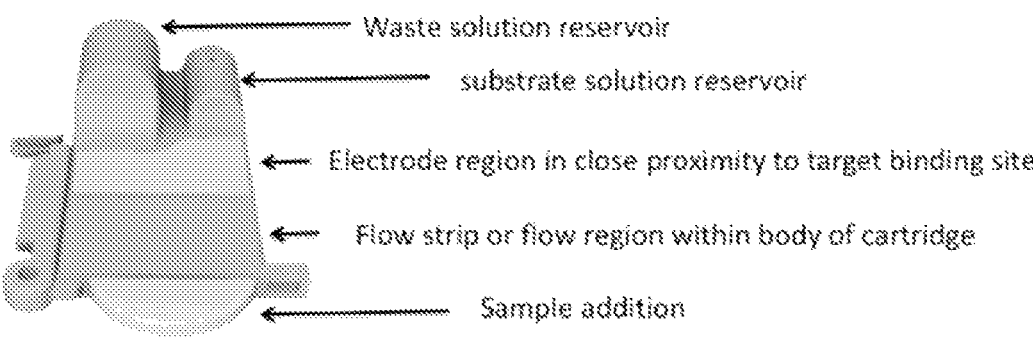
Waste solution reservoir
substrate solution reservoir
Electrode region in close proximity to target binding site
Flow strip or flow region within body of cartridge
Sample addition
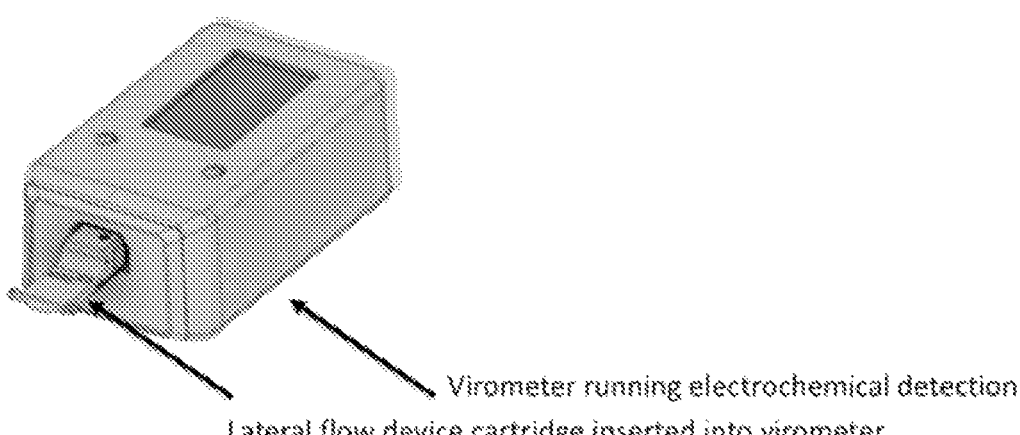
Virometer running electrochemical detection
Lateral flow device cartridge inserted into virometer
Figure 39

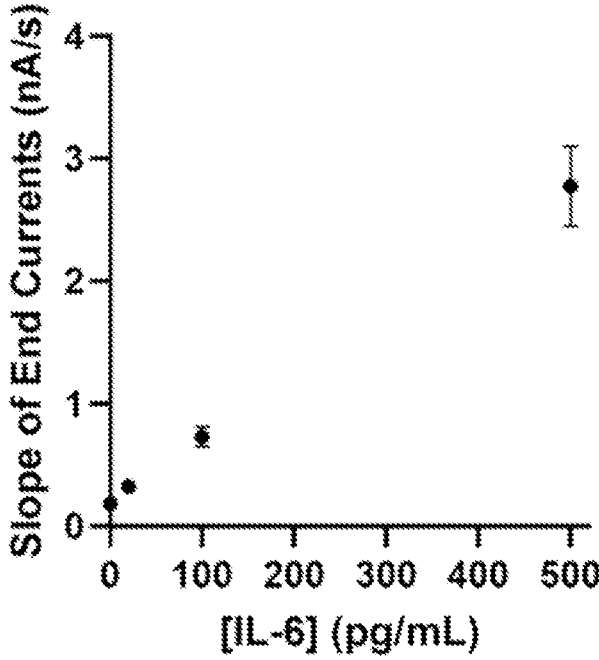
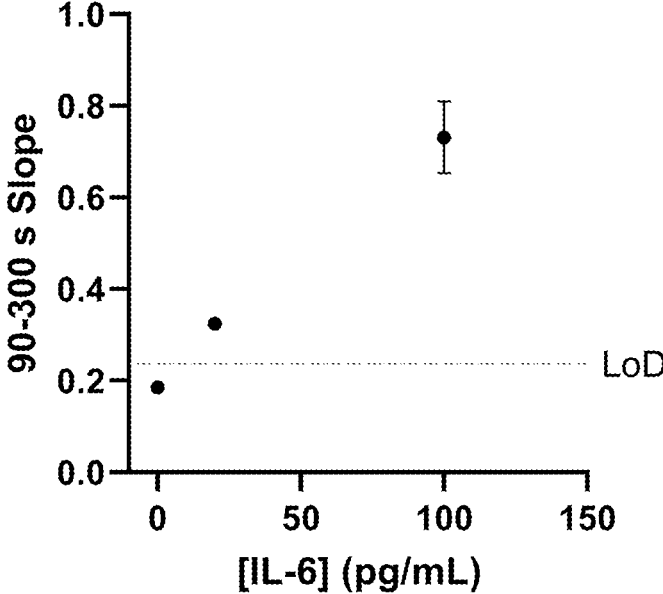
Figure 45

1

METHODS, ASSAYS AND SYSTEMS FOR DETECTION OF A TARGET ANALYTE

CROSS REFERENCE TO RELATED APPLICATIONS

This application is a national phase application under 35 U.S.C. § 371 of International Application No. PCT/US2022/012370, filed Jan. 13, 2022, which claims priority to U.S. Provisional Application No. 63/137,085, filed Jan. 13, 2021; U.S. Provisional Application No. 63/150,990, filed Feb. 18, 2021; U.S. Provisional Application No. 63/156,663, filed Mar. 4, 2021; U.S. Provisional Application No. 63/156,666, filed Mar. 4, 2021; U.S. Provisional Application No. 63/170,426, filed Apr. 2, 2021; U.S. Provisional Application No. 63/208,694, filed Jun. 9, 2021; U.S. Provisional Application No. 63/221,375, filed Jul. 13, 2021; U.S. Provisional Application No. 63/271,544, filed Oct. 25, 2021; and U.S. Provisional Application No. 63/272,065, filed Oct. 26, 2021. The contents of the above-referenced documents are incorporated by reference in their entirety.

FIELD OF THE INVENTION

Disclosed herein are systems, assays and methods for detecting and monitoring a target analyte or analytes present in a sample (e.g., a biological or environmental sample). The methods disclosed herein also include methods of detection, sample preparation, treatment and telehealth services. Kits and reagents to carry out the methods are also provided.

BACKGROUND OF THE INVENTION

Assays to quantitatively detect analytes (e.g., infectious agents) in biological samples are routinely used in medicine to diagnosis or follow the progression of a disease or injury or to monitor health. Historically, these assays have been performed in a healthcare or laboratory setting. Similarly, assays to detect analytes in environmental samples are of importance to industries such as transportation and agriculture and typically conducted in laboratory settings. In both cases, such assays typically require multiple steps and expert analysis.

There remains a need to improve the quantity and value of such testing. In particular, there remains a need for such assays to be performed in non-clinical settings (e.g., a home, office or field), by a layperson, simply and economically.

SUMMARY OF THE INVENTION

Disclosed herein are systems, assays (biosensors) and methods for detecting at least one target analyte in sample. Advantageously, the systems, assays and methods disclosed herein are rapid and permit reliable results even when performed by a relatively untrained user such as a layperson. In certain embodiments, the systems, assays and methods disclosed herein can be used to detect low concentrations of at least one target analyte using small sample volumes.

In a first aspect, a system is provided for detecting at least one target analyte in a sample (e.g., a biological or environmental sample) added to the system, comprising: (i) an assay comprising at least one capture agent and at least one detector agent capable of creating a detectable complex with the at least one target analyte, if present, in the presence of substrate (e.g., a substrate added by the user); and (ii) a detection device for detecting the detectable complex, wherein the detection device comprises an enzyme-based amperometric sensor comprising at least one electrode, wherein the detectable complex forms above the least one electrode or migrates within the system to become located above at least one electrode.

The time to result provided by the system vary. In one embodiment, the detectable complex is detected within about 30 minutes or less, about 10 minutes or less, about 5 minutes or less, about 2 minutes or less or about 1 minute or less. In a particular embodiment, the time to result is less than 1 minute or more particularly, about 30 seconds, about 20 seconds, about 10 seconds or about 1 second.

The target analyte detected by the system may vary. In one embodiment, the target analyte is selected from a microorganism (e.g., a virus, bacteria, protozoa, fungi or prion), a protein, a peptide, cytokine, a hormone, a steroid, a cofactor, a small molecule (e.g., a therapeutic drug or drug of abuse), a vitamin or the like.

In one embodiment, the target analyte detected by the system is a viral protein.

In a particular embodiment, the target analyte detected by the system is a nucleocapsid (N) protein of a coronavirus, such as SARS-CoV-2 or variant thereof.

In a particular embodiment, the target analyte is a spike (S) protein of coronavirus, such as SARS-CoV-2 or variant thereof.

In certain embodiments, the system detects more than one target analyte in the biological sample, e.g., two or more viral species. In some embodiments, the one or more viral species are closely related. In certain embodiments, the system detects SARS-CoV-d and influenza.

The limit of detection (LOD) of the system may vary. In one embodiment, the system has a LOD of about 1 mg/mL or less, about 1 ng/mL or less, about 1 pg/mL or less or 1 about fg/mL or less.

In a particular embodiment, the target analyte is a protein or peptide and the system has an LOD of about 500 pg/mL or less, more particularly, about 200, about 150, about 100, about 75, about 50, about 25, about 10, about 5 or about 1 pg/mL or less.

In one embodiment, the target analyte is a whole virus, such as a whole coronavirus. In a particular embodiment, the whole virus is SARS-CoV-2 or a variant thereof.

In one embodiment, the target analyte is a whole virus has an LOD of about 10000 TCID50/mL or less, about 5000 TCID50/mL or less, about 1000 TCID50/mL or less, about 100 TCID50/mL or less, about 50 TCID50/mL or less, about 25 TCID50/mL or less, about 10 TCID50/mL or less, or about 5 TCID50/mL or less.

The capture and detector agents may vary. In certain embodiments, the capture agent and the detector agent are binding agents selected from the group consisting of aptamers, antibodies and proteins or combinations thereof.

The detector agent may be labeled with an enzyme. Any suitable enzyme label may be used, such as an oxidoreductase enzyme. In one embodiment, the enzyme is selected from the group consisting of an oxidase, peroxidase, hydrogenase, catalase, dehydrogenase or phosphatase.

In a particular embodiment, the enzyme label is alkaline phosphatase and the added substrate is selected from the group consisting of pyridoxal-5'-phosphate (PLP), 5-bromo-4-chloro-3-indolyl-phosphate, L-ascorbic acid-2-phosphate, acetaminophen phosphate, 4-acetamidophenyl phosphate, 4-aminophenyl phosphate in diethanolamine (DEA), 1-amino-2-propanol, N-methyl-D-glucamine or tris buffer.

In another particular embodiment the enzyme label is glucose phosphatase and the added substrate is glucose.

In certain embodiments, the system further comprises a reporter agent. The reporter agent may vary, e.g., be selected from an aptamer or antibody. According to this embodiment, the reporter agents binds to the detector agent. Both the detector agent and the reporter agent may be labeled, e.g., with different enzyme labels to provide a dual detection system.

In certain embodiments, the capture agent is present in solution and optionally added by the user prior to binding to the at least one target analyte.

In alternate embodiments, the capture agent is immobilized on a solid or porous support, either directly or by means of a first binding agent, to provide a test site. According to the latter embodiment, the capture agent is conjugated to a second binding agent, wherein the second binding agent binds to the first binding agent.

In one embodiment, the first binding agent is selected from the group consisting of streptavidin, gold, silver, malamides, acrylates, amines, carboxylic acids, vinyl sulfones thiols, silanes and epoxides.

In a particular embodiment, the first binding agent is streptavidin and the second binding agent is biotin.

The binding agents within the assay may be cross-linked to one or more additional binding agents. In one embodiment, the first binding agent is cross-linked to one or more additional first binding agents. In another embodiment, the capture agent is cross-linked to one or more additional capture agents.

In one embodiment, the detector agent is added to the system by the user, optionally together with the capture agent.

The solid or porous support may be any suitable such support, such as a bead, membrane (e.g., a nitrocellulose membrane) or a bead immobilized on a membrane.

In certain embodiments, the assay is housed within a cassette, such as disposable cassette.

In embodiments where the target analyte is a protein, the affinity of the capture agent and the detector agent for the protein may vary. In one embodiment, the capture agent and the detector agent have a Kd of about $10^{10}$ or greater, about $10^{-8}$ Kd or greater or about $10^{-6}$ Kd or greater for the protein.

The accuracy of the system may vary. The system of the disclosed embodiments, wherein the system permits at least about 90% accuracy or more, about 93% accuracy or more, about 95% accuracy or more, about 98% accuracy or more, or about 99% accuracy or more.

In certain embodiments, the system produces an electrochemical signal continuously. In one embodiment, the electrochemical signal is collected discontinuously, for example, the electrochemical signal is collected in intervals separated by waiting periods.

Any suitable assay format may be utilized in the system, including a competitive or non-competitive assay format. In one embodiment, the system comprises a lateral flow assay. In other embodiments, the system comprises a vertical flow assay. The vertical flow assay may have more than one layer, e.g., a multi-layered vertical flow assay.

In some embodiments, the systems described herein are intended for use outside of a clinical setting, e.g., systems for home or workplace use. In some embodiments, the systems are intended for self-monitoring by individuals including over time.

The system may permit qualitative, semi-quantitative or quantitative detection.

In alternate embodiments, the system is an optical system wherein the detection device is an optical reader.

In a particular embodiment, the sample is obtained from two or more subjects.

In a second aspect, an assay is disclosed comprising at least one capture agent and at least on detector agent, wherein the detector agent is labeled with an enzyme label and the capture and detector agents form a detectable complex in the presence of the at least one target analyte and an added substrate.

The assay may be an electrochemical or optical (e.g., fluorescent or colorimetric) assay.

In one embodiment, the detection does not require a detection device. In another embodiment, the detectable complex is detected by a detection device such as, for example, a glucometer, chronoamperometer, or a mobile phone.

The time to result provided by the assay may vary. In one embodiment, detected within about 30 minutes or less, about 10 minutes or less, about 5 minutes or less, about 2 minutes or less or about 1 minute or less. In a particular embodiment, the time to result is less than 1 minute or more particularly, about 30 seconds, about 20 seconds, about 10 seconds or about 1 second.

The target analyte detected by the assay may vary. In one embodiment, the target analyte is a microorganism (e.g., a virus or bacterial), a protein, peptide, hormone, steroid, cytokine, small molecule, co-factor, vitamin or the like.

In one embodiment, the target analyte detected by the assay is a protein or peptide, such as a viral protein or peptide.

In a particular embodiment, the target analyte detected by the assay is a spike (S) protein or nucleocapsid (N) protein of a coronavirus. The coronavirus may be, for example, SARS-CoV-2 or a variant thereof.

In certain embodiments, the assay can detect more than one target analyte either sequentially or simultaneously. For example, the assay can detect two different viral species.

The limit of detection (LOD) of the assay may vary. In one embodiment, the assay has a LOD of about 1 mg/mL or less, about 1 ng/mL or less, about 1 pg/mL or less, or about 1 fg/mL or less.

In a particular embodiment, the target analyte is a protein and the assay has a LOD is about 1 ng/mL or less, about 500 pg/mL or less, more particularly, about 200, about 150, 100, about 75, about 50, about 25, about 10, about 5 or about 1 pg/mL or less.

The number of target analytes the assay may detect can vary. In one embodiment, the assay has a LOD of about 100 target analytes/mL or less, about 50, about 20, about 10, or about 5 target analytes/mL or less.

In certain embodiments, the target analyte is a whole virus such as a whole coronavirus or more particularly, SARS-CoV-2 or a variant thereof.

In one embodiment, the target analyte is a whole virus and the assay has LOD of about 10000 TCID50/mL or less. about 100 TCID50/mL or less, about 50 TCID50/mL or less, about 10 TCID50/mL or less or about 5 TCID50/mL or less.

The capture agent and the detector agent used in the assay may vary. In one embodiment, the capture agent and the detector agent are binding agents selected from the group consisting of aptamers, antibodies and proteins.

The detector agent may be labeled, e.g., with an enzyme label. The enzyme may vary. In one embodiment, the enzyme is an oxidoreductase. In a particular embodiment, the enzyme is selected from the group consisting of an oxidase, peroxidase, hydrogenase, catalase, dehydrogenase or phosphatase.

In one embodiment, the enzyme is alkaline phosphatase and the added substrate is selected from the group consisting of pyridoxal-5'-phosphate (PLP), 5-bromo-4-chloro-3-indo-lyl-phosphate, L-ascorbic acid-2-phosphate, acetaminophen phosphate, 4-acetamidophenyl phosphate, 4-aminophenyl phosphate in diethanolamine (DEA), 1-amino-2-propanol, N-methyl-D-glucamine or tris buffer.

In another embodiment, the enzyme is glucose phosphatase and the added substrate is glucose.

In certain embodiments, the assay further comprises a reporter agent. The reporter agent may vary, e.g., be selected from an aptamer or antibody. According to this embodiment, the reporter agents binds to the detector agent. Both the detector agent and the reporter agent may be labeled, e.g., with different enzyme labels to provide a dual detection system.

In one embodiment, the capture agent is immobilized on a solid or porous support to provide a test site.

In a particular embodiment, the capture agent is immobilized on a solid support by means of a first binding agent. According to this embodiment, the capture agent is conjugated to a second binding agent, wherein the second binding agent binds to the first binding agent. The first binding agent may vary.

In one embodiment, the first binding agent is selected from the group consisting of streptavidin, gold, silver, malamides, acrylates, amines, carboxylic acids, vinyl sulfones thiols, silanes and epoxides.

In a particular embodiment, the first binding agent is streptavidin and the second binding agent is biotin.

The binding agents associated with the assay may be cross-linked. In one embodiment, the first binding agent is cross-linked to one or more additional first binding agents. In another embodiment, the capture agent is cross-linked to one or more additional capture agents.

The solid or porous support may be any suitable such support, such as a bead, membrane (e.g., a nitrocellulose membrane) or a bead immobilized on a membrane.

The solid or porous support may optionally include a control site.

The assay may be optionally housed within a cassette, such as a disposable cassette.

In embodiments where the target analyte is a protein or peptide, the affinity of the capture agent and detector agent for the protein or peptide may vary. In certain embodiments, the capture agent and the detection agent have a Kd of about $10^{-10}$ Kd or smaller, about $10^{-8}$ Kd or smaller or about $10^{-6}$ Kd or smaller for the protein or peptide.

The accuracy of the assay may vary. In one embodiment, the assay is at least about 90%, at least about 93%, at least about 95%, at least about 98% or at least about 99% or more.

The format of the assay may vary. The assay may be a competitive or non-competitive assay. The assay may be a lateral flow or vertical flow assay. In embodiments where assay is a vertical flow assay, the assay may include one or more layers.

In a third aspect, a method for detecting at least one target analyte in a sample (e.g., a biological sample or environmental sample) is provided, comprising (i) providing the sample, (ii) optionally, processing the sample; (iii) adding the sample to the system or assay disclosed herein and (iv) and if the at least one target analyte is present, detecting the target analyte.

The method optionally comprises transmitting the result to a third party for review and optionally, further action.

In one embodiment, the further action comprises diagnosing the presence of a disease state or healthy state. In a particular embodiment, the result may be calibrated against a disease state (e.g., an infection) or a healthy state. The disease may be a viral infection or a bacterial infection. The clinical manifestation may be, for example, an upper respiratory infection, a lower respiratory infection, hepatitis, meningitis, encephalitis, and/or meningoencephalitis, conjunctivitis, keratitis, keratoconjunctivitis, rash or a genital lesion.

In one embodiment, the further action comprises monitoring the results of administration of a therapeutic agent such as a drug to the user. According to this embodiment, the user is a patient or clinical trial subject.

In one embodiment, the action comprises administering or discontinuing the administration of a therapeutic agent to the user.

In a particular embodiment, the further action may include adjusting the dose (upward, downward) of a therapeutic agent previously administered to the user to provide a new dose for administration.

In another particular embodiment, the further action may involve administering an additional (e.g., second) therapeutic agent to the user.

In one embodiment, the approved therapeutic agent is a small molecule drug or a biologic (e.g., a monoclonal antibody, therapeutic vaccine or anticancer agent).

In a particular embodiment, the approved therapeutic agent is a small molecule anti-viral agent. Representative, non-limiting antiviral agents include attachment inhibitors, entry inhibitors, uncoating inhibitors, protease inhibitors, polymerase inhibitors, nucleoside and nucleotide reverse transcriptase inhibitors, nonnucleoside reverse-transcriptase inhibitors, and integrase inhibitors.

In a particular embodiment, the anti-viral agent is selected from acyclovir, gancidovir, foscarnet; ribavirin; amantadine, azidodeoxythymidine/zidovudine), nevirapine, tetrahydro-imidazobenzodiazepinone (TIBO) compound; efavirenz; remdecivir, delavirdine, molnupiravir, nirmatrelvir and ritonavir-boosted nirmatrelvir.

In one embodiment, the small molecule anti-viral agent is remdesivir (as a 200-mg loading dose on day 1, followed by a 100-mg maintenance dose administered daily for up to ten days).

In one embodiment, the approved therapeutic agent is a biologic anti-viral agent. Representative, non-limiting biologic anti-viral agents include monoclonal antibodies (mAbs), nucleic acid therapies (e.g., RNAi, antisense, DNA vaccine, micro RNA, shRNA or aptamer).

In one embodiment, the therapeutic agent is a viral particle blocker.

In one embodiment, the monoclonal antibody anti-viral agent is selected from sotrovimab (e.g., administered as a 500 milligram single dose intravenously), bamlanivimab (700 mg as a single IV infusion), etesevimab and bamlanivimab (1400 mg p estevimab plus bamlanivimab 700 mg as a single IV infusion), or casirivimab and imdevimab (1,200 mg of casirivimab and 1,200 mg of imdevimab in a single IV infusion).

In a particular embodiment, the therapeutic agent is an anti-bacterial agent. Representative, non-limiting anti-bacterial agents include penicillins, cephalosporins, flouroquinolones, aminoglycosides, monobactams and carbapenems and macrolides.

In one embodiment, the therapeutic agent is selected from oxicillin, doxycycline, demeclocycline; eravacycline, minocycline, ormadacycline, tetracycline, cephalexin, defotaxime, cetazidime, cefuroxime, ceftaroline; ciprofloxacin, levofloxacin, moxifloxacin clindamycin, lincomycin, metronidazole, azithromycin; clarithromycin, erythromycin, sulfamethoxazle and trimethoprim; sulfasalazine, amoxicillin and clavulanate; vancomycin, dalbavancin, oritavancin, telavancin, gentamycin, tobramycin, amikacin, imipenem and cilastatin, meropenem, doripenem, and ertapenem.

In a particular embodiment, the therapeutic agent is anti-fungal agent. Representative, non-limiting anti-fungal agents include azoles, polyenes and 5-fluorocytosine.

In a particular embodiment, the therapeutic agent is an anti-inflammatory agent.

In one embodiment, the anti-inflammatory agent is selected from aspirin, celecoxib, diclofenac, diflunisal, etodolac, ibuprofen, indomethacin, ketoprofen, ketorolac nabumetone, naproxen, nintedanib, oxaprozin, pirfenidone, piroxicam, salsalate, sulindac, tolmetin, and combinations thereof.

In a particular embodiment, the therapeutic agent is an anti-cancer agent.

In one embodiment, the anti-cancer agent is selected from an alkylating agent (or alkylating-like agent), an antimetabolite, an antitumor antibiotic, a plant alkaloid, a hormonal agent, a topoisomerase inhibitor or the like.

The processing in (ii) may vary and include, for example, diluting the sample or adding or more components to the assay, such as one or more binding agents. In certain embodiments, one or more of the capture agent, detector agent and reporter agent to the system or assay.

In a fourth aspect, a kit is disclosed containing one or more of the components of the systems or assays disclosed herein and optionally, instructions for use.

In a fifth aspect, a glucometer or chronoamperometer is disclosed which is configured for use in reading the result of an immunoassay.

In certain embodiment, the chronoamperometer utilizes modified chronoamperometric methods (e.g., techniques varying length and period of voltage application), optionally in combination with the titration of compounds or counterions critical to enzyme function (e.g., MgCl2). According to this embodiment, modified chronoamperometry enables one or more of the following: collecting signal (current, charge), increasing signal, improving signal to noise, improving sensitivity (e.g. limit of detection), reducing time to signal, multiplex on multiple working electrodes, and/or reducing background. Variables include but are not limited to enforced potential, delay before measurement, measurement time, time at open circuit, number of cycles, measurement sampling rate, etc.

In certain embodiment, the method does not utilize constant chronoamperometry. In another embodiment, the method does not utilize delayed chronoamperometry.

The systems, assays and methods disclosed herein advantageously permit detection of a target analyte(s) present in low concentrations in the sample.

In a particular embodiment, the system, assays and methods disclosed herein permit detection of a target protein or peptide (e.g., a viral protein or peptide, such as the N protein of a coronavirus such as SARS-CoV-2 or a variant thereof, such as the "Omicron" variant) at low concentrations in the sample.

In a particular embodiment, the system, assay and/or method disclosed herein permits detection of a target virus (e.g., a coronavirus such as SARS-CoV-2 or a variant thereof) with an LOD of about 100 fg/mL or less, more particularly, about 90, about 80, about 70, about 60, about 50, about 40, about 30, about 20, about 10, about 5 or about 1 fg/mL or less.

In a particular embodiment, the system, assay and/or method disclosed herein permits detection of a target virus (e.g., a coronavirus such as SARS-CoV-2 or a variant thereof) with an LOD of about 25 fg/mL or less.

In a particular embodiment, the system, assay and/or method disclosed herein permits detection of a target virus with an LOD of about $10^{12}$ TCID50/mL or less, more particularly, about $10^{11}$, about $10^{10}$, about $10^9$, about $10^8$, about $10^7$, about $10^6$, about $10^5$, about $10^4$, about 5000, about 2000, about 200, about 100, about 50, or about 25 TCID50/mL or less.

In another particular embodiment, the system, assay and/or method disclosed herein permits detection of a target virus with an LOD of about $10^{12}$ pfu/mL or less, more particularly, about $10^{11}$, about $10^{10}$, about $10^9$, about $10^8$, about $10^7$, about $10^6$, about $10^5$, about $10^4$, about 5000, about 2000, about 200, about 100, about 50, or about 25 pfu/mL or less.

In another particular embodiment, the system, assay and/or method disclosed herein permit a LOD of less than about 100 target analytes per millimeter, about 80 target analytes per mL or less, about 60 target analytes per mL or less, about 40 target analytes per mL or less, about 20 target analytes per mL or less, about 10 target analytes per mL or less, about 5 target analytes per mL or less or about 1 target analyte per mL.

In certain embodiments, the systems, assays and/or method disclosed herein permit an LOD of between about 1 target analyte per milliliter to about 100,000 target analytes per mL or more.

In certain embodiments, the system permits a LOD of between about 1 and about 5, between about 5 and about 10, between about 10 and about 20 or between about 20 and about 30 analytes per mL.

In certain embodiments, the systems and methods disclosed herein utilize pulsed detection.

In a particular embodiment, the processing in (ii) comprises diluting the sample in a liquid medium.

In certain embodiments, the systems, assays and methods disclosed herein permit a high degree of specificity and sensitivity. In some embodiments, the systems, assays and method at least about 90%, 91%, 92%, 93%, 94%, 95%, 96%, 97%, 98%, 99%, or 100% specificity. In some the systems, assays and methods permit at least about 90%, 91%, 92%, 93%, 94%, 95%, 96%, 97%, 98%, 99%, or 100% sensitivity.

In certain embodiments, the systems, assays and methods disclosed herein permit qualitative, semi-quantitative or quantitative detection of the at least one target analyte.

In certain embodiments, the systems, assays and/or methods disclosed herein permit simultaneous or sequential detection of multiple targets. In one embodiment, the systems, assays and/or methods permit simultaneous or sequential detection of two or more virus species or two or more strains of the same virus species.

In one embodiment, the systems, assays and/or methods permit simultaneous or sequential detection of a respiratory viruses selected from coronavirus (e.g., SARs-CoV-2), respiratory syncytial virus (RSV), influenza viruses and parainfluenza viruses (PIV), and adenovirus.

In certain embodiments, the systems, assays and/or methods permit simultaneous or sequential detection of a virus and a bacteria. In one embodiment, the virus is a respiratory virus and the bacterium is selected from *S. pneumoniae, H. influenzae, M. catarrhalis*, and *S. aureus*.

The multiplex system, assays or method may involve electrochemical or optical detection.

In certain embodiments, the simultaneous or sequential detection is qualitative, semi-quantitative or quantitative.

DESCRIPTION OF THE FIGURES

The accompanying drawings, which are incorporated into and constitute a part of this specification, illustrate one or more embodiments of the present disclosure and, together with the detailed description and examples sections, serve to explain the principles and implementations of the disclosure.

FIG. 5 includes materials that may be used to prepare sample as well as mixing options.

FIG. 9 shows use of a gel in place of flow to afford glucose addition and possibly optical detection.

FIG. 13 shows a microfluidic strip top view including 3 electrodes and reagent addition and mixing channels for added sample.

FIG. 14 shows a protocol for and an example of electrochemical detection of H1N1.

FIG. 16 shows initial selectivity data of CoV-2 strip against other viruses.

FIG. 18 shows more examples of colorimetric detection of H1N1.

FIG. 19 Shows an example of colorimetric detection of osteopontin.

FIG. 20 shows more examples of colorimetric detection of osteopontin.

FIG. 39 shows a schematic of a lateral flow device cartridge (top) that may be used in conjunction with a electrochemical reader (bottom).

FIG. 45 shows slope of chronoamperometry end currents from FIG. 44 as a function of concentration of IL-6. Top plot includes range of concentrations from 500 pg/ml down to 0; bottom plot expands lower concentrations of 20 pg/ml vs 0 for clarity. Error bars depict standard deviation of three samples. The line labeled "LoD" represents the current values three standard deviations above the 0 ng/mL baseline.

DETAILED DESCRIPTION

Figure 1:
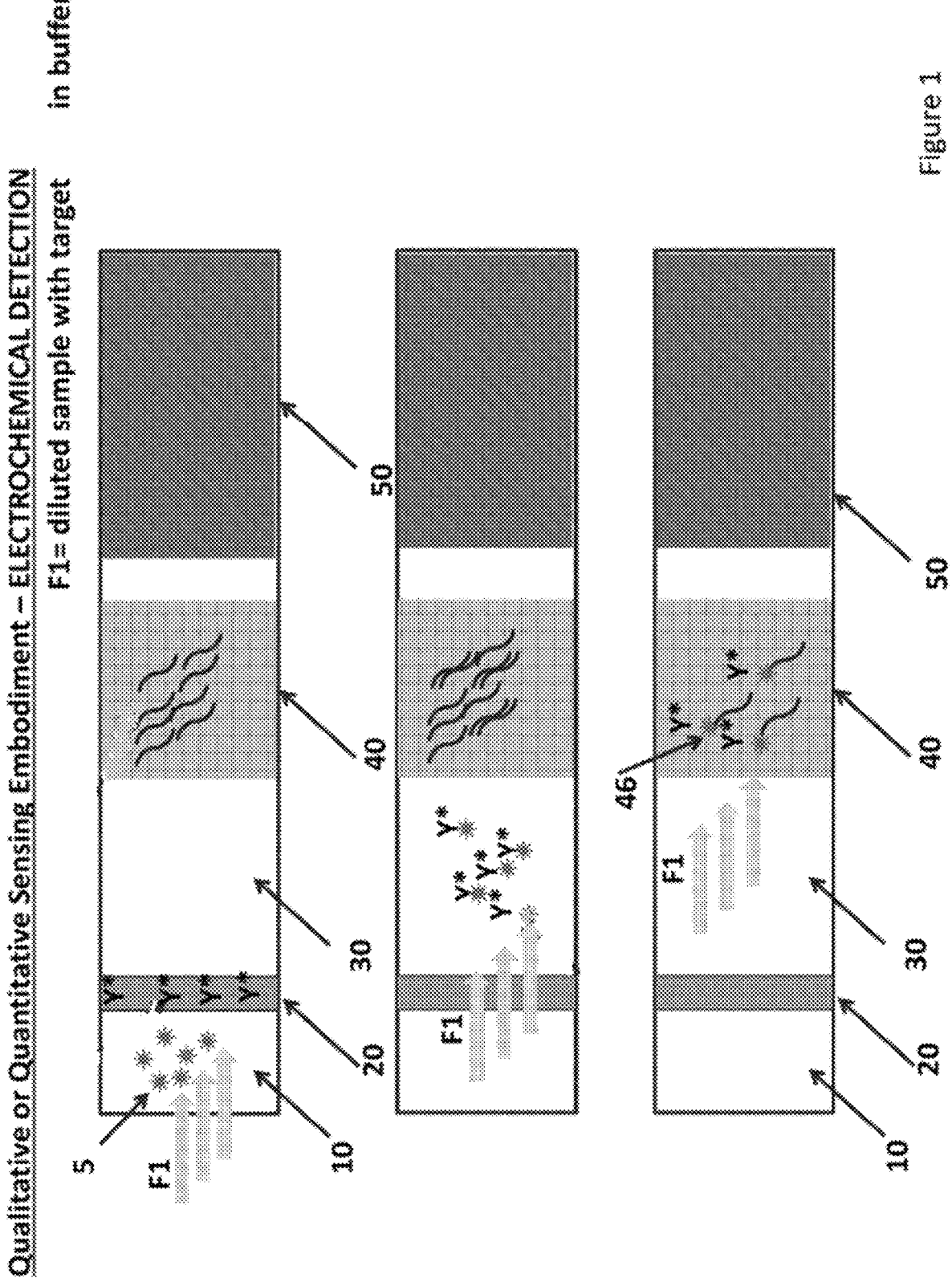
FIG. 1 shows a schematic top view procedural flow chart method for addition of target analyte in a sample applied to a strip with embedded chemistries which affords binding in a region of interest. As indicated by the numbering: 5 is the target; 10 is the sample pad; 20 is the conjugate pad region; 30 is the sample membrane; 40 is the test pad immobilization region; 50 is the absorbent pad/wicking pad; and 46 is the detectable complex or sandwich

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

Disclosed herein are systems, assays, kits and methods for using the same to determine the presence of at least one target analyte in a sample. Advantageously, the disclosed systems, assays, kits and methods permit the rapid, cost-effective detection of analytes and in certain embodiments,

I. Definitions

As used herein, the singular forms "a," "an," "or," and "the" include plural referents unless the context clearly dictates otherwise.

The term "about" as used herein in connection with any and all values (including lower and upper ends of numerical ranges) refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "administering" as used herein refers to the physical introduction of a therapeutic agent to a subject, using any of the various methods and delivery systems known to those skilled in the art. Exemplary routes of administration include oral, intravenous, intramuscular, subcutaneous, intraperitoneal, spinal or other parenteral routes of administration, for example by injection or infusion. Administering can also be performed, for example, once, a plurality of times, and/or over one or more extended periods.

The term "affinity" as used herein refers to a measure of the strength of the binding of between a target molecule and a binding agent. Affinity is typically expressed by a dissociation constant (Kd). Any Kd greater than about $10^{-6}$ M is generally considered to indicate nonspecific binding.

The term "amperometric" as used herein refers to a chemical titration in which the measurement of the electric current flowing under an applied potential difference between two electrodes in a solution is used for detecting the end point.

The term "antibiotic" as used herein refers to substance that inhibits the growth and replication of a bacterium.

Antibiotic compounds are generally classified as aminoglycosides, cephalosporins, fluoroquinolones, macrolides, penicillins, sulfonamides and tetracyclines.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR) or Joining (J) regions (JH or JL in heavy and light chains respectively). Each VH and VL is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (C1q) of the classical complement system. The term "antibody" is used herein in the broadest sense and encompasses various antibody structures, including but not limited to monoclonal antibodies, polyclonal antibodies, multi-specific antibodies (e.g., bispecific antibodies), and antibody fragments, so long as they exhibit the desired antigen-binding activity.

The term "antigen" as used herein refers to an entity (e.g., a proteinaceous entity or peptide) to which an antibody binds. In certain embodiments, the antigen is a coronavirus protein (e.g., a spike protein), or a derivative, fragment, analog, homolog or ortholog thereof, serves as the antigen in the systems and methods disclosed herein.

The term "antigen-binding region" refers to that portion of a binding agent that (e.g., antibody, aptamer) that interact with a target molecule (e.g., an antigen) and confer on the binding agents its specificity and affinity for the target molecule. In embodiments herein, the capture agent and optionally, the detector agent, bind to an antigen-binding region of the at least one target analyte. In certain embodiments, the capture agent and the detector agent bind to a first and second antigen-binding region of the target analyte, respectively.

The term "anti-viral drug" as used herein refers broadly to any anti-infective drug or therapy used to treat or ameliorate a viral infection in a subject.

The term "aptamer" as used herein refers to an oligonucleotide (DNA or RNA) that can conform in three-dimensions to bind another molecule with high affinity in the nanomolar and sub-nanomolar range. Exemplary nucleic acid molecules or polynucleotides comprising such aptamers include, but are not limited to, either D- or L-nucleic acids, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a .beta.-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof. Aptamers can be to other molecules include small molecules, proteins, nucleic acids, and even cells, tissues and organisms (e.g., whole virus) and may be monovalent or multivalent. Aptamers for use in the disclosed embodiments may be obtained by selection from a large random sequence library, using methods well known in the art, such Synthetic Evolution of Ligands by Exponential Enrichment (SELEX).

The term "assay" as used refers to an analytic procedure for qualitatively assessing or quantitatively measuring the presence, amount, or functional activity of a target analyte. In certain embodiments, the assay disclosed herein is not foldable of not intended to be foldable. In certain embodiments, the assay disclosed herein does not comprise a mixing chamber. In certain embodiments, the assay disclosed herein does not comprise an electroconductive polymer.

The term "array" as used herein meant a plurality of distinct sites bearing different capture agents. In certain embodiments, the assay component of the assays, systems and methods described herein comprises an array.

The term "binding agent" as used herein refers a molecule that bind (including hybridize) to a cognate ligand with high affinity and high specificity. A binding agent is typically used to identify the presence of its cognate ligand and can be detectably labeled to allow identification. A binding agent binds to its target analyte with high affinity and high specificity. Examples of binding agents include, e.g. an aptamer, an antibody, an antibody fragment, an antibody mimetic, an aptamer, an affimer, a quenchbody, a receptor ligand or a molecular imprinted polymer. In certain embodiments, the binding agent may be associated with, i.e., coupled, linked or connected, to a solid support such as a test strip or bead.

The term "binding pair" as used herein refers to a pair of molecules that bind to each other with high affinity and specificity. A "binding pair member" refers to one molecule of a binding pair. For example, streptavidin and biotin (or a biotin analog) are binding pair members that non-covalently bind with each other.

The term "binding affinity" as used herein refers to the tendency of a binding agent to bind or not bind a target and describes the measure of the strength of the binding or affinity of the binding agent to bind the target molecule.

The term "biomarker" as used herein refers generally to a molecule that is associated either quantitatively or qualitatively with a biological change. Examples of biomarkers include polypeptides, proteins or fragments of a polypeptide or protein; and polynucleotides, such as a gene product, RNA or RNA fragment, or encoding polynucleotides, hormones, small molecule; and other body metabolites. In certain embodiments, a "biomarker" means a small molecule compound that is differentially present (i.e., increased or decreased) in a biological sample from a subject or a group consisting of subjects having a first phenotype (e.g., having a disease or condition) as compared to a biological sample from a subject or group consisting of subjects having a second phenotype (e.g., not having the disease or condition or having a less severe version of the disease or condition).

The term "biosensor" as used herein refers to an analytic device comprising a biological detection element and a transducer. Various types of biosensors are known in the art. Electrochemical biosensors are based on the reaction of enzymatic catalysis that consumes or generates electrons and include, e.g., amperometric biosensors, potentiometric biosensors, impedimetric biosensors and voltammetric biosensors.

The term "buffer" refers to a liquid, which is suitable for supporting the binding reaction between the binding agent(s) and the target analyte(s). During incubation, the sample suspected to contain one or more target analytes, the buffer and potentially other liquids form a liquid phase.

The term "calibrated to" or "associated with" refer to the levels of a target analyte or a fragment thereof in a biological sample of a subject that has a statistically significant correlation with a physiologic state, e.g., disease status or extent of the disease, response to treatment, and survival. The strength of the correlation between levels of target analyte or a fragment thereof and the presence or absence of a particular physiologic state may be determined by a statistical test of significance.

The terms "camera," "photodetector," and the like as used herein refers to a component capable of detecting light intensity or composition to result in data, such as an image, of the light detected. The terms "camera" and "photo detector" can also refer to any type of detector including an RGB detector or spectrophotometer.

The term "capture agent" as used herein refers to an agent capable of binding and capturing a target analyte in a sample. Typically, the capture agent is immobilized or immobilizable (e.g., not immobilized at the time of capture, but thereafter immobilized). In a sandwich immunoassay, the capture agent can be any binding agent, e.g., an aptamer or antibody.

The term "colorimetric" as used herein refer to the physical description and quantification of the color spectrum including the human color perception spectrum (e.g., visible spectrum). In some embodiments, a colorimetric assay is particularly useful when quantification is not necessary. In certain embodiments, detection of the color change can be carried out by naked eye observation of a user (e.g., the person performing the assay) while in others a detection device is required. In some embodiments, calibrated colorimetric measurements could be used to determine the amount of target quantitatively.

The term "colorimetric material" as used herein refers to material that can produce a detectable change based on one or more substances in contact with the material. The detectable change can include a visible change such as a change in color, optical transmittance, or a change in emitted fluorescent or chemiluminescent light intensity or wavelength.

The term "chronoamperometry" as used herein refers to an electrochemical measuring technique used for electrochemical analysis or for the determination of the kinetics and mechanism of electrode reactions. A fast-rising potential pulse is enforced on the working (or reference) electrode of an electrochemical cell and the current flowing through this electrode is measured as a function of time by a chronoamperometer. The chronoamperometry methods disclosed herein may be standard or modified in some way (e.g., long pulse, short-interval or repeating pulse).

The term "cross-link" as used herein refers to a bond that links one polymer chain to another. These links may take the form of covalent bonds or ionic bonds and the polymers can be either synthetic polymers (e.g., polyethylene terephthalate) or natural polymers (such as proteins).

The term "competitive" when used herein with reference to an assay refers to an assay in which the number of binding sites is limited, resulting in a competition for binding between the endogenous analyte and a detectable, labeled analogue. As a result, the amount of labeled analogue bound is inversely proportional to the amount of analyte in the sample. As the amount of analyte in the sample increases, the detectable signal decreases. Competitive assays can be classified as simultaneous addition where all components are added at once or sequential addition where the sample is incubated with the antibody before the labeled analogue is added. In contrast, non-competitive immunoassays are designed to have excess binding sites and produce a signal directly proportional to the amount of analyte in the sample. In one embodiment, the assay disclosed herein is a sequential competitive assay. In another embodiment, the assay disclosed herein is a simultaneous addition competitive assay.

The term "complex" as used herein refers to an entity comprising more than one molecule which is bound or is in association with at least one other molecule, for example by a chemical association. Hence the term "matrix-aptamer-target molecule complex" relates to an association between the matrix, aptamer and the target molecule. The term "biotinylated second binding agent streptavidin (or "b-binding agent-SA complex") relates to an association between biotin, a second binding agent and streptavidin.

The term "control element" as used herein refers to an element that is used to provide information on the function of the assay, for example binding specificity, the level of non-specific background binding, the degree of binding cross-reactivity, and the performance of assay reagents and the detection system. Preferred controls useful herein include at least one negative control to monitor background signal, at least one negative control to monitor assay specificity, at least one positive colorimetric control, and at least one positive control to monitor assay performance.

The term "cross-reactivity", as used herein, refers to the ability of a binding agent (e.g., aptamer, antibody) directed against one target analyte to successfully bind with another, different molecule, i.e., a non-target molecule. The degree of cross-reactivity may vary. In certain embodiments, the target analyte and non-target analyte share a common epitope, i.e., a feature highly conserved across species.

The term "cut point", as used herein, refers to threshold value used to distinguish between a negative and a positive response in the assay. It is a constant value, determined statistically by analyzing assay responses of a set of drug-naïve diseased human samples.

The term "cytokine" as used herein refers to a category of immunoregulatory proteins, peptides or glycoproteins. In certain embodiments, the systems, assays and methods described herein are useful in the detection of cytokines such as pro-inflammatory cytokines, e.g., interleukin-8 (IL-8), interleukin-6 (IL-6), interleukin-1 (IL-1), interleukin-11 (IL-11), interleukin-17 (IL-17), interleukin-18 (IL-18), interferon-alpha (IFN-α), interferon–beta (IFN-β), interferon-gamma (IFN-7), G-CSF, tumor necrosis factor alpha (TNF-α) or tumor necrosis-factor beta (TNF-β).

The term "label" or "detectable label" as used herein refers to any molecule which produces, or can be induced to produce, a detectable signal. Non-limiting examples of labels include radioactive isotopes, enzymes, enzyme fragments, enzyme substrates, enzyme inhibitors, colorimetric labels, coenzymes, catalysts, fluorophores, dyes, chemiluminescers, luminescers, or sensitizers; a non-magnetic or magnetic particle, a solid support, a liposome, a ligand, or a receptor.

The term "detection device" as used herein refers to any device suitable for detecting the signal generated in the presence of the target analyte. Representative, non-limiting detection devices include amperometric devices, coulometric devices, potentiometric devices and voltammetric devices. In certain embodiments described herein, the detection device is a portable or hand-held device and in certain embodiments, a glucometer.

The term "diagnosis" as used herein refers to the recognition and (early) detection of a disease or clinical condition in a subject and may also comprise differential diagnosis. Also the assessment of the severity of a disease or clinical condition may in certain embodiments be encompassed by the term "diagnosis". In some embodiments, the term "diagnosis" encompasses an assessment of the severity of the disease or condition. Certain systems, assays and methods used herein provide the user with a diagnosis or, the information regarding the results as transmitted to a third party permits that third party to provide or confirm a diagnosis.

The term "drug" as used herein refers to a substance (e.g., a small molecule) used to treat or prevent a disease, or to ameliorate a manifestation of the disease, including but not limited to side effects and related risk factors and comorbidity. Also included in this definition are substances that are being developed for treatment or prevention of a disease, or amelioration of a manifestation of the disease.

The term "dropcasting" as used herein refers to a method in which a thin solid film is formed by dropping a solution onto a flat surface followed by evaporation of the solution.

The term "electrode" as used herein refers to any medium capable of transporting charge (e.g., electrons) to and/or from a storage molecule. Representative electrodes are metals or conductive organic molecules. In certain embodiments, the electrode comprises gold, silver, copper, platinum, aluminum, stainless steel, tungsten, indium tin oxide, titanium, lead, nickel, silicon, polyimide, parylene, benzocyclobutene, carbon, graphite, or any combination thereof. The electrodes can be manufactured to virtually any 2-dimensional or 3-dimensional shape (e.g., discrete lines, pads, planes, spheres, cylinders, etc.). In certain embodiments, the electrodes may be screen-printed. The electrode may be an analyte-specific electrode, positive control electrode, negative control electrode, counter electrode, reference electrodes or the like. The term "analyte-specific electrodes" refers to electrodes coated or otherwise functionalized with a binding agent. In certain embodiments, the electrode utilized in the assays and/or systems disclosed herein is not an oxide electrode. In certain embodiments, the systems and assays disclosed herein comprise a "wake-up" electrode to facilitate electronic engagement or measurement.

The term "electrochemical system" as used herein, refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/silver chloride. The electrochemical system can be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode, and positive control electrode. In the context of the present invention, a single electrochemical system may be used to quantify more than one type of analyte.

The term "environmental sample" as used herein encompasses a wide variety of sample types wherein The term "epitope" or "antigenic determinant" are used interchangeably herein and refer to that portion of a molecule such as an antigen capable of being recognized and specifically bound by a particular binding agent (e.g., antibody or aptamer). When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody. The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects.

The term "false negative" as used herein refers to a sample incorrectly identified not containing one or more analytes, e.g., viruses.

The term "false positive" as used herein refers to a sample incorrectly identified as containing one or more analysts, e.g., viruses.

The term "fragment" as used herein refers to a polypeptide or a polynucleotide having a sequence length of 1 to n−1, relative to a full-length polypeptide or polynucleotide (length is n). The length of the fragment can be appropriately changed according to the purpose thereof. Examples of a lower limit of the length thereof, in the case of a polypeptide, include 3, 4, 5, 6, 7, 8, 9, 10, 15, 20, 25, 30, 40, 50 and more amino acids, and a length represented by an integer which is not specifically listed herein (e.g. 11) can also be proper as a lower limit. In addition, in the case of a polynucleotide, examples of a lower limit of the length thereof include 5, 6, 7, 8, 9, 10, 15, 20, 25, 30, 40, 50, 75, 100, 200, 300, ×400, 500, 600, 700, 800, 900, 1000 and more nucleotides, and a length represented by an integer which is not specifically listed herein (e.g. 11) can also be proper as a lower limit. In certain embodiments, the systems, assays and methods described herein the target analyte is a fragment, e.g., a protein or nucleic acid fragment.

The term "glucometer" has used herein refers to a medical device commonly used by diabetic patients for self-monitoring of blood glucose levels. Many glucometers use an electrochemical method, based on test media such as test strips. Test strips are a consumable element containing chemicals that, in the context of diabetes monitoring, react with glucose in a drop of blood used for each measurement. Specifically, a chemical reaction is produced and the meter reads the level of glucose expressed in mg/dl or mmol/l. The glucometer is usually portable and is used at home although professional glucometers are known.

The term "glucose" as used herein refers to a monosaccharide, common hexose sugar.

The term "high affinity" as used herein refers to binding affinity of at least $10^{-8}$ M, between about $10^{-8}$ M and about $10^{-12}$ M, or more particularly, about $10^{-8}$ M, about $10^{-9}$ M; about $10^{-10}$ M, about $10^{-11}$ M, or about $10^{-12}$ M.

The term "hormone" as used herein refers to a chemical substance that controls and regulates the activity of certain cells or organs. Hormones can be classified as lipid-derived, amino acid-derived and peptide-derived. In certain embodiments, the assays, systems and methods disclosed herein are suitable for detecting lipid-derived (i.e., steroid) hormones include testosterone, estrogen and progesterone. In certain embodiments, the assays, systems and methods disclosed herein are suitable for use in detecting prolactin, a protein hormone.

The term "immobilized" as used herein refers to reversibly and irreversibly immobilized molecules (e.g., binding agents or analytes).

The term "instructional material," as used herein includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "isolated", "purified" or "biologically pure" as used herein refer to material that is substantially or essentially free from components which normally accompany it as found in its native state. Purity and homogeneity are typically determined using analytical chemistry techniques such as polyacrylamide gel electrophoresis or high-performance liquid chromatography. A protein that is the predominant species present in a preparation is substantially purified. In certain embodiments, purity of enzyme labeled capture agent and/or and detector is from about 10% to about 90% or more, more particular, about 10% or more, about 30% or more, about 50% or more, about 70%, or more, about 85% or more, about 90% or more, or more particularly, about 92%, about 95%, about 97% or about 99% or more.

The term "Kd" as used herein refers to the equilibrium dissociation constant of a particular binding agent-target molecule interaction. In certain embodiments herein, the Kd of the capture agent, the detector agent or both are about $10^{-10}$ Kd, about $10^{-8}$ Kd, or about $10^{-6}$.

The term "kit" as use herein refers to a collection of items intended for use together. The items in the kit may or may not be in operative connection with each other. A kit can comprise, e.g., antibodies or antigen-binding fragments as disclosed herein, optionally attached to a solid support, as well as reagents for performing assays and control reagents. Typically, items in a kit are contained in primary containers, such as vials, tubes, bottles, boxes or bags. Separate items can be contained in their own, separate containers or in the same container. Items in a kit, or primary containers of a kit, can be assembled into a secondary container, for example a box or a bag, optionally adapted for commercial sale, e.g., for shelving, or for transport by a common carrier, such as mail or delivery service.

The term "labeled" as used herein refers to molecule which produces, or can be induced to produce, a detectable signal. The label can be conjugated to an analyte, immunogen, antibody, or to another molecule. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "lateral flow assay" or "LFA" as used herein refers to an assay that can be used to identify at least one target analyte in a sample. The general format of LFA is similar to that of ELISA. Lateral flow technology is well-suited to point-of-care (POC) disease diagnostics because it is robust and inexpensive, without requiring power, a cold chain for storage and transport, or specialized reagents. An LFA device may comprise a solid substrate capable of supporting the test and which is made of a material which can absorb a liquid sample and which promotes capillary action of liquid sample along the solid support, such as nitrocellulose. The solid support can come in any shape or size, one common size being a strip that is capable of being held in a hand. The lateral flow assay may have more than one test line for multiplex testing for multiple target agents and are one embodiment of a "multiplexed" assay or system. As used herein, the term "lateral flow" refers to capillary flow through a material in a horizontal direction but will be understood to apply to the flow of a liquid from a point of application of the liquid to another lateral position even if, for example, the device is vertical or on an incline. Lateral flow depends upon properties of the liquid/substrate interaction (surface wetting or wicking action) and does not require or involve application of outside forces, e.g., vacuum or pressure applications by the user. By "capillary flow", it is meant liquid flow in which all of the dissolved or dispersed components of the liquid are carried at substantially equal rates and with relatively unimpaired flow laterally through the membrane, as opposed to preferential retention of one or more components as would occur, e.g., in materials capable of adsorbing or imbibing one or more components.

The term "layperson" as used herein means a subject lacking significant or any clinical training.

The term "Limit of Detection" or "LOD" as used herein refers to the lowest analyte concentration at which detection is feasible. LOD is determined by utilizing both the measured LOD and test replicates of a sample known to contain a low concentration of analyte. In some examples, LOD is determined by testing serial dilutions of a sample known to contain the analyte and determining the lowest dilution at which detection occurs.

The term "Limit of Quantification" or "LOQ" refers to the lowest concentration at which the analyte can not only be reliably detected but at which some predefined goals for bias and imprecision are met.

The terms "measuring" and "determining" are used interchangeably throughout and refer to methods which include obtaining a patient sample and/or detecting the level of a biomarker(s) in a biological sample. In one embodiment, the terms refer to obtaining a patient sample and detecting the level of one or more biomarkers in the sample. In another embodiment, the terms "measuring" and "determining" mean detecting the level of one or more biomarkers in a biologic sample. The term "measuring" is also used interchangeably throughout with the term "detecting."

The term "molecule" as used herein is used broadly to refer to natural, synthetic or semi-synthetic molecules or compounds.

The term "monitoring" as used herein with reference to a disease or disorder refers to keeping track of an already diagnosed disease, disorder, complication or risk, e.g. to analyze the progression of the disease or the influence of a particular treatment on the progression of disease or disorder.

The term "monoclonal antibody" as used herein refers to an antibody obtained from a population of substantially homogeneous antibodies, i.e., the individual antibodies comprising the population are identical except for possible naturally occurring mutations that can be present in minor amounts.

The term "multiplexed" as used herein with reference to an assay refers to use and/or testing of multiple target analytes simultaneously or sequentially in a single assay. In certain embodiments, the systems, assays and methods disclosed herein permit the user to detect more than one viral species or more than one strain of the same viral species. In certain embodiments, the systems, assays and methods disclosed herein permit the user to detect more than one bacterial species or more than one strain of the same bacterial species. In certain embodiments, the systems, assays and methods disclosed herein permit the user to detect a virus or bacteria, i.e., to distinguish between the viral or bacteria cause of an infection such as an upper respiratory infection. For example, to distinguish an infection caused by SARS-CoV-2, parainfluenza, rhinovirus, influenza A virus or influenza B virus. In another example, to distinguish an infection caused by a particular subtype of influenza A from another particular subtype of influenza A, e.g., influenza A subtype H1 and influenza A subtype H3. In a further example, to detect a significantly pathogenic coronavirus from a less pathogenic coronavirus. In other embodiments, the multiplex system, assay or method permits detection of different immunoglobulins.

The term "mutation" as used herein refers to a change in the amino acid sequence of a native protein. Mutations can be described by using the native sequence and then identifying the specific acid that have been changed. A "mutant" or "variant" refers to the protein that contains the mutation. A full-length mutant sequence refers to the full amino acid sequence of the mutant protein, instead of describing the mutant as the amino acids that are different from the native protein. In certain embodiments, the systems, assays and methods used herein can be used to detect two or more viruses, wherein the viruses are closely related variants.

The term "native protein" as used herein refers to a protein that is in its native or natural state and unaltered by any denaturing agent such as heat, chemical mutation or enzymatic reactions.

The term "non-target molecule" as used herein refers to a molecule that is not a biomarker of interest. In particular, a non-target molecule may be a molecule structurally similar to biomarker(s) of interest. In certain embodiments, the systems, assays and methods used herein can be used to distinguish between a target analyte and a non-target molecule, i.e., to detect the presence of the target analyte and not detect the presence of the non-target molecule even when both are present in the same sample.

The term "nucleic acid" as used herein refers to either deoxyribonucleic acid (DNA), ribonucleic acid (RNA), single-stranded or double-stranded and any chemical modifications thereof. The nucleic acid detected according to the systems, assays and/or methods disclosed herein may be a full length nucleic acid or a fragment thereof.

The term "oxidase" as used herein refers to enzymes that belong to the oxidoreductase class and catalyze the oxidation-reduction reaction using dioxygen as electron acceptor leading to formation of water (H2O) or hydrogen peroxide (H2O2) as by-product. This is in contrast to dehydrogenase enzymes, which transfer hydrogen to NAD, NADP, or a flavin in order to oxidize a substrate. Reductases can be oxidases since most redox reactions are reversible.

The term "oxidoreductase" as used herein refers to an enzyme that catalyzes the transfer of electrons from one molecule, the reductant, also called the electron donor, to another, the oxidant, also called the electron acceptor. Oxidoreuctases can be categorized into different subtypes, including oxidases, dehydrogenases, reductases, peroxidases, hydroxylases, and oxygenases.

The term "pathogen" as used herein means any disease-producing agent including, but not limited to, a virus or bacterium, fungi, protozoa or other microorganism. Replicating pathogens (e.g., viruses, parasites and bacteria), are organisms that cause disease by using the body's resources to replicate while largely avoiding the body's immune response.

The term "pesticide" as used herein means a chemical used to kill pests. Pesticides are generally classified as fungicides, herbicides, insecticides, and rodenticides.

The term "point of care testing" or "POCT" as used herein refers to biological specimens assayed at or near the patient with the assumption that test results will be available instantly or in a very short timeframe to assist caregivers with immediate diagnosis and/or clinical intervention. (Ehrmeyer S S et al. (2007) Clin Chem Lab Med 45: 766-773). The term is not intended to be limiting to patients and home use, but inclusive of a variety of setting (e.g. communities, clinics, peripheral laboratories and hospitals) and users (e.g. technicians and caregivers). Depending on the setting and the user, the purpose of POCT may vary—from triage and referral, to diagnosis, treatment, and monitoring. In the context of an environmental sample, a similar concept is field testing, i.e., testing at the sample collection site.

The term "potentiostat" as used herein is a broad term and is used in its ordinary sense, including, without limitation, an electrical system that controls the potential between the working and reference electrodes of a three-electrode cell at a preset value. It forces whatever current is necessary to flow between the working and counter electrodes to keep the desired potential, as long as the needed cell voltage and current do not exceed the compliance limits of the potentiostat. A bipotentiostate and a polypotentiostat are potentiostats capable of controlling two working electrodes and more than two working electrodes, respectively The term "pre-determined threshold (value)" as used herein refers to the threshold numeric value at which a classifier gives the desirable balance between (the cost of) false negatives and false positives. In some embodiments, "pre-determined threshold" is statistically (and clinically) determined, refined, adjusted and/or confirmed through, on, or based on, a clinical study and analyses of outcome thereof (collectively, "clinical data"), and/or a preclinical or non-clinical study (collectively, "non-clinical data"), in order to minimize undesirable effects of false positives and false negatives.

The terms "prevent", "preventing" or "prevention" as used herein refers to inhibition of manifestation of a pathologic condition, e.g., symptoms or indications of pathology, such as symptoms or indications of a viral infection.

The term "processor" as used herein is used broadly to refer to a programmable or non-programmable processing device, such as a microprocessor, microcontroller, application-specific integrated circuits (ASICS), programmable logic devices (PLDs), field-programmable gate arrays (FPGAs), etc. The term "processor" may also include multiple processing devices working in conjunction with one another.

The term "point mutation" as used herein refers to the engineering of a polynucleotide that results in the expression of an amino acid sequence that differs from the non-engineered amino acid sequence in the substitution or exchange, deletion or insertion of one or more single (non-consecutive) or doublets of amino acids for different amino acids.

The terms "protein", "peptide", and "polypeptide" are used interchangeably herein to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. The protein detected according to the assays, systems and/or methods disclosed herein may be a full length protein or protein fragment. In a particular embodiment, the target analyte detected according to the systems, assays and methods disclosed herein is a nucleocapsid (N) protein of a coronavirus and more particularly, SARS-CoV-2 or a variant thereof. In another particular embodiment, the target analyte detected according to the systems, assays and methods disclosed herein is osteopontin, an integrin-binding glycoprotein.

The term "pulse" refers to a burst of current, voltage, or electromagnetic-field energy. A pulse may last from a fraction of a nanosecond up to several seconds or even minutes.

The term "quantitative" as used herein with respect to the methods and systems described herein refers to information on the concentration of an analyte relative to a reference (control), which may be reported numerically, where a "zero" value can be assigned where the analyte is below the limit of detection. "Semi-quantitative" methods and systems involve presentation of a numeric representation of the amount of the analyte in the specimen that is relative to a reference (e.g., a threshold, e.g., normal threshold or an abnormal threshold), where a "zero" value can be assigned where the analyte is below the limit of detection. In general, semi-quantitative results are compared against an accompanying reference to provide a qualitative interpretation of the result. In certain embodiments, the systems, assays and methods disclosed herein permit a quantitative or semi-quantitative result.

The term "rapid diagnostic test" as used herein refers to a system or assay for testing of a sample, which can be carried out at the point of care or at the location of the user (e.g., home, office, field) to obtain fast diagnosis. The rapid diagnostic test quick and easy to perform and can be carried out even in the absence of laboratory techniques such as microscopy, enzyme-linked immunosorbent assay (ELISA) or polymerase chain reaction (PCR). By way of a non-limiting example, rapid diagnostic test generally requires about 30 minutes or less (e.g., about 10 minutes or less, about 2 minutes or less, about 1 min or less) from the time of sample collection to the time of obtaining a result. It should be noted that time required for a rapid diagnostic testing depends on variables, such as the type of sample, the amount of sample, the nature of the analyte, and the like.

The term "reference value" as used herein can be a "threshold value" or a "cut-off value". Typically, a "threshold value" or "cut-off value" can be determined experimentally, empirically, or theoretically.

The term "reporter agent" as used herein refers to an agent that is a component of a dual detection strategy, where the reporter agent may be a labeled detector agent or an agent (e.g., an enzyme) in solution.

The term "risk" as used herein refers to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no conversion. Alternative continuous measures, which may be assessed in the context of the present invention.

The term "selectivity" as used herein refers to the ability a system, assay or method to discriminate a particular analyte in a complex mixture without interference from other components.

The term "sensor" as used herein refers to a means used to detect at least one target analyte. A "sensor system" includes, for example, elements, structures and architectures intended to facilitate sensor use and function. Sensor systems can include, for example, compositions such as those having selected material properties, as well as electronic components such as elements and devices used in signal detection and analysis (e.g. current detectors, monitors, processors and the like).

The term "small molecule" as used herein refers to a low molecular mass (or molecular weight) (e.g., 2000 g/mole). The small molecule can be organic or inorganic, or metallo-organic. Examples of small molecules include drugs (e.g., therapeutic drugs, drugs of abuse), heavy metals, hormones and growth promoters, molecular markers, pesticides and toxins. The term "small molecule" refers to a molecule having a molecular weight of about 150 to about 2,000, or about 150 to about 1,500, or about 150 to about 1,000, or about 150 to about 500, or about 300 to about 2,000, or about 300 to about 1,500, or about 300 to about 1,000, or about 500 to about 2,000, or about 500 to about 1,500, or about 500 to about 1,000, for example.

The term "solid support" as used herein refers to a solid material to which binding agents can be attached. Exemplary solid supports include, without limitation, beads or particles (e.g., made of, sepharose), microtiter plates, microchips, filters, membranes or fibers, e.g., microfibers.

The term "specific binding", "specifically binds," "selective binding," and "selectively binds" mean that a binding agent (e.g., antibody, aptamer) exhibits appreciable affinity for a target molecule and, generally, does not exhibit significant cross-reactivity with non-target molecules, which in certain embodiments means having an equilibrium dissociation constant of at least about $1\times10^{-8}$ M or less (e.g., a smaller Kd denotes a tighter binding). Methods for determining whether two molecules specifically bind are well known in the art and include, for example, equilibrium dialysis or surface plasmon resonance. In certain embodiments described herein, the capture agent and optionally, the detector agent, specifically bind to the at least one target analyte.

The term "sensitivity" as used herein refers to proportion of positives that are correctly identified (e.g., the percentage of positive people that are identified by a system or method). In a highly sensitive system or method, false negatives are limited.

The term "specificity" as used herein refers the proportion of negatives that are correctly identified. In a highly specific system or method, false positives are limited.

The term "screen printing" as used herein refers to a technique comprising printing different types of ink on substrate. The inks composition may vary and include carbon, silver, gold, and platinum, for example. Screen printing permits the reproducible production of high-quality disposable electrodes at low cost. Other printing methods or other methods to form the electrodes are known in the art.

The term "subject" refers to a mammal, such as a human. In certain embodiments, the subject is suspected of having a disease or disorder (e.g., a viral infection), currently has a disease or disorder (e.g., viral infection), recently recovered from a disease or disorder (e.g., a viral infection) or is at risk for contracting a disease or disorder (e.g., a viral infection).

The term "system" as used herein refers to a group of objects and/or devices that form a network for performing a desired objective The term "system noise" as used herein refers to without limitation, unwanted electronic or diffusion-related noise which can include Gaussian, motion-related, flicker, kinetic, or other white noise, for example. In certain embodiments described herein, the system has reduced noise compared to detection systems known in the art. In certain embodiments, the noise is reduced by about 5%, about 10%, about 15%, about 20%, about 25%, about 30%, about 35%, about 45%, about 50% or more.

The term "target" as used herein is a broad term used to refer to a substance or chemical constituent in a fluid such as a biological fluid or an environmental sample such as water, oil, fuel, mud, sediment, mold, combinations thereof, etc. The target may be naturally present or may be an extrinsic substance. The target may be a toxin, may be a catalyst, an additive, etc.

The term "target analyte" as used herein refers to a denotes a molecule or other analyte which may be found in a tested sample and which is capable of binding to a binding agent. In certain embodiments, the target analyte is a pathogenic organism (e.g., a virus or bacteria), a protein, a peptide, a hormone, a steroid, a vitamin (e.g., biotin), a small molecule (e.g., drugs, drug intermediates), an organic compound or a toxin. In certain embodiments, the target analyte detected by the assays, systems and methods disclosed herein is not nicotine. In certain embodiments, the target analyte detected by the assays, systems and methods disclosed herein is not RNA. In certain embodiments, the target analyte detected by the assays, systems and methods disclosed herein is not an oxidase microbial redox enzyme (MRE).

The terms "treatment" and "treating" as used herein refer to preventing, inhibiting, and alleviating conditions and symptoms associated with disorders or diseases.

The term "therapeutically effective amount" as used herein refers to that amount of active compound or pharmaceutical agent (e.g., an anti-viral drug) that elicits the biological or medicinal response in a subject that is being sought by a researcher, veterinarian, medical doctor or other clinician, which includes preventing, ameliorating or alleviating the symptoms of the disease or disorder being treated. Methods are known in the art for determining therapeutically effective doses for the instant pharmaceutical composition. In certain methods described herein, the method comprising administering a therapeutically effective amount of at least one approved therapeutic agent to a subject.

The term "two binding agent assay" refers to the target analyte attached to the first binding agent bound to the matrix further incubating in the presence of a second binding agent associated with a chemical reactive group. The incubation of the two binding agents may be simultaneous.

The term "variant" as used herein is a relative term that describes the relationship between a particular polypeptide of interest and a "parent" or "reference" polypeptide to which its sequence is being compared. A polypeptide of interest is considered to be a "variant" of a parent or reference polypeptide if the polypeptide of interest has an amino acid sequence that is identical to that of the parent but for a small number of sequence alterations at particular positions. Variants include, for example, substitutional, insertional or deletion variant. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide. In a particular embodiment, a variant is a viral protein (e.g., a spike protein) that is similar to a reference viral protein, particularly in its function, but have mutations in their amino acid sequence that make them different in sequence from the wild-type viral protein at one or more positions. In the context of SARS-CoV-2, the "wild-type" genome has been sequenced and is known in the art (see e.g., Wu et al. (2020) cell Host & Microbe 27(3): 325-328; Wang, H., et al (2020). Eur J Clin Microbiol Infect Dis 39, 1629-1635). Thus, "SARS-CoV-2 variants" include variants that currently exist, as well as variants that may arise or be discovered in the future.

The term "vertical flow assay" (also known as a flow-through assay) refers to an assay where the liquid sample flows vertically in the assay, as opposed to laterally as in an LFA. One embodiment replaces the conventional lateral flow segments in a stacking manner (e.g., stacked membranes) permitting the liquid to diffuse from the bottom to the top layers. See, e.g., E. Eltzov, Biosens. Bioelectron., 87 (2017), pp. 572-578. Another embodiment pushes the reagents through a single membrane in steps, and allow for the targets to react with the reagents on the membrane. Multiplexing is achieved in a vertical flow assay by providing a capture antigen for different antigens at pre-determined locations (spatially multiplexed) and/or patterns on the solid support, e.g., polymer membrane. Advantageously, the vertical flow assays described herein do not require syringe pumps for fluid handling or benchtop read-out devices for assay analysis. In certain embodiments, the vertical flow assay described herein avoids diffusion limited kinetics and exhibits significantly reduced assay time compared to conventional assays.

The term "viral species" as used herein refers to a monophyletic group of viruses whose properties can be distinguished from those of other species by multiple criteria.

The term "wild-type", as used herein, refers to a native full-length form of a protein or nucleic acid, as is found in nature. The term full length native protein sequence, as used herein, refers to the amino acid sequence found in the full-length native protein. The wild-type protein may be obtained, for example, from a biological sample.

The term "whole virus" as used herein refers to an intact or largely intact viral agent. In certain embodiments, the methods and systems disclosed herein are not used to detect or quantity whole virus particles, but instead to detect or quantify specific viral proteins. In one embodiment, the methods and systems disclosed herein are used to detect or quantify soluble viral proteins.

For any method disclosed herein that includes discrete steps, the steps may be conducted in any feasible order. And, as appropriate, any combination of two or more steps may be conducted simultaneously.

I. Systems and Assays

Disclosed herein are systems and assays (sensors) for detecting at least one target analyte in a sample, e.g., a fluid sample. In certain embodiments, the sample is processed but not extracted. The sample may contain one or a plurality of target analytes (e.g., one, two, three, four, five, six, seven, eight, nine or ten target analytes or more).

The systems and assays are suitable for rapid diagnostic tests that are relatively less time consuming and less labor intensive as compared to conventional methods and in certain embodiments, the ease of handling and interpretation of results make it possible for testing outside of a conventional setting (e.g., in the home or in the field as opposed to a laboratory or clinical setting) by a relatively untrained user (e.g., layperson). In certain embodiments, the systems and assays disclosed herein are intended for a single-user. Advantageously, the systems and assays permit a relatively low limit of detection (LOD) and high degree of accuracy, as described further herein. In certain embodiments, the systems described herein utilize modified chronoamperometric methods to permit faster and/or more sensitive measurements (e.g. afford lower LOD).

In one embodiment, a system is provided for detecting at least one target analyte (e.g., a whole virus or viral protein) in a sample (e.g., a biological sample such as blood, nasal mucus, sputum, saliva, or urine), wherein the system comprises (i) an assay comprising at least a capture agent (e.g., an aptamer or antibody) capable of directly or indirectly generating an enzyme-mediated signal (e.g., an oxidase-mediated signal) in the presence of the at least one target analyte and added substrate (e.g., glucose solution), and (ii) a detection device (e.g., a glucometer) for detecting the signal. In certain embodiments, the detection device comprises a sensor selected from an electrochemical sensor, an optical sensor or a combination thereof. In certain embodiments, the detection device produces a result within about thirty minutes or less. In certain embodiments, the signal is calibrated to the concentration of enzyme.

In certain embodiments, the system further comprises a detector agent (e.g., an aptamer or antibody). In one embodiment, the detector agent is added to the system by the user, i.e., an added detector agent. In a particular embodiment, the detector agent is labeled (e.g., with an enzyme label) and binds to the target analyte, creating a detectable complex.

In a particular embodiment, the capture agent is immobilized on a solid support, e.g., a test strip, to provide a test site.

In certain embodiments, the capture agent is immobilizable but not initially immobilized, i.e., at the time the target analyte is bound or prior to the formation of the detectable complex. According to this embodiment, the capture agent and detector agent are present in the system upstream of the electrode and form the detectable complex upon addition of the analyte solution to the system. The detectable complex is then captured on the solid support in proximity to the electrode.

In certain embodiments, the substrate (e.g., sugar, such as glucose, or diethanolamine) or is an added substrate, i.e., added to the system by the user.

In certain embodiments, the system further comprises a first binding agent. According to this embodiment, the first binding agent is immobilized to a solid support.

In certain embodiments, the first binding agent comprises a first binding site that binds to a second binding agent (e.g., biotin) conjugated to the capture agent.

In certain embodiments, the first binding agent contains a second binding site and the assay further comprises a polymer (e.g., PEG), wherein the polymer binds to the first binding agent at the secondi binding site. According to this embodiment, the first binding agents are cross-linked.

In certain embodiments, the second binding agent comprises a third binding agent, wherein the third binding agent (e.g., biotin) is conjugated to the capture agent to permit binding to one or more additional capture agents. According to this embodiment, the capture agents are cross-linked.

In certain embodiments, the solid support or substrate is a bead, a membrane or a bead immobilized on a membrane. In certain embodiments, the solid substrate is not a metal particle.

In a particular embodiment, the capture agent, the detector agent or both are added reagents, i.e., added to the system by the user.

In certain embodiments, the substrate (e.g., sugar, such as glucose, or diethanolamine) is an added substrate, i.e., added to the system or assay by the user. In one embodiment, the substrate is added in excess.

In one embodiment, the enzyme label is an oxidoreductase. The oxidoreductase may be selected from the group consisting of oxidases, dehydrogenases, hydrogenases, peroxidases, phosphatases, hydroxylases, oxygenases, catalases and reductases.

Representative, non-limiting oxidases include glucose oxidase, galactose oxidase, D-glucose: D-fructose oxidoreductase, and cellobiose oxidase.

In a particular embodiment, the enzyme label is selected from horseradish peroxidase (HRP), alkaline phosphatase (AP), glucose oxidase (GO) and β-galactosidase.

In one embodiment, the enzyme is glucose oxidase and the substrate is glucose.

In one embodiment, the enzyme is alkaline phosphatase and the substrate is), pyridoxal-5'-phosphate (PLP), or 5-bromo-4-chloro-3-indolyl-phosphate, or L-ascorbic acid-2-phosphate, acetaminophen phosphate, 4-acetamidophenyl phosphate, or 4-aminophenyl phosphate in diethanolamine (DEA), 1-amino-2-propanol, N-methyl-D-glucamine or tris buffer.

In one embodiment, the enzyme is β-galactosidase and the substrate is galactose.

In one embodiment, the enzyme is horseradish peroxidase and the substrate is a chromogenic HRP substrate, e.g., 3,3',5,5'-tetramethylbenzidine (TMB) and 2,2'-azino-di-[3-ethylbenzthiazoline-6-sulfonic acid] (ABTS).

In one embodiment, the enzyme-mediated signal comprises a dual detection system, wherein the dual detection system comprises a first and second enzyme label, e.g., an oxidase label (e.g., an oxidase label) and a peroxidase label (e.g., hydrogen peroxide).

In another embodiment, the Vmax of the enzyme linked to the detector agent is greater than 0.0001 mM/min, greater than 0.01 mM/min, greater than 0.1 mM/min, or greater than >10 mM/min.

In another embodiment, the kcat of the enzyme linked to the detector agent is greater than $1 \text{ s}^{-1}$, greater than $10 \text{ s}^{-1}$, greater than $50 \text{ s}^{-1}$, or greater than $100 \text{ s}^{-1}$.

In another embodiment, the kcat/Km value of the enzyme linked to the detector agent is greater than $0.00001 \text{ mM s}^{-1}$, greater than $0.01 \text{ mM s}^{-1}$, greater than, $1 \text{ mM s}^{-1}$, or greater than $10 \text{ mM s}^{-1}$.

In a particular embodiment, the capture agent is provided in a hydrogel located on or in the solid support. The hydrogel may be saturated with substrate, e.g., glucose.

In one embodiment, the assay is a lateral flow assay (LFA). In a particular embodiment, the lateral flow assay comprises at least one test site comprising the at least one capture binding agent. Optionally, the lateral flow assay further comprises at least one control site comprising at least one control element, in order to monitor the performance of the system.

In one embodiment, the system is an electrochemical system or an optical system. In particular, the sensor produces an output that is calibrated against the presence or concentration of the target analyte(s). In a particular embodiment, the electrochemical detection is only performed upon insertion of the strip into the electrochemical device providing the differential voltage and detecting the current output provided by the strip and accompanying electrode.

In a particular embodiment, the system is an electrochemical system that comprises at least one electrode located at, above or underneath the target site. Optionally, the at least one binding agent may be bound to the electrode.

In one embodiment, the system is a system for self-monitoring. In a particular embodiment, the detection device is a glucometer or mobile phone.

In embodiment, information regarding the signal is transmitted to a third party for diagnosis and optionally, treatment.

In one embodiment, the system permits detection of the at least one target analyte in about 10 minutes or less, about 5 minutes or less, about 2 minutes or less or about 1 minute or less.

In one embodiment, the system disclosed herein permits improved disease diagnosis, monitoring, management or combinations thereof.

In certain embodiments, the system stores multiple test results for the same user taken at different times and comparing these to monitor or predict the likely development of a disease or condition. In one embodiment, the system permits obtaining two or more results, three or more results or five or more results with respect to the quantity of a target analyte for the same user at different times, to permit monitoring of a trend in analyte level over time.

In another embodiment, an assay (e.g., a hand-held assay) is provided for detecting at least one target analyte (e.g., a whole virus) comprising a first binding agent (e.g., streptavidin) and a capture agent (e.g., an aptamer or antibody) wherein the capture agent is capable of directly or indirectly generating an enzyme-mediated signal (e.g., an oxidase-mediated signal) in the presence of the at least one target analyte and substrate (e.g., glucose solution). In certain embodiments, the signal is proportional to the concentration of enzyme. In certain embodiments, the signal can be detected in 30 minutes or less.

In certain embodiments, the system further comprises a detector agent (e.g., an aptamer or antibody), wherein the capture agent and the detector agent form a detectable complex when the target analyte is present.

In one embodiment, the detector agent is an added detector agent, i.e., added to the system by the user.

In a particular embodiment, the substrate is an added substrate, i.e., added to the system by the user.

In certain embodiments, the first binding agent comprises a first binding site that binds to a second binding agent (e.g., biotin) conjugated to the capture agent.

In certain embodiments, the first binding agent contains a second binding site and the assay further comprises a polymer (e.g., PEG), wherein the polymer binds to the first binding agent at the seconding binding site. According to this embodiment, the first binding agents are cross-linked.

In certain embodiments, the second binding agent comprises a third binding agent, wherein the third binding agent (e.g., biotin) is conjugated to the capture agent to permit binding to one or more additional capture agents. According to this embodiment, the capture agents are cross-linked.

In certain embodiments, the solid substrate is a bead, a membrane or a bead immobilized on a membrane.

In a particular embodiment, the capture agent, the detector agent or both are added reagents, i.e., added to the system by the user.

In certain embodiments, the substrate is an added substrate, i.e., added to the system by the user.

In a particular embodiment, the enzyme label is an oxidase (e.g., a glucose oxidase) or dehydrogenase.

In one embodiment, the assay is a lateral flow assay. In a particular embodiment, the assay is a multiplexed lateral flow assay.

In another embodiment, the assay is a vertical flow assay. In one embodiment, the vertical flow assay consists of one layer, two layers or three layers or more (e.g., one, two or three membrane layers or more). In one embodiment, assay is a multiplex sandwich vertical flow assay.

In a particular embodiment, the vertical flow assay comprising a first membrane layer comprising an immobilized capture agent, a second membrane layer comprising the target analyte and a third membrane layer comprising a labeled detector agent.

In one embodiment, the detectable complex is detected without the aid of a detection device.

In another embodiments, the detectable complex is detected by a detection device. The detection device may be, for example, a glucometer or a mobile phone.

In one embodiment, the enzyme-mediated signal comprises a dual detection system, wherein the dual detection system comprises an enzyme label (e.g., an oxidase) and a reporter label (e.g., horseradish peroxidase). In certain embodiments, the signal is colorimetric.

In one embodiment, the target analyte(s) is a protein or peptide (e.g., a viral protein, such as a nucleocapsid protein, or a protein-derived hormone) and the system permits a level of detection (LOD) of about 1.0 ng/mL or less, about 0.8 ng/mL or less, about 0.6 ng/mL or less, about 0.4 ng/mL or less, about 0.2 ng/mL or less, about 0.1 ng/mL or less. In certain embodiments, the system, assay and/or method disclosed herein permits this LOD in 30 minutes or less, in 15 minutes or less, in 10 minutes or less, in 5 minutes or less or in 1 minute or less.

In certain embodiments, the target analyte(s) is small molecule and the system permits an LOD ranging from about 0.01 to about 100 ng/mL, from about 0.1 to 10 ng/mL, from 0.2 to 5 ng/mL, or from about 0.2 to about 1.0 ng/mL. In certain embodiments, the system, assay and/or method disclosed herein permits this LOD in 30 minutes or less, in 15 minutes or less, in 10 minutes or less, in 5 minutes or less or in 1 minute or less.

In certain embodiments, the target analyte is whole virus and the system permits an LOD of about 1012 TCID50/mL or less, more particularly, about 1011, about 1010, about 109, about 108, about 107, about 106, about 105, about 104, about 5000 TCID50/mL or less, about 20000 TCID50/mL or less, about 10000 TCID50/mL or less, about 5000 TCID50/mL or less, about 1000 TCID50/mL or less, about 500 TCID50/mL, about 300 TCID50/mL, about 100 TCID50/mL, about 50 TCID50/mL or less, about 20 TCID50/mL, or about 15 TCID50/mL or less. In certain embodiments, the system, assay and/or method disclosed herein permits this LOD in 30 minutes or less, in 15 minutes or less, in 10 minutes or less, in 5 minutes or less or in 1 minute or less.

In another embodiment, the target analyte is a whole virus and the system permits a LOD ranging from about 13 to about 50000 TCID50/mL, more particularly about 13 to about 20000 TCID50/mL, more particularly about 50 to about 10,000 TCID50/mL, 50 to about 104 TCID50/mL, 50 to about 105 TCID50/mL, 50 to about 106 TCID50/mL, 50 to about 107 TCID50/mL, 50 to about 108 TCID50/mL, 50 to about 109 TCID50/mL, 50 to about 1010 TCID50/mL, 50 to about 1011 TCID50/mL, 50 to about 1012 TCID50/mL. In certain embodiments, the system, assay and/or method disclosed herein permits this LOD in 30 minutes or less, in 15 minutes or less, in 10 minutes, in 5 minutes or less or in 1 minutes or less.

In one embodiment, the systems, assays and methods disclosed herein permits LOD within the range of about 101 to about 1011 proteins copies per mL.

In one embodiment, the systems and assays disclosed herein permits detection of about 10 to 1,000 small molecules in solution, well below the current clinical range of interest. In one embodiment, the system permits detection of about 10 to about 100 small molecules in solution, or about 10 to about 50 and more particularly about 10 to about 20 small molecules in solution.

In one embodiment, the system disclosed herein with a limit of detection of about 10 small molecules/mL or 10 analyte per mL or similar concentration.

In on embodiment, the systems, assays and/or methods disclosed herein permit detection of about 1000, about 900, about 800, about 700, about 600, about 500, about 400, about 300, about 200, about 100 or less viral particles per mL or similar concentration.

In a particular embodiment, the systems, assays and/or methods disclosed herein permit detection about 100 or less viral particles per mL, or more particularly, about 90, about 85, about 80, about 75, about 70, about 65, about 60, about 55, or about 50 viral particles per mL.

In one embodiment, the time to result is from 1 second to 30 minutes, preferably from 10 seconds to 15 minutes, more preferably from about 20 seconds to 8 minutes, still more preferably from 30 seconds to 5 minutes.

In one embodiment, the assay permits detection of the at least one target analyte in 10 minutes or less, 5 minutes or less, 2 minutes or less or 1 minute or less.

The systems and assays disclosed herein exhibit properties that are desirable to the user and in some instances, improved over prior art assays and systems. These properties may include, without limitation, speed and duration of sensing (<about 1 minute), specificity (>about 90%), selectivity (>about 90%), limit of detection of the assay (1 target analyte per milliliter to >100,000 target analytes per milliliter), quantitative detection (>about 90% precision and >about 90% accuracy), the effect of common interferents to the sensor output, cross-reactivity (>about 90% selectivity for target analyte) (e.g., between related proteins for example phosphorylated or not), dynamic range, coefficient of variation of repeated measurements (<about 0% variance), operational stability or combinations thereof. In one embodiment, the analysis of variance with five (5) variables, depending on the statistical method used, can achieve convergence greater than 0.95 with five (5) measurements. With standardization of manufacturing, reducing the variables to one or two, the confidence level can be obtained with two (2) measurements. In certain embodiments, the systems and assays disclosed herein utilize modified chronoamperometric methods to achieve desirable properties, i.e., superior to those achievable with constant or delayed chronoamperometry.

In one embodiment, the system or assay permits about 90% or greater, about 91% or greater, about 92% or greater, about 93% or greater, about 94% or greater, about 95% or greater, about 96% or greater, about 97% or greater, about 98% or greater, or about 99% or greater sensitivity.

In a particular embodiment, out of 10 tests, the system permits 9 true positive tests with 1 false negative test.

In one embodiment, the system or assay permits about 90% or greater, about 91% or greater, about 92% or greater, about 93% or greater, about 94% or greater, about 95% or greater, about 96% or greater, about 97% or greater, about 98% or greater, or about 99% or greater sensitivity. The advantages of this high sensitivity are that a very early detection can be carried out, for example before any symptom(s) are apparent. This is especially useful for detecting a disease state in subjects who have been in contact with other individuals who are infectious.

In one embodiment, the redox analyte solution may be influenced by compounds and counterions to become more or less sensitive, which may affect system sensitivity. In certain embodiments, the titration of compounds or counterions critical to enzyme function may permit more sensitive detection of a target analyte. See, for example, Example 19 which shows that that titration of $MgCl_2$ into DEA buffer can increase assay sensitivity, especially as a function of enzyme source.

In a particular embodiment, out of ten tests, the system or assay permits 9 true negative tests with 1 false negative.

Other such properties may include scale of testing, assay time, ease of use and collateral (healthcare worker) infections. In particular, accuracy is of the upmost importance as a false negative result could lead a wrong diagnosis or treatment when used to detect a target analyte in a biological sample.

In one embodiment, the systems and assays disclosed herein provides a result to the user within about 10 minutes or less from the after the addition of the biological (e.g., saliva or blood) sample, and more particularly about 5 minutes or less, about 2 minutes or less or about 1 minute or less. In a particular embodiment, the system permits the result to be provided to the user within about 1 to about 2 minutes.

In one embodiment, the systems and assays disclosed herein has a false positive rate of less than about 33%. In a particular embodiment, the false positive rate is about 32%, about 30%, about 28%, about 26%, about 24%, about 22%, about 20%, about 18%, about 16%, about 14%, about 12% about 10%, about 8%, about 6%, about 4% or about 2% or less.

In another embodiment, the systems and assays disclosed herein has a false negative rate of less than about 20%, about 18%, about 16%, about 14%, about 12% about 10%, about 8%, about 6%, about 4% or about 2% or less.

In one embodiment, the systems disclosed herein permits (with a 95% confidence interval) a 95% sensitivity and 95% specificity.

In another embodiment, the system disclosed herein permits a minimal target clinical sensitivity of about 90%, and optimal target sensitivity of about 98%; a minimal target specificity of about 90%, and an optimal target sensitivity >98%.

In one embodiment, the system disclosed herein permits improved disease diagnosis, monitoring, management or combinations thereof.

The sample and assays described herein may vary in format and detection strategy but share certain common elements as discussed below.

A. Sample

The sample utilized in the systems, assays and methods disclosed herein may vary.

In one embodiment, the sample is a biological sample. Biological samples a variety of sample types obtained from an individual including a clinical or non-clinical sample. The biological sample may vary and include, for example, sweat, saliva, tears, blood, serum, milk, urine, mucus, fecal matter, sebum, ocular fluid such as aqueous humor, respiratory droplets, pleural effusion, cerebral spinal fluid, semen, ejaculate, vaginal mucus, lymph fluid, ascites, peritoneal fluid, pericardial fluid, amniotic fluid, synovial fluid, intestinal fluid, cerumen, epidermal cells, white blood cells, nasal or nasopharyngeal specimens, blood or a combination thereof.

In a particular embodiment, the biological sample is saliva. Advantageously, the use of saliva as the biological sample eliminates the use of uncomfortable sample collection techniques and permits straightforward sample collection. Saliva is a viscous, dense, sticky fluid innately containing microorganisms like bacteria and fungi, intact human cells, cellular debris, and many soluble materials enzymes, hormones, antibodies, and other molecules.

Saliva specimens can be readily collected from a subject in any suitable manner and in certain embodiments, without the use of specialized equipment, e.g., by having the subject split into a vessel, the contents of which are then diluted and applied to the system or assay or alternatively, spit on the cassette or test strip directly. See, e.g., Navazesn M (1993). Methods for collecting saliva. Ann N Y Acad Sci 694:72-77. In other embodiments, the saliva can be processed (e.g., by centrifugation) to provide a cell-free fluid phase.

Blood specimens can be readily collected from a subject in any suitable manner and in certain embodiments, without the use of specialized equipment.

In another particular embodiment, the biological sample is not blood.

In another particular embodiment, the biological sample is not urine.

Biological samples can be derived from a subject (e.g., a human) using well known techniques such as venipuncture, lumbar puncture, fluid sample such as saliva or urine, or tissue biopsy and the like.

The volume of the biological sample may vary. In one embodiment, the volume of the biological sample is between about 1 μL, 10 μL, 20 μL, 50 μL, or 100 μL and about 2000 μL, more particularly about 100 μL, about 150 μL, about 200 μL, about 250 μL, about 300 μL, about 350 μL, about 400 μL, about 450 μL, about 500 μL, about 550 μL, about 600 μL, about 650 μL, about 700 μL, about 750 μL, about 800 μL, about 850 μL, about 900 μL, about 950 μL, about 1000 μL, about 1250 μL, about 1500 μL, about 1750 μL or about 2000 μL.

In another embodiment, the sample is an environmental sample. The environmental sample may vary an include, water, soil, wastes (liquids, solids or sludges including, for example, sewage) fuel, sediment, mud or the like. In certain embodiments, the environmental sample is a product of industry such as a food or beverage or raw materials utilized in producing the same.

In some embodiments, the system incorporates sample preparation (for instance, solvation, dilution and mixing) via components such as a collection chamber and/or fluidic design. Matrices on the strip may include any solvated material. Alternatively, sample preparation may be handled independent of the system and then added to the system.

In certain embodiments, the sample may have been manipulated or processed in some way following procurement but before testing for the analyte of interest. In particular, the sample may be diluted in a liquid medium to provide a diluted sample. The liquid medium used to dilute the sample may be, for example, include water, saline, cell-culture medium, or any solution and may contain any number of salts, surfactants, buffers, reducing agents, denaturants, preservatives, and the like. The sample may be diluted, for examples, 2×, 4× or 6× or more.

The pH of the sample may vary but in certain embodiments is between about 6.0 and about 8.0.

A solid sample may be dissolved in a liquid medium or otherwise prepared as a liquid sample to facilitate flow. In instances where biological cells or particles are used, the biological cells or particles may be lysed or otherwise disrupted such that the contents of the cells or particles are released into a liquid medium. Molecules contained in cell membranes and/or cell walls may also be released into the liquid medium in such cases.

In other embodiments, the sample may be mixed at least one reagent before being added to the assay, e.g., a capture agent, binding agent, second binding agent, and/or substrate.

In certain embodiments, the target analyte is not enriched or incubated prior to performing the diagnostic assay itself.

In certain embodiments, the sample is a raw sample, i.e., taken directly from the source and not otherwise processed before testing.

B. Target Analyte

The at least one target analyte detected by the systems, assays and methods disclosed herein may vary. In certain embodiments, the systems, assays and methods disclosed herein permit detection of two or more target analytes either simultaneously or sequentially, i.e., are multiplexed systems, assays or methods.

In certain embodiment, the target analyte may be associated with a normal healthy condition or apathogenic or otherwise altered physiological condition due to a disease or injury. In other embodiments, the target analyte is associated with an altered physiological condition and the testing permits monitoring of the progress of that condition or response to treatment.

In one embodiment, the target analyte is associated with an allergenic disease, infectious disease, autoimmune disease, cardiac disease, cancer or graft versus host disease.

In a particular embodiment, the target analyte is not glucose.

In one embodiment, the sample is a biological sample and the target analyte is a analyte selected from a microorganism such as a pathogenic microorganism (e.g., virus, bacterial, fungi, parasite or fungal spore) allergen, protein, peptide, nucleic acid, small molecule, hormone, steroid, co-factor, vitamin, metabolite or the like. In certain embodiments, the target analyte is the whole microorganism such as a whole virus.

In other embodiments, the target analyte is an antigen associated with the microorganism, e.g., a protein, a peptide, a polysaccharide, a toxin, a cell wall, a cell capsule, a viral capsule, a viral coat, a flagellum, a fimbria or pilus, a microorganism, a nucleic acid complexed to a protein or a polysaccharide, a lipid, a lipid complexed to a protein or a polysaccharide, a polynucleotide, a polypeptide, a carbohydrate, chemical moiety, or combinations thereof (e.g., phosphorylated or glycosylated polypeptides, etc.) Specifically, the target analyte may be a virus or portion of a virus wherein at least one polyclonal or monoclonal antibody or aptamer or protein for that virus or portion of a virus, either currently or becomes known.

In one embodiment, the virus is a DNA virus. For example, a single stranded or double stranded DNA virus.

In another embodiment, the virus is an RNA virus. For example, a single stranded or double stranded RNA virus.

Representative, non-limiting viruses that can be detected according to the systems, assays and methods disclosed herein include adenovirus, adeno associated virus, influenza, parainfluenza, cytomegalovirus, coronavirus, hepatitis (e.g., hepatitis A, hepatitis B, hepatitis C, hepatitis D), human immunodeficiency virus, avian influenza virus, respiratory syncytial virus (RSV), herpes simplex virus, Ebola virus, herpes simplex virus 1, herpes simplex virus 2, human papilloma viruses, Marburg virus, Lassa virus, pestivirus, porcine parvovirus, peudorabies virus, rotavirus, calicivirus, Epstein-Barr virus, human cytomegalovirus, human bocavirus, parvovirus B19, human astrovirus, Norwalk virus, coxsackievirus, measles virus, mumps virus, rubella virus or rotavirus. or canine distemper virus.

In a particular embodiment, the target analyte is a coronavirus, e.g., a whole coronavirus or coronavirus protein or peptide. Coronaviruses consist of a large and diverse family of enveloped, positive-sense, single-stranded RNA viruses. Every coronavirus contains four structural proteins, for example spike (S), envelope (E), membrane (M), and nucleocapsid (N) proteins. Among them, S protein plays the most important roles in viral attachment, fusion and entry.

In one embodiment, the target analyte is a coronavirus S protein or a fragment or epitope thereof. The S protein is a trimeric type-I transmembrane glycoprotein, which forms the characteristic corona of large protruding spikes on the virion surface and mediate binding to host cell receptors and fusion with the host cell membrane. In many coronaviruses, S is post-translationally cleaved into two subunits, designated S1 and S2, which trimerize and fold into a metastable pre-fusion conformation. The S1 subunit forms the "head" of the spike and contains two domains: an amino (N)-terminal domain (NTD) and a carboxy (C)-terminal domain (CTD), with the latter generally containing a receptor binding domain (RBD). The S2 subunit contains two heptad repeat (HR) regions. When S1 recognizes and binds to the corresponding host receptor, S2 undergoes a conformation change, extending itself from compressed form to a nail-like shape, termed as post-fusion state. This enables the viral envelope to fuse with the outer membrane and deposit the viral genetic material inside the cell. The life cycle of the virus then progresses to include biosynthesis, assembly and release.

In one embodiment, the target analyte is S1 or S2 and more particularly, the NTD, the RBD, CTD1, CTD2, S1/S2, S1/S2 cleavage site, S2', S2' cleavage site, fusion peptide, fusion peptide proximal region (FPPR), heptad repeat 1 (HR1), heptad repeat 1, central helix region (CHD), connector domain (CD, heptad repeat 2 (heptad repeat 2), transmembrane anchor (TM), cytoplasmic tail (CT or a combination thereof).

Coronavirus diversity is reflected in the variable S proteins, which have evolved into forms differing in their receptor interactions and their response to various environmental triggers of virus-cell membrane fusion. In particular, the RBD of the S protein is the most variable genomic part in the betacoronavirus group.

In another embodiment, the target analyte is a coronavirus nucleocapsid (N) protein or a fragment of epitope thereof. The N protein is characterized by three distinct and highly conserved domains: two structural and independently folded structural regions, namely the N terminal domain (NTD/domain 1) and C-terminal domain (CTD/domain 3), which are separated by a intrinsically disordered central region (RNA-binding domain/domain 2). In a particular embodiment, the target analyte is the NTD, the CTD or the RNA-binding domain of the N protein.

Four serologically distinct groups of coronaviruses have been described, i.e., alpha, beta (previously referred to as group 2), delta and gamma. Within each group, viruses are characterized by their host range and genome sequence. The alphacoronaviruses and betacoronaviruses infect only mammals, while the gammacoronaviruses and deltacoronaviruses primarily infect birds, although some of them can also infect mammals. Novel mammalian coronaviruses are now regularly identified. (Su et al., Trends Microbiol. 2016; 24: 490-502). Betacoronaviruses (Beta-CoV) of known clinical important to humans includes viruses of the A, B and C lineage and more particularly, the A lineage: OC43 (which can cause the common cold) and HKU1; the B lineage: LPH-CoV, SARS-CoV, SARS-CoV-2 (which causes the disease COVID-19) and SARS-CoV-n (where n is any integer); and C: MERS-CoV.

In one embodiment, the systems, assay and methods disclosed herein are directed to the detection of a betacoronavirus infection and more particularly, a A-lineage, B-lineage or C lineage coronavirus infection. These are viruses with a positive-sense single-strand RNA of around 32 Kb, encoding for multiple structural and non-structural proteins. The viral particles contain four main structural proteins: the spike, membrane, envelope protein, and nucleocapsid. The spike protein protrudes from the envelope of the virion and plays a pivotal role in the receptor host selectivity and cellular attachment. Betacoronaviruses have many similarities within the ORF lab polyprotein and most structural proteins; however, the spike protein and accessory proteins portray significant diversity. Mutations in the spike protein could change the tropism of a virus, including new hosts or increasing pathogenesis In a particular embodiment, at least one target analyte is a virus and more particularly, a coronavirus such as a betacoronavirus and even more particularly, SARS-CoV-1 or SARS-Cov-2.

In another particular embodiment, the systems, assays and methods disclosed herein are directed to the detection of a severe acute respiratory syndrome coronavirus 2 (SARS-CoV-2) infections. SARS-CoV-2 (also referred to as 2019-nCoV) was identified in January 2020 as the causative agent of Severe Acute Respiratory Syndrome 2, also referred to as Covid-19. Infections with the novel coronavirus quickly became widespread and in March 2020, the World Health Organization (WHO) declared Covid-19 as pandemic. The virus has, to date, infected more than 7 million people and killed more than 400,000 individuals. Individual living or working in high density and close contact (e.g., military personnel) are particularly at risk.

Clinical signs associated with SARS-CoV-2 include pneumonia, fever, dry cough, headache, and dyspnea, which may progress to respiratory failure and death. The incubation period for SARS-CoV-2 seems to be longer than for SARS-CoV and MERS-CoV, which have a mean incubation time of 5 to 7 days.

SARS-CoV-2 was sequenced and isolated by January 2020 (e.g., Zhou N. N Engl J Med., 382 (2020), pp. 727-733). Several sequences of SARS-CoV-2 have since been released. Similar to other coronaviruses, the spike (S) protein is the major glycoprotein on the SARS-CoV-2 virus surface. SARS-CoV-2 seems to have a receptor binding domain (RBD that binds with high affinity to ACE2 from humans, ferrets, cats and other species with high receptor homology. (Wan et al., (2020) J. Virol. https://doi.org/10.1128/JVI.00127-20).

The SARS-CoV-2 S1 RBD is 193 amino acids in length (N318-V510).

It has been reported that the SARS-CoV-2 S protein shares 76% amino acid sequence identity with the SARS-CoV S Urbani and 80% identity with bat SARSr-CoV ZXC21 S and ZC45 S glycoprotein. Sequence alignment for the interacting domain of SARS-CoV-2 (MN938384), Bat-CoV (MN996532 and MG772933) and SARS-CoV (NC004718). The RBD of SARS-CoV-2 differs largely from the SARS-CoV at the C-terminus residues.

The S1 subunit of SARS-CoV-2 contains a receptor-binding domain (RBD), while the S2 subunit contains a hydrophobic fusion peptide and two heptad repeat regions. S1 contains two structurally independent domains, the N-terminal domain (NTD) and the C-terminal domain (C-domain). Depending on the virus, either the NTD or the C-domain can serve as the receptor-binding domain (RBD).

In one embodiment, the systems, assays and methods disclosed herein permit detection of the S protein of SARS-CoV-2 or a subunit or fragment thereof, and more particularly, one or more epitopes of the S protein of SARS-Co-V-2, including, but not limited to the RBD, the S1 amino-terminal domain (S1-NTD), ORF3 (3a and 3b) and the accessory gene ORF8.

In one embodiment, the capture and binding agents bind the SARS-CoV-2 spike (S) protein using the human angiotensin converting enzyme (ACE) protein. In a particular embodiment, the ACE protein binds the receptor binding domain (RBD) of the S protein.

In one embodiment, the capture agent and detector agent bind different epitopes on the SARS-CoV-1 spike (S) protein. In a particular embodiment, at least one of the epitopes is within the receptor binding domain (RBD) of the S1 protein.

In one embodiment, one of the binding agents bind the SARS-CoV-1 spike (S) protein using the human angiotensin converting enzyme (ACE). In a particular embodiment, the ACE protein binds the receptor binding domain (RBD) of the S protein.

In one embodiment, the systems, assays and methods herein permit detection of whole virus, i.e., a SARS-CoV-2 particle.

In one embodiment, the systems, assays and methods herein permit detection of one or more epitopes of the N-terminal domain (NTD) and the C-terminal domain (C-domain) of SARS-CoV-2.

In one embodiment, the systems, assays and methods herein permit detection of one or more epitopes in the RBD of SARS-CoV-2 and more particularly, one or more epitopes residues within residues 319 and 510 of the RBD.

In a particular embodiment, the systems, assays and methods disclosed herein are directed to the detection of a SARS-CoV infection. SARS-CoV was identified in April 2003 as the pathogen responsible for Severe Acute Respiratory Syndrome (SARS) (Drosten et al., New Engl. J. Med. 2003; 348: 1967-1976). Clinically, SARS-CoV exhibits biphasic course, i.e., first high fever, parainfluenza syndrome followed by increasing respiratory distress. Droplets play a key role in transmission. Diagnosis is based on clinical picture and epidemiological data supported by positive serology, PCR or presence virus in cell culture. The consensus genomic sequence for SARS-CoV was published shortly thereafter, resembling most closely the group B betacoronaviruses (Marra et al., Science. 2003; 300: 1399-14040; Ruan et al., Lancet. 2003; 361: 1779-1785).

The SARS-CoV spike protein has been shown to consist of two functional domains, S1 (amino acids 12-680) and S2 (amino acids 681-1255) (Li et al., Science. 2005; 309: 1864-1868). The RBD is located within the S1 subunit and has been mapped to a fragment consisting of amino acids (aa) 318-510 in the S1 domain. (Wong et al., J Biol Chem. 2004; 279: 3197-3201).

In one embodiment, the systems, assays and methods disclosed herein permit detection of the S protein of SARS-CoV-2 or a fragment or epitope thereof, and more particularly, one or more epitopes of the S protein of SARS-CoV-2, including, but not limited to the RBD.

In one embodiment, the systems, assays and methods herein permit detection of one or more epitopes in the RBD of SARS-CoV-2 and more particularly, one or more epitopes residues within residues 318 and 510 of the RBD.

In one embodiment, the systems, assays and methods described herein permit detection of the N protein of SARS-CoV-2 or a fragment or epitope thereof.

In a particular embodiment, the systems and methods disclosed herein are directed to the detection of a Middle East Respiratory Syndrome-Coronavirus (MERS-CoV) infectious. MERS-CoV is a newly-emergent betacoronavirus which causes severe acute respiratory disease. It was first isolated in Saudi Arabia in 2012 (Zaki et al 2012, NEJM 367: 1814-1820) and since then has spread to about 18 countries with most of the cases in Saudi Arabia and United Arab Emirates. Clinical features of MERS-CoV infection in humans range from an asymptomatic infection to very severe pneumonia, with potential development of acute respiratory distress syndrome, septic shock and multi-organ failure resulting in death. The virus uses its spike protein for interaction with a cellular receptor for entry into a target cell.

It has been shown virus binds via the receptor binding domain of its spike protein to dipeptidyl peptidase 4 (DPP4) on human epithelial and endothelial cells (Raj et al 2013, Nature 495: 251-256). Lu et al 2013 have shown that MERS-CoV receptor binding domain consists of a core and a receptor binding subdomain that interacts with DPP4 (Lu et al 2013, Nature 500: 227-231).

The MERS-CoV spike protein is a 1353 amino acid type I membrane glycoprotein which assembles into trimers that constitute the spikes or peplomers on the surface of the enveloped MERS coronavirus particle. The protein has two essential functions, host receptor binding and membrane fusion, which are attributed to the N-terminal (S1, amino acid residues 1-751) and C-terminal (S2, amino acid residues 752-1353) halves of the S protein. MERS-CoV-S binds to its cognate receptor, dipeptidyl peptidase 4 (DPP4) via about 230-amino acid long receptor binding domain (RBD) present in the S1 subunit. Mou et al (2013) have shown in J. Virology (vol 87, pages 9379-9383) that the MERS-CoV RBD is located within the residues 358-588 of the spike protein. The amino acid sequence of full-length MERS-CoV spike protein is exemplified by the amino acid sequence of spike protein of MERS-CoV isolate EMC/2012 provided in GenBank as accession number AFS88936.1. The term "MERS-CoV-S" also includes protein variants of MERS-CoV spike protein isolated from different MERS-CoV isolates, e.g., Jordan-N3/2012, England-Qatar/2012, Al-Hasa_1_2013, Al-Hasa_2_2013, Al-Hasa_3_2013, Al-Hasa_4_2013, Al-Hasa_12, Al-Hasa_15, Al-Hasa_16, Al-Hasa_17, Al-Hasa_18, Al-Hasa_19, Al-Hasa_21, Al-Hasa_25, Bisha_1, Buraidah_1, England 1, Hafr-Al-Batin_1, Hafr-Al-Batin_2, Hafr-Al-Batin_6, Jeddah_1, KFU-HKU 1, KFU-HKU 13, Munich, Qatar3, Qatar4, Riyadh_1, Riyadh_2, Riyadh_3, Riyadh_3, Riyadh 4, Riyadh_5, Riyadh_9, Riyadh_14, Taif 1, UAE, and Wadi-Ad-Dawasir. The term "MERS-CoV-S" includes recombinant MERS-CoV spike protein or a fragment thereof.

In one embodiment, the capture and detection agents bind the spike protein, the membrane protein, the hemagglutinin protein, the envelope or envelope protein of common human coronaviruses, including types 229E, NL63, OC43, and HKU1.

In a particular embodiment, at least one target analyte is a virus and more particularly, a rhinovirus. In one embodiment, the first and second binding agents bind one of the 4 possible capsid proteins of the rhinovirus.

In a particular embodiment, at least one target analyte is a virus and more particularly, respiratory syncytial virus (RSV), parainfluenza (PIV), or H1N1.

In one embodiment, the first and second binding agents bind the fusion protein, the membrane protein, the hemagglutinin protein, the neuraminidase protein, the envelope or envelope protein of respiratory syncytial virus (RSV) parainfluenza (PIV), or H1N1.

In a particular embodiment, at least one target analyte is a virus and more particularly, human metapneumovirus.

In one embodiment, the capture and detection agents bind the fusion protein, the SH protein, the matrix protein, the glycoprotein, the envelope or envelope protein of human metapneumovirus.

In a particular embodiment, at least one target analyte is a virus and more particularly, human immunodeficiency virus (HIV).

In one embodiment, the capture and detector agents bind the MHC protein, the p17 matrix protein, the gp120 docking glycoprotein, the gp41 transmembrane glycoprotein, the envelope or envelope protein of human immunodeficiency virus (HIV).

In a particular embodiment, at least one target analyte is a virus and more particularly, Ebola virus.

In one embodiment, the capture and detector agents bind the glycoprotein, the matrix protein, the nucleoprotein, the envelope or envelope protein of Ebola virus.

In a particular embodiment, at least one target analyte is a virus and more particularly, Marburg virus.

In one embodiment, the capture and detector agents bind the glycoprotein, the VP40 matrix protein, the nucleoprotein, the envelope or envelope protein of Marburg virus.

In a particular embodiment, at least one target analyte is a virus and more particularly, Lassa virus.

In one embodiment, the capture and detector agents bind the glycoprotein 1, the glycoprotein 2, the large protein, the zinc protein, the stable signal peptide (SSP), the nucleoprotein, the envelope or envelope protein of Lassa virus.

In one embodiment, the capture and detector agents bind the TRAP protein, the SPECT protein, the MAEBL protein, a PPLP protein, a LSA protein, the STARP protein, the CS protein, the SALSA protein, the SPATR protein, the PxSR protein, or the PfEMP3 protein of malaria plasmodium.

In certain embodiments, the one or more target analytes or pathogens are found in biologic samples from animals other than humans, e.g., West-Nile virus and zoonotic pathogens in bats.

The target analyte is any protein or peptide wherein at least one polyclonal or monoclonal antibody or aptamer is known, either currently or becomes known.

Representative non-limiting targets include proteins such as: N-terminal pro-B-type natriuretic peptide (NTproBNP) [congestive heart failure]; insulin [diabetes]; glucagon [diabetes]; Autoantibodies (anti-dsDNA, anti-dsg1, ANA, etc.); Prostate-specific antigen (PSA) [cancer]; osteopontin (OPN) [arthritis and cancer]; Carcinoembryonic Antigen (CEA) [cancer]; Luteinizing hormone [pregnancy]; Follicular stimulating hormone [development]; Prolactin [cancer]; Human chorionic gonadotropin (hCG) [pregnancy and development]; Gluten [food allergies]; Wheat [food allergies]; Peanut [food allergies]; almond [food allergies]; casein and whey [food allergies]; sesame [food allergies]; eggs [food allergies]; tissue transglutaminase antibodies [celiac disease]; liver-type arginase [liver disease]; soluble liver antigen [liver disease]; mitochondrial 2 (M2) antigen [liver disease]; T3 triiodothyronine, ASA anti-sperm antibody, troponin I, T4 thyroxine, ACA anti-cardiolipin antibody, CKMB, TSH, AEA anti-endometrial antibody, FT3 free triiodo Thyronine, AOA anti-ovarian antibody, FT4 free thyroxine, ATB anti-trophoblast antibody, anti-TM thyroid microsomal antibody, ZP anti-zona pellucida antibody, anti-TG anti-thioglobulin antibody, anti-HCG antibody, human placental lactogen, anti-TPO thyroid peroxidase antibody, HCG, TOX toxoplasma antibody, FSH, AFP alpha fetal protein, CEA carcinoembryonic antigen, FPSA free prostate specific antigen, CMV cytomegalovirus antibody, PRO progesterone, ferritin, TOX-Ag toxoplasma circulating antigen, E2 estradiol, CA125, E3 estriol, CA153, CA199, HBsAg, NSE neuron specific enolase, HBsAb, CA50, HBeAg, β2 microblobulin, HBeAb, Coxsackie virus antibody, HBcAb, BGP bone Gla protein, D-Pyr deoxypyridinoline, vitamin D, insulin, PCIII type III procollagen, C-Peptide, type IV collagen, insulin antibody, LN laminin, glucagon, HA hyaluronic acid, GAD-AB glutamic acid Decarboxylase antibody, Fn fibronectin, Alpha-fetoprotein (AFP) human chorionic gonadotrophin like hormones e.g. HCG, LH, FSH, TSH; troponin I [myocardial infarction]; troponin T [myocardial infarction]; creatinine phosphokinase (CPK) [myocardial infarction]; MB isoenzyme (CPKMB) [myocardial infarction], myoglobin [myocardial infarction]; S100 protein such as S100B and enolase [cerebral ischemia]; 0-amyloid [Alzheimer's disease]; α-synuclein [Parkinson's disease]; 0-amyloid and myelin basic protein [multiple sclerosis]; albumin and liver enzymes [hepatitis C]; avidin; streptavidin; α1-antitrypsin and surfactant protein [chronic obstructive pulmonary disease]; α1-antitrypsin and surfactant protein [asthma]; Surfactant protein and elastase [adult respiratory distress syndrome]; rheumatoid factor, collagen, and elastase [autoimmune diseases]; albumin and elastase [organ failure]; Lipopolysaccharide binding protein [sepsis]; angiotensin and erythropoietin [eclampsia and pre-eclampsia]; calprotectin is the synonymous expression of "L1 albumen", "MRP 8/14", "cystic fibrosis (association) antigen (CFA)" and "calgranulin" [cardiac diseases and others]; oxidoreductases, transferases; kinases; hydrolases; lyases; isomerases; ligases; polymerases; cathepsins; calpains; amino-transferases such as, for example, AST and ALT, proteases such as, for example, caspases, nucleotide cyclases, transferases, lipases, enzymes associated with heart attacks, spike protein from SARS-CoV-2, and the like.

In certain embodiments, the analyte may be an antibody such as an nAb, IgA, IgE, IgG or IgM. For example a specific nAb, IgA, IgE, IgG or IgM is present in vivo due to a COVID infection. Antibodies arising from a disease or infection may be captured and detected.

In certain embodiments, the analyte may be a post-translationally modified protein (e.g., phosphorylation, methylation, glycosylation) and the capture component may be an antibody specific to a post-translational modification. Modified proteins may be captured with a multiplicity of specific antibodies and then detected with use of a specific-secondary antibody to a post-translational modification. Alternatively, modified proteins may be captured with an antibody specific for a post-translational modification and then detected with specific antibodies to each modified protein.

In certain embodiments, the target analyte is a hormone. The hormone may be a peptide hormone, an amino acid hormone, a steroid hormone or a eicosanoid hormone. Representative non-limiting hormones that can be detected by the systems, assays and methods herein include estrogen, progesterone, follicle-stimulating hormone (FSH), testosterone/DHEA, thyroid hormones, testosterone, cortisol, androstenedione or aldosterone.

In certain embodiments, the target analyte is a small molecule wherein at least one polyclonal or monoclonal antibody or aptamer for that small molecule is known or becomes known.

The small molecule target analyte may vary. In one embodiment, the target analyte is a biomarker, a drug (e.g., a therapeutic drugs and/or drugs of abuse), a heavy metal, a hormone, a growth promoter, a nutrient, a pesticide, a food additive or a toxin.

Any suitable therapeutic drug may be detected, e.g., a drug for the treatment of any disorder in humans or other mammals. In one embodiment, the drug to be detected is selected from an antibiotic, antifungal, antiparasitic, antiviral or anticancer drug.

In a particular embodiment, the drug to be detected is an antibiotic selected from the group consisting of penicillins, cephalosporins, macrolides, fluoroquinolones, sulfonamides, tetracyclines and aminoglycosides. In certain embodiments, the antibiotic is selected from the group consisting of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, avilamycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin clavulanate, ampicillin/sulbactam, piperacillin/tazobactam, ticarcillin/clavulanate, bacitracin, colistin, polymyxin b, ciprofloxacin, enoxacin, enrofloxacin, gatifloxacin, gemifloxacin, levofloxacin, lomefloxacin, moxifloxacin, monensin, nalidixic acid, norfloxacin, ofloxacin, sarafloxacin, spectinomycin, streptomycin, trovafloxacin, grepafloxacin, salinomycin, sparfloxacin, temafloxacin, bambemyin (flavomycin), mafenide, sulfacetamide, sulfachloropyridazine, sulfadiazine, silver sulfadiazine, sulfadimethoxine, sulfamethizole, sulfamethoxazole, sulfanilimide, sulfasalazine, sulfisoxazole, trimethoprim-sulfamethoxazole (tmp-smx), sulfonamidochrysoidine, demeclocycline, doxycycline, minocycline, oxytetracycline, tetracycline, clofazimine, dapsone, capreomycin, cycloserine, ethambutol(bs), ethionamide, isoniazid, pyrazinamide, erythromycin, rifampicin, rifabutin, rifapentine, streptomycin, arsphenamine, chloramphenicol, fosfomycin, fusidic acid, florfenicol, metronidazole, mupirocin, cefquinome, quinolones (e.g., fluoroquinolones), platensimycin, quinupristin/dalfopristin, neomycin, pirlimycin, ofloxacin, thiamphenicol, tigecycline, tilmicosin, tinidazole, and trimethoprim.

In a particular embodiment, the drug to be detected is an antifungal selected from the group consisting of allyamines, azoles, echinocandins and polyenes. In certain embodiments, antifungal drug is selected from the group consisting of amphotericin B, candicidin, filipin, hamycin, natamycin, nystatin, rimocidin, bifonazole, butoconazole, clotrimazole, econazole, fenticonazole, isoconazole, ketoconazole, luliconazole, metronidazole, miconazole, omoconazole, oxiconazole, sertaconazole, sulconazole, tioconazole, triazoles, tylosin, albaconazole, efinaconazole, epoxiconazole, fluconazole, isavuconazole, itraconazole, posaconazole, propiconazole, ravuconazole, terconazole, voriconazole, thiazoles, abafungin, amorolfin, butenafine, naftifine, terbinafine, anidulafungin, caspofungin, micafungin, ciclopirox, flucytosine, griseofulvin, tolnaftate, vancomycin and undecylenic acid.

In a particular embodiment, the drug to be detected by the systems and methods disclosed herein is an anti-parasitic drug. In certain embodiments, the drug is albendazole, avermectin or sulfaquinoxaline (SQX), In a particular embodiment, the drug to be detected by the systems, assays and methods disclosed herein is an antiviral agent. In certain embodiments, the antiviral drug is selected from the group consisting of attachment inhibitors, entry inhibitors, uncoating inhibitors, protease inhibitors, polymerase inhibitors, nucleoside and nucleotide reverse transcriptase inhibitors, nonnucleoside reverse-transcriptase inhibitors, and integrase inhibitors. In a particular embodiment, the antiviral drug is ribavirin.

In a particular embodiment, the drug to be detected by the systems and methods disclosed herein is an anti-cancer drug. In certain embodiments, the anticancer drug is methotrexate or paclitaxel, cisplatin, lenalidomide, ibrutinib, palbociclib, and enzalutamide. Other therapeutic drugs that can be detected according to the systems and methods disclosed herein include antipyretics, anesthetics, anthelminics, analgesics (e.g., acetaminophen, mycophenolic acid), anti-inflammatories (e.g., dipyrone), anti-coagulants, antihistamines, anticonvulsants, mood stabilizers, hormone replacements, oral contraceptives, stimulants, tranquilizers and statins.

Representative, non-limiting therapeutic drugs that can be detected by the systems and methods disclosed herein include 3-methylquinoxaline-2-carboxylic acid, LMG, and olaquindox.

Representative, non-limiting nutrients that can be detected by the systems and methods disclosed herein include biotin (vitamin B7), ferulic acid, folic acid and vitamin B12.

Representative non-limiting drugs of abuse that can be detected by the systems and methods disclosed herein include cannabinoids, clonazepam, cocaine, diazepam, dihydrochlorothiazide, diphenhydramine, ethyl glucuronide, LSD, heroin, harijuana, MDPV, nitrazepam, salicylic Acid, tramadol and venlafaxine.

In one embodiment, the target analyte is a biomarker. In one embodiment, the biomarker is associated with an infection, e.g., a viral infection. In one embodiment, the biomarker is selected from GM-CSF, Granzyme A, Granzyme B, IFN-$\alpha 2\alpha$, IFN-$\beta$, IFN-$\gamma$, IL-10, IL-1RA, IL-4, IL-5, IL-6, IL-7, IL-8, IL-9, IL-12p70, IP-10, I-TAC, MCP-1, MCP-2, MCP-4, MDC, MIP-la MIP-1$\beta$, TNF-$\alpha$, or VEGF-A.

Representative, non-limiting biomarkers that can be detected according to the systems, assays and methods disclosed herein include, without limitation, erythropoietin (EPO), ferritin, folic acid, hemoglobin, alkaline phosphatase, transferrin, apolipoprotein E, CK, CKMB, parathyroid hormone, cholesteryl ester transfer protein (CETP), cytokines, cytochrome c, apolipoprotein AI, apolipoprotein AII, apolipoprotein BI, apolipoprotein B-100, apolipoprotein B48, apolipoprotein CII, apolipoprotein CIII, apolipoprotein E, triglycerides, HD cholesterol, LDL cholesterol, lecithin cholesterol acyltransferase, paraxonase, alanine aminotransferase (ALT), asparate transferase (AST), CEA, HER-2, bladder tumor antigen, thyroglobulin, alpha-fetoprotein, PSA, CA 125, CA 19.9, CA 15.3, leptin, prolactin, osteoponitin, CD 98, fascin, troponin I, CD20, HER2, CD33, EGFR, VEGFA, etc.), drug (cannabinoid (e.g., tetrahydrocannabinol (THC), cannabidiol (CBD) and cannabinol (CBN), etc.), opioid (e.g., heroin, opium, fentanyl, etc.), stimulant (e.g., cocaine, amphetamine, methamphetamine, etc.), club drug (e.g., MDMA, flunitrazepam, gamma-hydroxybutyrate, etc.), dissociative drug (e.g., ketamine, phencyclidine, salvia, dextromethorphan, etc.), hallucinogens (e.g., LSD, mescaline, psilocybin, etc.), etc.), explosive (e.g., 2,4,6-trinitrotoluene (TNT) and hexahydro-1,3,5-trinitro-1,3,5-triazine (RDX), pentaerythritol tetranitrate (PETN), etc.), toxic chemical (e.g., tabun (GA), sarin (GB), soman (GD), cyclosarin (GF), 2-(dimethylamino)ethyl N, N-dimethylphosphoramidofluroidate (GV), VE, VG, VM, VP, VR, VS, or VX nerve agent), etc A biomarker may be differentially present at any level, but is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); or that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more. Alternatively, the differential presence of a biomarker can be characterized by a fold change in level including, for example, a level that is decreased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold; or that is increased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold. A biomarker is preferably differentially present at a level that is statistically significant (e.g., a p-value less than 0.05 and/or a q-value of less than 0.10 as determined using, for example, either Welch's T-test or Wilcoxon's rank-sum Test).

In one embodiment, the sample is an environmental sample and the target analyte is an analyte selected from the group consisting of toxins, pesticides, asbestos, pollutants, contaminants, organic compounds (e.g., petroleum hydrocarbon, polyaromatic hydrocarbon) or residues, perfluorinated compounds, organochlorine species, endocrine disruptors, pharmaceuticals, growth factors, detergents, triclosan, sweeteners, N-nitrosodimethylamine (NDMA), heavy metals (e.g., lead, cadmium), microbes, algal toxins, illegal drugs, flame retardants, antibacterials, hormones, mold, prions or nanomaterials.

Representative, non-limiting pesticides that can be detected by the systems and methods disclosed herein include acetamiprid, acetochlor, carbaryl, carbendazim/benomyl, chlorothalonil, chlorpyrifos, fenpropathrin, imidacloprid, parathion and pentachlorophenol. Representative, non-limiting hormones that can be detected by the systems and methods disclosed herein include steroid hormones (both natural and synthetic), e.g., estrogens (estrion, estradiol, estriol and derivatives thereof), androgens (testosterone, dihydrotestosterone, androstenediol, androstenedione, dehydroepiandrosterone (DHEA), dehydroepiandrosterone sulfate (DHEA-S) and derivatives thereof), progesterone (e.g., progesterone, 17-hydroxy-progesterone, pregnenolone, 17-hydroxy-pregnenolone and derivatives thereof), testosterone, cortisol (e.g., glucocorticoid, mineralcorticoid, cortisol, 11-deoxy-cortisol, corticosterone, 1-deoxy-corticosterone, 18-hydroxy-corticosterone, aldosterone and derivatives thereof) and melatonin.

Representative, non-limiting food additive that can be detected by the systems and methods disclosed herein include acrylamide; ALP; b acid; benzophenone, benzothiazine, BHT, BTZ. chrysoidine, DBP, dimethyl phthalate, enilconazole, erythrosine, Fluorescent Brightener KSN, MBT, melamine, rhodamine, Sudan I, Sudan Red, tartrazine and β-lactamase.

Representative, non-limiting fuel additives that can be detected by the system and methods disclosed herein include antiknock agents, such as ferrocene or toluene, or detergents, such as polybuteneamine or antioxidants, such as p-phenylenediamine. These may be sensed more readily by aptamer combinations not involving any antibodies.

In certain embodiments, the target analyte is important in an industry selected from agriculture, transportation or the food and beverage sector.

In some embodiments, the analyte of interest is a chemical or biological warfare agent. The target analyte may also be an analog, metabolite, and derivative of such chemical or biological warfare agent.

In certain embodiments, the assay is a multiplex assay, i.e., permits the detection of more than one target analyte. For example, the assay may detect two or more distinct target analytes, three or more distinct target analytes, four or more distinct target analytes or five or more distinct target analytes. In certain embodiments, the assay is an array suitable for us in detecting a multiplicity of distinct target analytes.

In one embodiment, the systems, methods and assays disclosed herein permit the simultaneous or sequential detection of detecting one or more of SARS-CoV. MERS-CoV. SARS-CoV-2, HCoV-OC43, HCoV-229E, HCoV-NL63, HCoV-HKU1, influenza A, influenza B, and RSV In certain embodiment, the multiplex assay detects two or more target analytes that are closely related, e.g., viral variants.

C. Assay (i) Format

The format of the assay may vary, whether it is a component of the system described herein or a stand-alone assay.

In one embodiment, the assay is a lateral flow assay. Generally, a lateral flow assay (LFA) runs a liquid sample along the surface of a solid support with a capture agent (e.g., antibody) that binds the target analyte (if present) to produce a signal, either directly or indirectly (e.g., by means of a labeled detection agent such as an antibody located within the assay, e.g., in a conjugate region). Conventional lateral flow assays include a strip (e.g., a nitrocellulose strip) but other substrates may be suitable such as, for example, dipstick, flow through device, or a microfluidic device.

In one embodiment, the assay is a lateral flow assay. In the test strip format, a fluid sample, containing or suspected of containing the at least one target analyte, is placed on a sample receiving zone. The target analyte becomes labeled after it contacts the test strip. The now-labeled target analyte of interest then flows (for example by capillary action) through the strip.

In a particular embodiment, the lateral flow assay (LFA) is composed of four parts: a sample pad, which is the area on which sample is dropped; a test region on a solid support (e.g., a polymer membrane) where reactions occur and an absorbent pad which reserves waste. The sample pad may be present on a fiber glass, quartz, or a cellulose substrate for receiving the sample. The absorbent pad (50) may include absorbent materials to facilitate collection such as cotton, polymers, Porex, paper, or may be empty.

In certain embodiments, the sample pad is the same pad as the test pad.

In certain embodiments, least one first binding agent (e.g., a capture agent or in certain embodiments, a first binding agent such as streptavidin) is bound to the solid support, e.g., in the form of test line. The area where the at least one first binding agent is bound is referred to as the immobilization region or test region.

In certain embodiments, the lateral flow assay also contains a conjugate pad comprising one or more labeled detection agents.

In certain embodiments, the lateral flow assay also contains one or more control regions comprising a control element to monitor performance of the assay or system.

In a particular embodiment, the sample is a liquid sample or has been diluted to provide a liquid sample. The liquid fluidic flow may be used to mix solutions, split solution direction, provide control sample detection, provide direction to analytical detection, or provide sample control detection.

Also provided is a vertical flow assay, wherein the sample flows vertically through the assay. The vertical flow sample may comprise one or more test regions and optionally, one or more control regions.

In one embodiment, the sample added to a sample pad region, a separation membrane is used to vertically separate out components from the biological sample leaving a filtered sample, wherein the filter sample then flows into the test region.

The assay comprises at least one capture agent and detector agent, but in certain embodiments, may comprise a first binding agent (e.g., streptavidin) to facilitate the production of test strips or other substrates that are target analyte agnostic. In certain embodiments, the first binding agent is cross-linked to reduce or prevent its dissociation from the test strip or other solid support.

In one embodiment, the assay is a competitive assay, where the capture agent is bound to a labelled target analyte. Un-labelled target analyte and the labelled target compete for binding to the capture agent and the amount of target analyte bound can be determined by the proportion of labelled target analyte detected. In other embodiments, the assay is a non-competitive assay.

In another embodiment, the assay is a two-binding agent assay. The two-binding agent assay includes a capture agent that binds to the target analyte and a detector agent that also binds to the target analyte. According to this embodiment, the capture and detector agents must recognize two non-overlapping epitopes of the target antigen so that when the first binding agent binds to the target analyte, the epitope recognized by the second binding agent is not obscured or altered. In one embodiment, the capture agent binds to a first epitope on the target analyte and the detector agent binds to a second epitope on the target analyte. As there are excess copies of the site on the target, both capture and detector agents can bind the target.

In another embodiment, the assay is a three-binding agent assay. The three-binding agent assay includes a capture agent that binds to the target analyte, a detector agent and a reporter agent, wherein the three binding agents form a detectable complex with the target analyte. horseradish peroxidase conjugate (e.g., an antibody-HRP conjugate).

In a further embodiment, the assay is four-binding agent assay. The four-binding agent assay includes a capture agent that binds to the target analyte and a detector agent that also binds to the target analyte, as well as a first binding agent that binds to a second binding agent, wherein the latter is conjugated to the capture agent (e.g., a biotinylated antibody). The first and seconding binding agents are a generic binding pair in the sense that neither binds specifically to the target agent. Rather, the first binding agent is immobilized on a solid support and the second binding agent, capture agent and detection agent are added to the system or assay by the user. According to this embodiment, the assay or test strip is generic with reference to the target analyte, i.e., analyte agnostic.

In a particular embodiment, the first binding agent contains multiple binding sites. A first binding site permits binding the second binding agent, while additional binding sites permit binding to a polymer (e.g., PEG) such that the first binding agent is cross-linked to one or more additional first binding agents to reduce or prevent dissociation of the first binding agents from the solid support.

In yet a further embodiment, the assay is a five-binding agent assay, wherein the capture agent is conjugate to a third binding agent to permit cross-linking to other capture agents to reduce or prevent dissociation.

(ii) Binding Agents

The systems and assays described herein include at least one binding agent and in certain embodiments, multiple binding agents. The binding agents are, in certain embodiments, specific to the target analyte (e.g., capture agents, detector agents) and in other embodiments, generic with respect to the target analyte (e.g., first and second binding agents).

The at least one binding agent may vary. In one embodiment, the binding agent (e.g., the capture agent, detection agent or genetic binding pair components) are selected from the group consisting of aptamers, antibodies, nanobodies, proteins, peptides, nucleic acids or a combination thereof.

In certain embodiments, the binding agent (e.g., the capture agent, the detection agent) is specific for an antigenic site on the target analyte.

In one embodiment, the capture and/or detector agent is an aptamer of approximately 10-15 kDa in size (20-45 nucleotides), binds its target analyte with at least micromolar affinity, and discriminates against closely related target analytes In one embodiment, the capture and/or detector agent is an aptamer of approximately 10-15 kDa in size (20-45 nucleotides), binds its target analyte with at least nanomolar affinity, and discriminates against closely related target analytes.

In a particular embodiment, the capture and/or detector agent is an aptamer wherein the Kd of aptamer to the target molecule is 10 nM or less, more preferable 5 nM or less and can be as low as 100 pM.

Antibodies suitable for use in the present invention include antisera, polyclonal antibodies, omniclonal antibodies, monoclonal antibodies, bispecific antibodies, humanized antibodies, chimeric antibodies, single chain antibodies, Fab fragments, F (ab') 2 Fragments, fragments generated by Fab expression libraries, epitope binding fragments of any of these, and complementarity determining regions (CDRs).

In one embodiment, the antibody is a monoclonal antibody. In some other embodiments, the antibody is a polyclonal antibody. In some examples, the polyclonal antibody is an affinity purified polyclonal antibody.

In certain embodiments, the nanobody is a particle, e.g., a magnetic particle. The size of the particular may vary but in one embodiment, is between about 100 nm and 100 nm and about 50,000 nm.

In another embodiment, the system or assay comprises micro-magnetic particles.

In a particular embodiment, the binding agent is produced via a fermentation process.

In one embodiment, the concentration of the detector and/or capture agents may range be millimolar, sub-millimolar, micromolar, nanomolar, picomolar, or femtomolar.

In certain embodiments, the detector agent is labeled, i.e., coupled to an enzyme or substrate. The efficiency or yield of enzyme labeling to detector agent may be greater than about 10%, greater than about 50%, greater than about 75%, or greater than about 90%. The purity of enzyme-labeled detector and/or capture agents may be greater than about 10%, greater than about 50%, greater than about 75%, or greater than about 90%.

In some examples, the enzyme is capable of changing color on exposure to a substrate.

In some examples, the substrate is capable of changing color on exposure to a reagent (such as an enzyme), respectively. As such, the detector agent may be labeled with a dye, a metal particle (e.g., gold), a compound capable of producing chemiluminescence or fluorescence. In alternative embodiments, the detector agent may be attached to a magnetic bead, a cellulose bead, a polymeric bead labeled with a dye, an affinity probe, and the like.

The affinity of the capture agent and/or detection agent for the target analyte may vary. In one embodiment, the capture agent and/or detection agent has a Kd for the target analyte from between about $10^{-3}$ to about $10^{-15}$ M.

In another embodiment, the capture and/or detection agent has a Kd for protein greater than about $10^{-10}$, greater than about $10^{-8}$, or greater than about $10^{-6}$ M.

In one embodiment, the capture agent and/or detection agent has a Kd for the target analyte of about 10 nM or less or about 5 nM or less.

In a particular embodiment, the capture agent and/or the detection agent has a Kd for the target analyte that is sub-nanomolar. In certain embodiment, the Kd is about 100 pM.

The affinity of the capture agent and the detection agent for the target analyte may differ. In a particular embodiment, the capture agent has a weaker affinity for the target analyte than the detection agent(s). In another particular embodiment, the capture agent has a stronger affinity for the target analyte than the detection agent.

In a particular embodiment, the affinity of capture agent for the first epitope is greater than the affinity of the detector agent on the second epitope. The ratio of the Kd of the first epitope to the Kd of the second epitope can range from 1:10,000 to 10,000:1.

In a particular embodiment, the affinity of the capture agent for the first epitope is greater than the affinity of the detector agent on the second epitope. The ratio of the Kd of the first epitope to the Kd of the second epitope can range from 1:10,000 to 10,000:1.

In a particular embodiment, the capture agent is an aptamer and the detector agent is an antibody and more particularly, a detectably labeled antibody.

In one embodiment, the capture agent is an aptamer and the detector agent is an antibody (e.g., a monoclonal antibody) and a third binding agent is present and specifically, an antibody (e.g., a monoclonal antibody).

In one embodiment, the first binding agent is an antibody and the second binding agent is an antibody (e.g., a monoclonal antibody) where the antibodies are the same or different or wherein the target for the antibodies in the same or different or wherein the third binding agent is an antibody for glucose oxidase.

In certain embodiments, the capture agent binds to a first site on the target analyte and the detector agent binds to a second (different) site of the target analyte or molecule wherein the third binding agent is an antibody for glucose oxidase.

In certain embodiments, the capture agent binds to a first site on the target analyte and the detector agent binds to a same site of the target analyte. As there are excess copies of the site on the target, both the capture agent and the detector agent can bind the target wherein the third binding agent is an antibody for glucose oxidase.

In certain embodiments, the binding agent (e.g., first binding agent or capture agent) is immobilized in or on a solid support, such as a bead or membrane, using any suitable method including, for example, depositing, spraying, soaking, immersing, pouring, or injecting capture agent on or within the assay membrane.

In one embodiment, the assay comprises a first binding agent immobilized on the solid support does not bind to the target analyte, but provided one component of a generic binding pair (e.g., streptavidin or avidin and biotin or a biotin analog or neutravidin and biotin or a biotin analog) that permits the strip to be manufactured in a manner that is not limited to a particular target analyte. According to this embodiment, the system or assay comprises a first binding agent, a second binding agent that binds to the first binding agent (collectively, a generic binding pair), a capture agent conjugated to the second binding agent and a fourth, labeled detector agent, wherein the capture and detection agents bind to the target analyte to create a detectable complex.

Generic binding pairs (e.g., first binding agents, second binding agents, third binding agents) include, for example, streptavidin and biotin or a biotin analog; avidin and biotin or a biotin analog; gold, silver, malamide, vinyl sulfones and thiol. In certain embodiments, thiol may be obtained from a cysteine amino acid (perhaps on a protein or antibody). Epoxide and thiol chemistries may also be employed to provide a generic binding pair, as well as silane and hydroxyl chemistry may also be utilized.

In certain embodiments, the system or method comprises multiple capture agent-detection agent binding pairs which bind to different epitopes on the same target analyte. For example, at least two, at least three, at least four, at least five or more such capture agent-detection agent binding pairs.

The liquid fluidic flow through the assay may be used to mix solutions, split solution direction, dilute the sample, provide control sample detection, provide direction to analytical detection, or provide sample control detection (iii) Solid Support The solid support may vary. In certain embodiments, the solid support comprises a strip or other substrate on which the reactions occur. The term "strip" or "test strip" also includes kits or devices where the "strip" has different dimensions and may be referred to as a "card". In certain embodiments, the strip has the dimensions of a bow-tie.

The test strip may include an insertion portion and an exposed portion. The exposed portion of the test strip can be arranged to accept a biological sample (e.g., saliva, blood) from a subject.

The strip or substrate may be made from any suitable material. In certain embodiments, the membrane is selected from the group consisting of polymer (e.g., a hydrogel), metal, glass-fiber or ceramic membranes, cellulose, nylon, cross-linked dextran or various chromatographic papers.

In one embodiment, the substrate is selected from nitrocellulose (e.g., in membrane or microtiter well form), polyvinylchloride (e.g., sheets or microtiter wells), polystyrene latex (e.g., beads or microtiter plates), polyvinylidine fluoride, diazotized paper, glass fiber membranes, nylon membranes, activated beads or magnetically responsive beads.

In one embodiment, the substrate is an anionic polymer such as a nitrocellulose membrane. In other embodiments, the substrate is sulfonated tetrafluoroethylene, poly(acrylic acid), or poly(2-acrylamido-2-methyl-1-propanesulfonic acid) (polyAMPS).

The strip or other substrate may be patterned regions comprising, for example, different materials, textures, hydrophobicities or hydrophilicities.

In a particular embodiment, the assay comprises a cross-linked hydrogel containing a capture agent (e.g., aptamer or antibody) or first binding agent of a generic binding pair (e.g., streptavidin). The cross-linked hydrogel may be present on or in the test strip.

The assay may comprise one of more functional zones, which are preferably distinct and not overlapping. These may include one or more tests zones or one or more control zones.

In certain embodiments, the strip comprises one or more channels selected from the group consisting of split channels, divided channels, parallel channels or adjoining channels.

In some examples, the channels can be of different lengths, varying materials or textures, geometric features, recessed features, patterned features, or recessed chambers.

In a particular embodiment, the membrane also collects the biological sample(s) and provides a sink area to flow the sample from one location on the membrane to another.

The assay may be a multiplex assay, i.e., permits the detection of two or more target analytes. In particular, the strip may have one or more test zones, each comprising at least one binding agent (e.g., a capture agent, a first binding agent of generic binding pair) capable of generating a signal directly or indirectly in response to the presence of the specific target analyte.

In other embodiments, multiple binding agents (e.g., capture agents) may be present within the same test zone, to permit detection of multiple targets analytes within a common test zone.

In some regions, the test zone may comprises a test region or test line "T." The detection zone may further comprise a control region or control line "C.

In a particular embodiment, the system comprises a second strip, wherein the first strip and the second strip permit detection or different target analytes.

In one embodiment, color change is used to determine the concentration of the at least one target analyte.

In a particular embodiment, an intermediate semi quantitative, colorimetric assay is providing comprising a gradient (deposition density) of the first binding agent (e.g., streptavidin) on a solid support (e.g., polymer membrane) in order to provide a range or concentration of the bound target analyte.

In some embodiments, the strip can be adapted or fabricated for colorimetry. In these examples, electrodes may not be utilized (e.g., the working electrode region may not be provided).

In a particular embodiment of the strip, the test region resides on top of at least one electrode that provides a chamber that is used to determine current and analyte concentrations.

In another embodiment of the strip, the electrode is located at, above or below at least one electrode.

In one embodiment, the test strip includes at least one test site and two or more electrodes (e.g., working and reference electrodes) and a means for making connection between the electrodes and the meter.

In a particular embodiment, the test site is located between two electrodes.

In certain embodiments, the at least one binding agent (e.g., capture agent, first binding agent of a generic binding pair) is bound to the electrode. Direct electrode functionalization can be accomplished by any suitable method, for example, thin-film dry-phase-inversion method using nitrocellulose, methylcellulose, ethylcellulose, hydropropyl ethylcelllulose, or any solid immobilization structure dissolved or suspended in solvent, and or water. Deposition on the electrode may precede further modification with the at least one binding agent or may be concomitant through co-deposition the at least one binding agent.

In certain embodiments, the strip comprises two or more electrodes or three or more electrodes. In a particular embodiment, the strip comprises a first set of two or more electrodes and a second set of two or more electrodes in order to permit positive and negative controls.

Any suitable electrode may be utilized. In one embodiment, the electrode is a carbon, iron, palladium, platinum or gold electrode. In another embodiment, the electrode is a (semi-) conductive solid.

In certain embodiment, the at least one electrode is coated with a mediator. Representative, non-limiting mediators include Prussian blue, platinum, ferricyanide, hexacyanoferrate III/hexacyanoferrate II, 1,10-phenanthroline quinone, quinoneimine/phenylendiamine, or an osmium-based mediator.

In a particular embodiment, the electrode is carbon or carbon coated with Prussian blue or platinum.

In a particular embodiment, the electrode(s) is porous.

In a particular embodiment, the electrode(s) is interdigitated.

In certain embodiments, the at least one electrode is associated with a gel, e.g., coated with a gel, wherein the sugar (e.g., glucose) is present within the gel.

In a particular embodiment, a binding agent (e.g., a first binding agent, a capture agent) is incorporated into the carbon-based electrode or bound to a gold electrode.

In certain embodiments, the strip or solid support plugs into a detection device.

The free electrons can be moved through a circuit when a voltage is applied between the two electrodes. Each enzyme and mediator molecule can repeat this transfer again and again, if necessary. The amount of charge that moves through the circuit will be representative of the glucose level in the system which is reflective of the analyte concentration in the sample.

In a particular embodiment, the glucose oxidase is used as enzyme and the electrochemical reaction that occurs is shown below:

$$\text{Glucose} + O_2 \rightarrow D\text{-glucono-}1,5\text{-lactone} + H_2O_2$$

This oxidation reaction produces a current flow. The amplitude of this current is directly related to the concentration of blood glucose. Glucose oxidation by GOx result in o-glucono-o-lactone. $H_2O_2$ reduction at Prussian Blue (PB) film is measured by electron transferred from working electrode. In certain embodiments, the current is continuous, as opposed to leveled off.

In one embodiment, the test region resides on below an optical chamber for visualization of a color change and the change in color is used to determine analyte concentrations.

In a particular embodiment, the strip may be laminated or housed within a cassette, e.g., a disposable cassette.

In some embodiments, the cassette does not include a glucose pod for glucose storage or delivery.

In a particular embodiment, the strip is part of disposable (s) that contain a waterproof barrier, a waterproof base material, e.g., polyethylene terephthalate (PET).

In one embodiment, the test region may include bowtie structure to adhere membrane material underneath a water-proof barrier.

The cassette can include one or more of a reagent chamber, a channel for sample collection material, one or more microfluidic channels, and/or a working electrode region. The cassette can include a waste pod for waste storage. In some examples, the cassette can include a hinge configured to place the cassette in an open and a closed position. The hinge can actuate between the open and the closed position. In the open position, a sample can be in fluid communication with the sample collection material. The channel can comprise a proximal end with saliva sample collection material.

The cassette comprising the hinge in the closed position can substantially seal a sample in the cassette. In some embodiments, the hinge placing the cassette in the closed position operates to substantially prevent the cassette from being opened (e.g., the hinge can operate in a non-reversible manner).

In one embodiment, the reagents (e.g. the binding agents) utilized in test strip are storage-stable. In certain embodiments, the reagents for use with the test strip are freeze-dried to extend the shelf-life.

The test strip typically includes layers of conductive and non-conductive constituents disposed upon each other to produce a sensor structure.

In one embodiment, the test strip comprises a base substrate, a conductive layer, an insulating layer, a reagent layer, an adhesive layer, a hydrophilic (e.g., nitrocellulose) membrane to which the first binding agent (e.g., aptamer) is attached to capture the target analyte (e.g., antigen), a freeze-dried detectably labeled second binding agent (e.g., Ab-GOx) and glucose, and a top layer.

In another embodiment, the test strip comprises a base substrate, a conductive layer, an insulating layer, a reagent layer, an adhesive layer, a hydrophilic (e.g., nitrocellulose) membrane to which the first binding agent (e.g., aptamer) is attached to capture the target analyte (e.g., antigen) and freeze-dried glucose, the labeled second binding agent (e.g., Ab-GOx) is added to the biological sample containing the target analyte.

The base substrate serves as a matrix for the plurality of constituents that are stacked on top of one another and comprise the functioning sensor. This base constituent can be made of a wide variety of materials having desirable qualities such as dielectric properties, water impermeability, air impermeable, and hermeticity. Some materials include metallic, and/or ceramic and/or polymeric substrates or the like.

The conductive layer is disposed upon the base substrate, wherein the conductive layer that includes at least one electrode (e.g., one, two or three electrodes) comprising a conductive material for contacting an analyte or its byproduct (e.g. oxygen and/or hydrogen peroxide) to be assayed. The one or more electrodes may include one or more working electrodes and one or more counter, reference, and/or counter/reference electrodes.

The electrodes may be screen-printed electrodes, e.g., screen printed using conductive carbon inks. The materials used may vary. Conductive ink compositions useful the glucose sensor system of the invention include, but are not limited to a silver, carbon, or blended conductive ink. Examples of inks useful to print the working electrode include, but are not limited to, carbon, platinum, carbon/platinum, carbon nanotubes, or other conductive material suitable for the detection of peroxide in the sample.

The electrodes used and the sensitivity required generally dictates the enzyme chemistry that can be employed. For example, a second binding agent linked to glucose oxidase requires excess glucose to detect an analyte in the sample.

A "working electrode" is an electrode at which analyte is electrooxidized or electroreduced with or without the agency of a redox mediator. The working electrode can measure an increase or decrease in current in response to exposure to a stimuli such as the change in the concentration of the target analyte or molecule or its byproduct. The electrodes provide a detectable signals in the presence of variable concentrations of molecules such as hydrogen peroxide or oxygen.

In addition to the working electrode, the conductive layer may also include a reference electrode (RE) or a combined reference and counter electrode (also termed a quasi-reference electrode or a counter/reference electrode).

In one embodiment, the electrode providing a minimum sensitivity of at least about 50 micromolar glucose concentration and a noise level of less than about 100 nA to 0.5 nA per square millimeter.

The insulating layer may be a thin film of insulative (e.g., electrically insulative or water impermeable) material including poly(vinyl chloride), polyethylene, polypropylene, aromatic and aliphatic polyurethenes, poly(butylene terapthalate), polybutadiene, silicone rubbers, thiol-ene copolymers, or poly(ethylene-co-vinyl acetate) In certain embodiments, the reagent layer contains a mediator for ease of exchange of electrons. In one embodiment, the reagent layer includes a binder, silica, ferricyanide, ferricyanide, 1, 10-phenanthroline Quinone, or an osmium-based mediator.

The adhesive layer may be an acrylic copolymer, including poly(ethyl acrylate), poly(cyanoacrylate), poly(butyl acrylate), poly(2-ethylhexyl acrylate), and urethane acrylate copolymers.

The hydrophilic membrane may be comprised of an anionic hydrophilic copolymer, including nitrocellulose, sulfonated tetrafluoroethylene, poly(acrylic acid), or poly(2-acrylamido-2-methyl-1-propanesulfonic acid (polyAMPS). The membrane may be coated with streptavidin-NC and a first binding agent (e.g., a biotinylated aptamer) attached thereto to serve as a capture agent for the target analyte or molecule.

In a particular embodiment, the cassette or test strip includes a base substrate, typically made of PET; a conductive layer which includes three electrodes [8]; an insulating layer exposing only part of the electrode where we will drop the sample to be tested [6]; a reagent layer containing mediator for ease of exchange of electrons; [6] an adhesive layer; a hydrophilic nitrocellulose membrane, proximal membrane containing first binding agent (e.g., aptamer) to capture the target analyte (e.g., antigen) (would sit on 6 if 6 not directly functionalized) and freeze dried glucose and the distal end is the paper sink (5); (G) freeze-dried Ab-GOx; (4) top layer.

In a particular embodiment, the cassette or test strip includes (A) base substrate; (B) a conductive layer which includes two electrodes; (C) insulating layer exposing only part of the electrode where the sample to be tested is dropped; (D) reagent layer containing mediator for ease of exchange of electrons; (E) adhesive layer; (F) hydrophilic nitrocellulose membrane, proximal membrane containing first binding agent (e.g., aptamer) to capture the target analyte (e.g., antigen) and freeze dried glucose and the distal end is the paper sink (13); (G) freeze-dried Ab-GOx; (H) top layer.

According to this embodiment, the base substrate is polyester and an acrylic coating is applied to improve the ink adhesion. Using a CAD model of electrode mask, the mask is laser cut onto the base substrate. The electrodes are then screen printed using conductive carbon inks (Ercon Inc) followed by an insulation layer (Ercon Inc, Insulayer ink). The two working electrodes will have a surface area of 0.6 mm$^2$ each, and the reference electrode will have 1.2 mm$^2$. The reagent layer is the mediator layer and will consist of a binder, silica, and ferricyanide. This layer is screen printed for two cycles over the working electrodes. The adhesive layer on top will be an acrylic copolymer, the hydrophilic membrane will be a nitrocellulose membrane with streptavidin-NC, and bound biotinylated aptamer to capture the viral antigen. The top layer may be PET, with a small clear portion to see the sample movement on the strip. The overall dimensions will be the similar as described in the patent to ensure compatibility with Lifescan's reader or can be altered to be compatible with other commercial glucometers.

In one embodiment, before the addition of freeze-dried bio reagents, and aptamer immobilization, dropcast GOx is directly dropcast onto the working electrode.

In certain embodiments, the test strip components may be pre-blocked in order to reduce or eliminate non-specific binding by any suitable blocking agent. Non limiting examples of coating materials are protein, acryl amide, synthetic polymer and polysaccharides. In one embodiment, BSA is utilized as a blocking agent. In one embodiment, denatured BSA is utilized as a blocking agent. In another embodiment, milk protein, TWEEN, or other surfactant is utilized as a blocking agent. In another embodiment, BSA, milk protein, casein, Triton, SDS, TWEEN, IGEPAL, or other surfactant(s) is utilized as a blocking agent.

In certain embodiments, the system permits a low signal to noise ratio, e.g., limits transient non-glucose related signal noise. The composition of the base layer, the method used for depositing the electrodes, the electrode configuration, the electrode materials, the enzyme chemistry used and other design factors all contribute to the noise of the system.

In one embodiment, the strip has a shelf life of more than 1 year or more than two years, or more than three years.

(iv) Labels and Detection Systems

The one or more binding agents (e.g., detection agent) may be associated with a label. The label can be linked directly to the binding agent (e.g., by a covalent bond) or the attachment can be indirect (e.g., using a chelator or linker molecule).

In a particular embodiment, the detection binding agent is conjugated to a label.

In certain embodiments, the label is attached directly to the capture agent, enabling direct detection.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, colloidal gold, and combinations thereof.

In some embodiments, the label is an enzyme, such as a redox enzyme, and the at least one target analyte is detected by detecting a product generated by the enzyme. Suitable enzymes include, without limitation, oxidases, dehydrogenases, amylases and invertases.

In one embodiment where the label is an enzyme, the enzyme can react with a substrate for that enzyme such that a colored, fluorescent, or chemiluminescent substance is produced from the substrate after reaction with the enzyme label. In a particular embodiment, the colored substrate is selected from o-phenylenediamine (OPD), 3,3',5,5'-tetramethylbenzidine (TMB), 3,3'-diaminobenzide tetrahydrochloride (DAB), 2,2'-azino-bis(3-ethylbenzthiazoline-6-sulphonic acid) (ABTS), and the like.

In a particular embodiment, the enzyme is an oxidase. Representative, non-limiting oxidases include saccharide oxidases (e.g., glucose oxidase, galactose oxidase, lactate oxidase, and glucose-6-phosphate dehydrogenase), cellulobiose oxidase, monoamine oxidase, cytochrome P450 oxidase, NADPH oxidase, heterocyclic oxidases (e.g., uricase and xanthine oxidase), L-gulonolactone oxidase, laccase, lysyl oxidase, polyphenol oxidase, sulfhydryl oxidase and ascorbic acid oxidase.

In certain embodiments, the enzyme is a dehydrogenases or oxidoreductases (e.g., D-glucose:D-fructose oxidoreductase). Representative, non-limiting enzymes include acetaldehyde dehydrogenase; aldehyde dehydrogenase, alcohol dehydrogenase, delta12-fatty acid dehydrogenase, glutamate dehydrogenase (an enzyme that can convert glutamate to α-Ketoglutarate and vice versa), lactate dehydrogenase, pyruvate dehydrogenase, fructose dehydrogenase, sucrose dehydrogenase, glucose dehydrogenase, glucose-6-phosphate dehydrogenase, glyceraldehyde-3-phosphate dehydrogenase, sorbitol dehydrogenase, isocitrate dehydrogenase, alpha-ketoglutarate dehydrogenase, succinate dehydrogenase, malate dehydrogenase, yellow enzyme, glutamate dehydrogenase, glycerol 1-phosphate dehydrogenase.

In one embodiment, the enzyme is horseradish peroxidase (HRP) or catalase.

In one embodiment, the enzyme is selected from PQQ-Glucose Dehydrogenase, NAD-Glucose Dehydrogenase and FAD-Glucose Dehydrogenase.

In one embodiment, an alkaline phosphatase/NBT-BCIP (4-nitro blue tetrazolium chloride and 5-bromo-4-chloro-3-indolyl-phosphate) detection system is utilized.

In one embodiment, an alkaline phosphatase detection system can be used with the chromogenic substrate p-nitrophenyl phosphate, which yields a soluble product readily detectable at 405 nm.

In one embodiment, two or more labels are utilized. In certain embodiments, each label (e.g., a first label linked to a capture agent, a second label linked to a detection agent) generates a detectable signal and the signals (e.g., a first signal generated by the first label, a second signal generated by the second label, etc.) are distinguishable. In some embodiments, the two or more labels comprise the same type of agent (e.g., a first label that is a first fluorescent agent and a second label that is a second fluorescent agent). In some embodiments, the two or more labels (e.g., the first label, second label, etc.) combine to produce a detectable signal that is not generated in the absence of one or more of the labels.

In some embodiments, at least two, at least three or at least four binding agents (e.g., capture agents, detection agents, first and second binding agents of a generic binding pair) are each labeled with an enzyme (e.g., a first binding agent labeled with a first enzyme, a second binding reagent labeled with a second enzyme, etc.), and each binding agent that is labeled with an enzyme is detected by detecting a product generated by the enzyme. In some embodiments, all of the binding reagents are labeled with an enzyme, and each enzyme-labeled binding reagent is detected by detecting a product generated by the enzyme.

In some embodiments, two or more labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase.

Various methods can be used to bind these labels covalently to the binding agent. For example, coupling agents such as dialdehydes, carbodiimides, dimaleimides, bis-imidates, bis-diazotized benzidine, and the like may be used to tag the binding agent with such labels.

In one embodiment, the enzyme label may be conjugated directly to a binding agent that detects the target analyte (capture agent) or introduced through a secondary binding agent (detection agent) that binds to the capture binding agent. It may also be conjugated to a protein such as streptavidin if capture agent is biotin labelled.

In a particular embodiment, the assay utilizes a dual labeling strategy that includes a first enzyme label such an oxidase (e.g., glucose oxidase) and a second enzyme label such as an oxidoreductase (e.g., HRP). According to this embodiment, the enzyme catalyzes the oxidation of the substrate to form hydrogen peroxide, which is then quantified by enzymatic reaction with horseradish peroxidase and a dye such as 3,3',5,5'-Tetramethylbenzidine or TMB through a change in color. As the amount of glucose in the biological sample is in excess and, added for the detection, the quantification is for the target analyte.

In a particular embodiment, the detector agent is an antibody. In one embodiment, the antibody is combined or linked with an enzyme (e.g., glucose oxidase) in a fixed ratio of whole number (e.g., 2 enzymes to 1 antibody or 3 enzymes to 1 antibody or 4 enzymes to 1 antibody).

Figure 2:
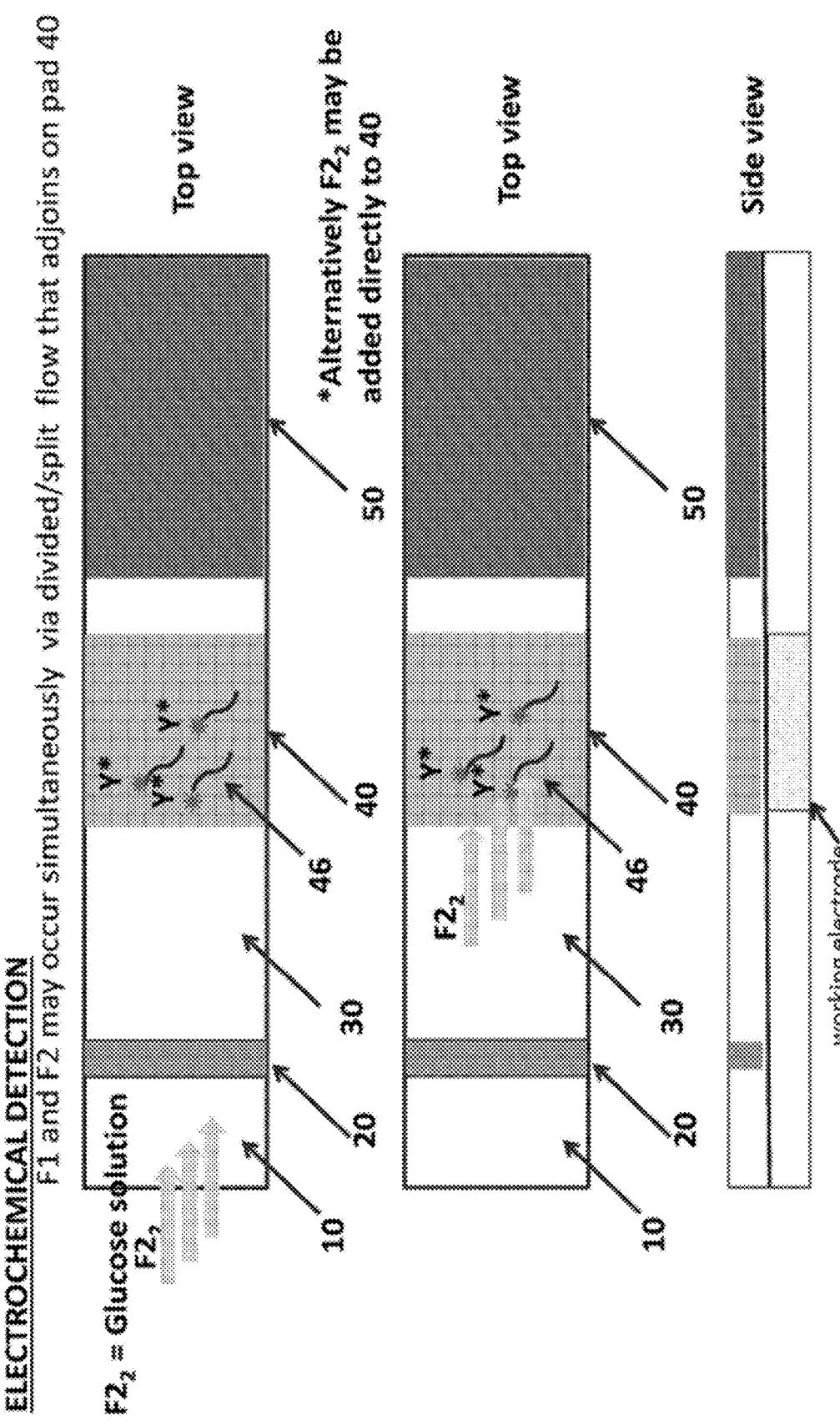
FIG. 2 shows a schematic top view procedural flow chart method for qualitative or quantitative detection of target analyte via electrochemical means. PB is Prussian Blue.
Figure 3A:
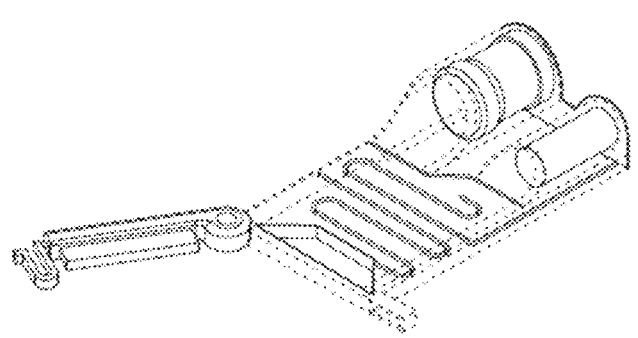
FIG. 3A and FIG. 3B show a prototype strip cartridge design that can be used in conjunction with an electrochemical reader.
Figure 3B:
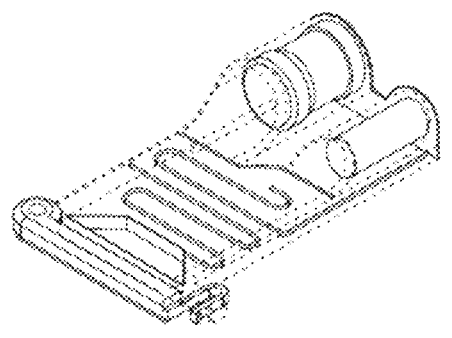
Figure 3C:
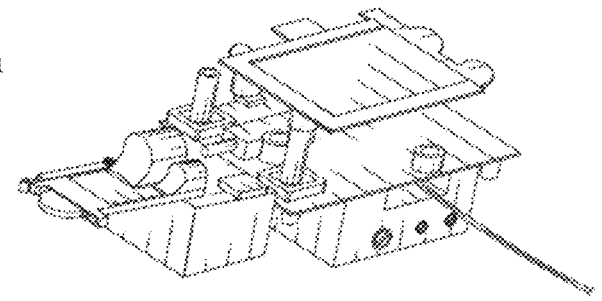
FIG. 3C shows an electrochemical reader.
Figure 4:
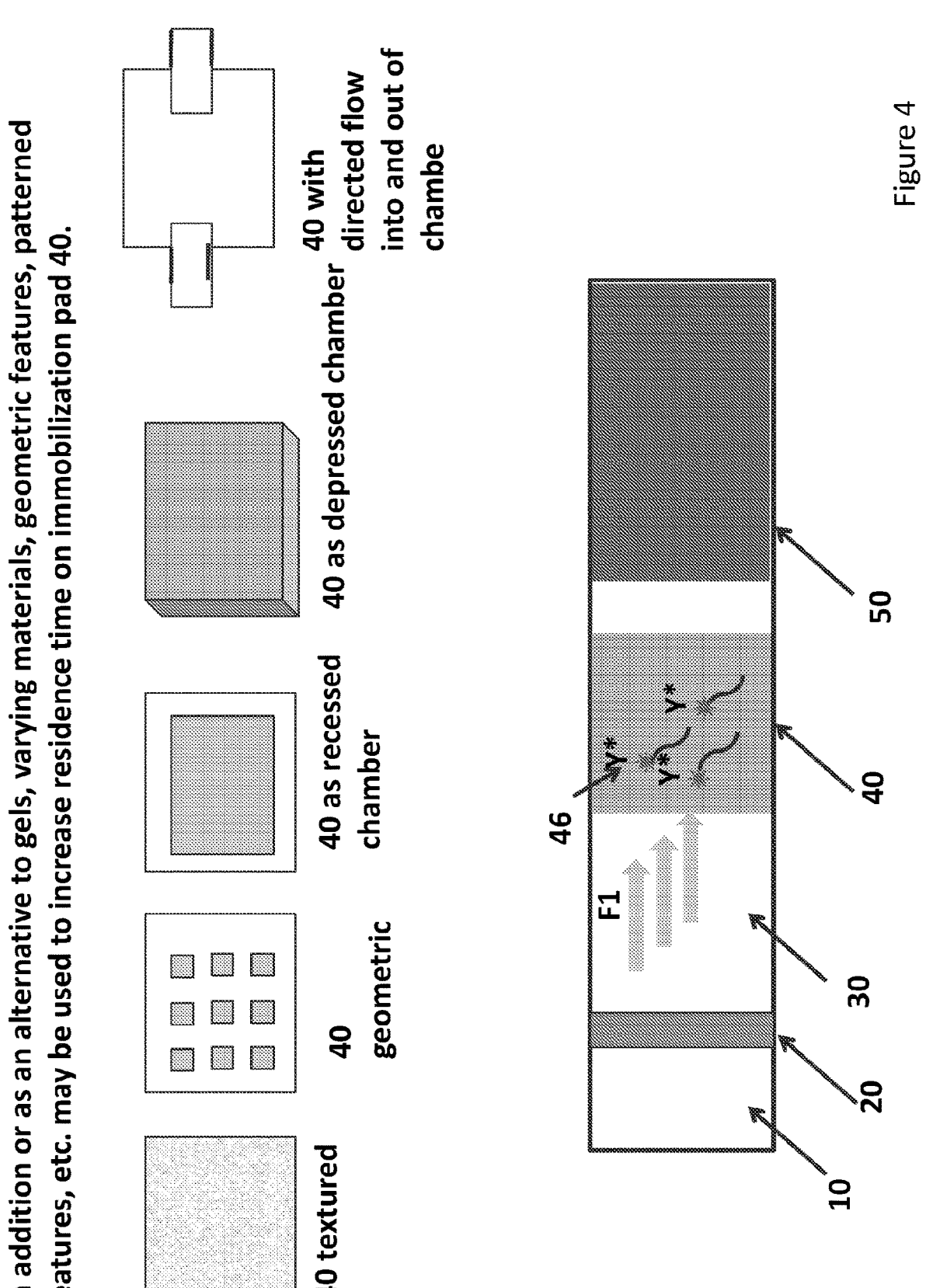
FIG. 4 includes materials and features that may be used to modify residence time.
Figure 6:
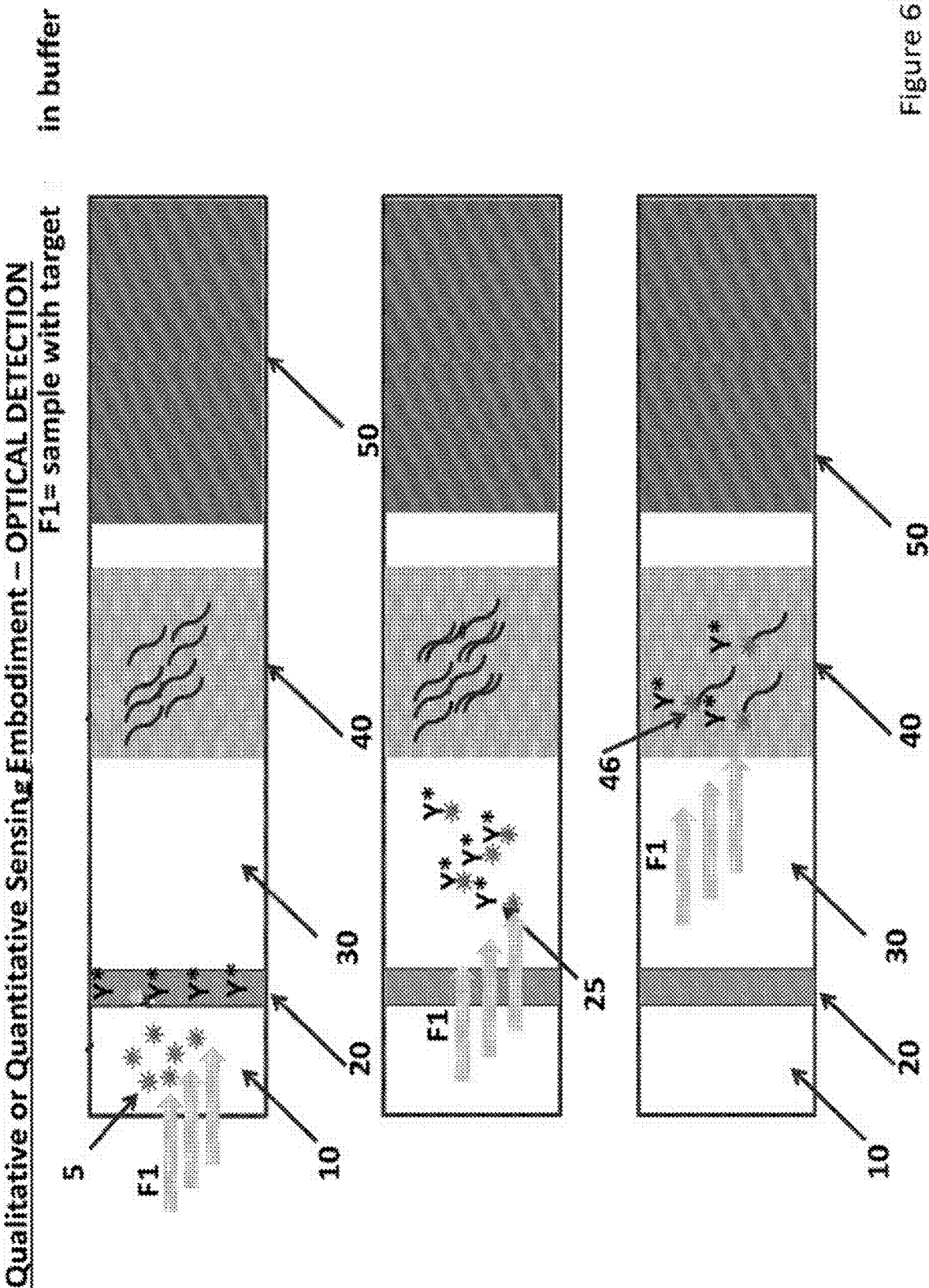
FIG. 6 shows a schematic top view procedural flow chart method for addition of target analyte in a sample applied to a strip with embedded chemistries which affords binding in a region of interest.
Figure 7:
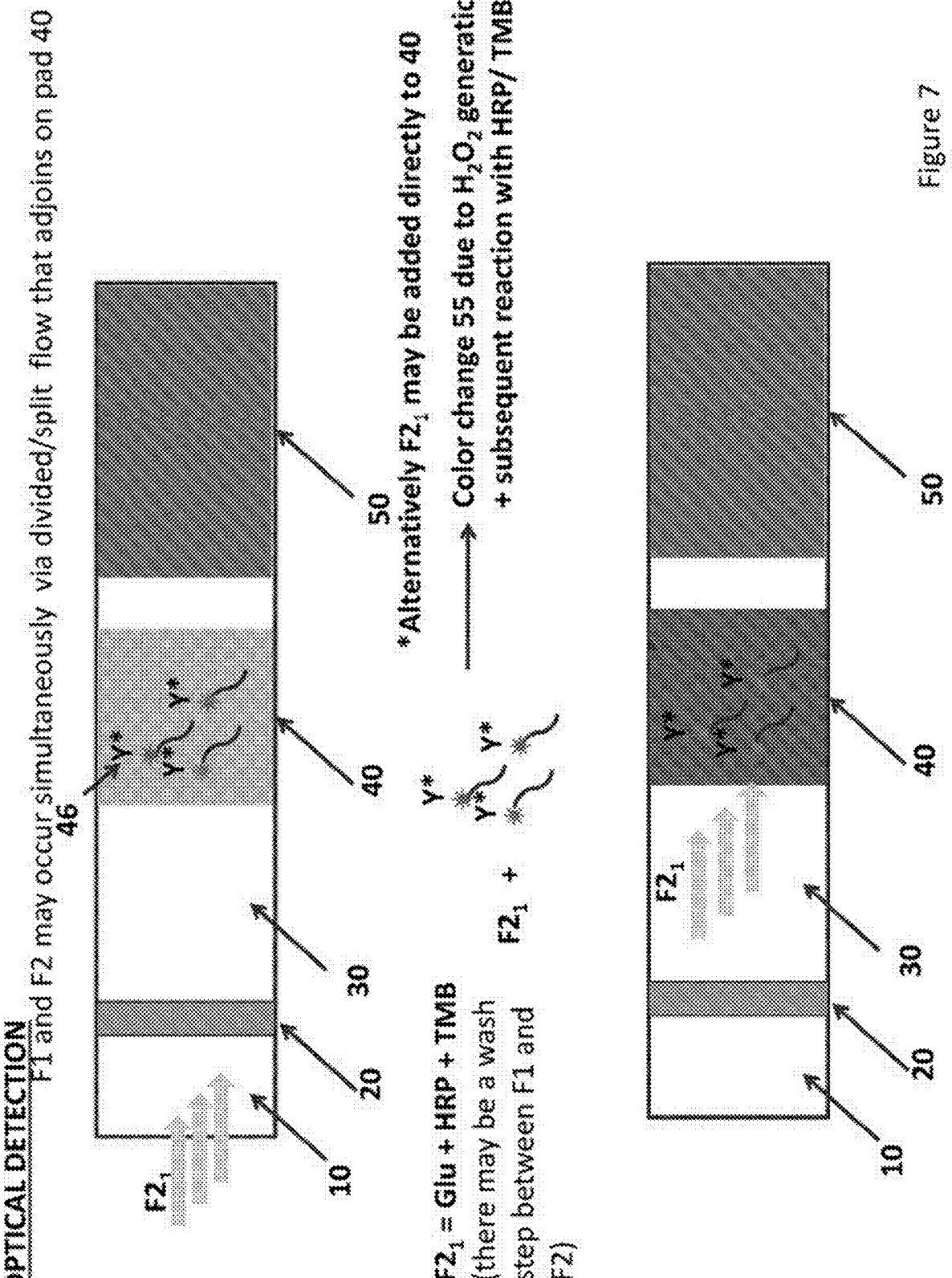
FIG. 7 shows a schematic top view procedural flow chart method for qualitative or quantitative detection of target analyte via optical means.
Figure 8:
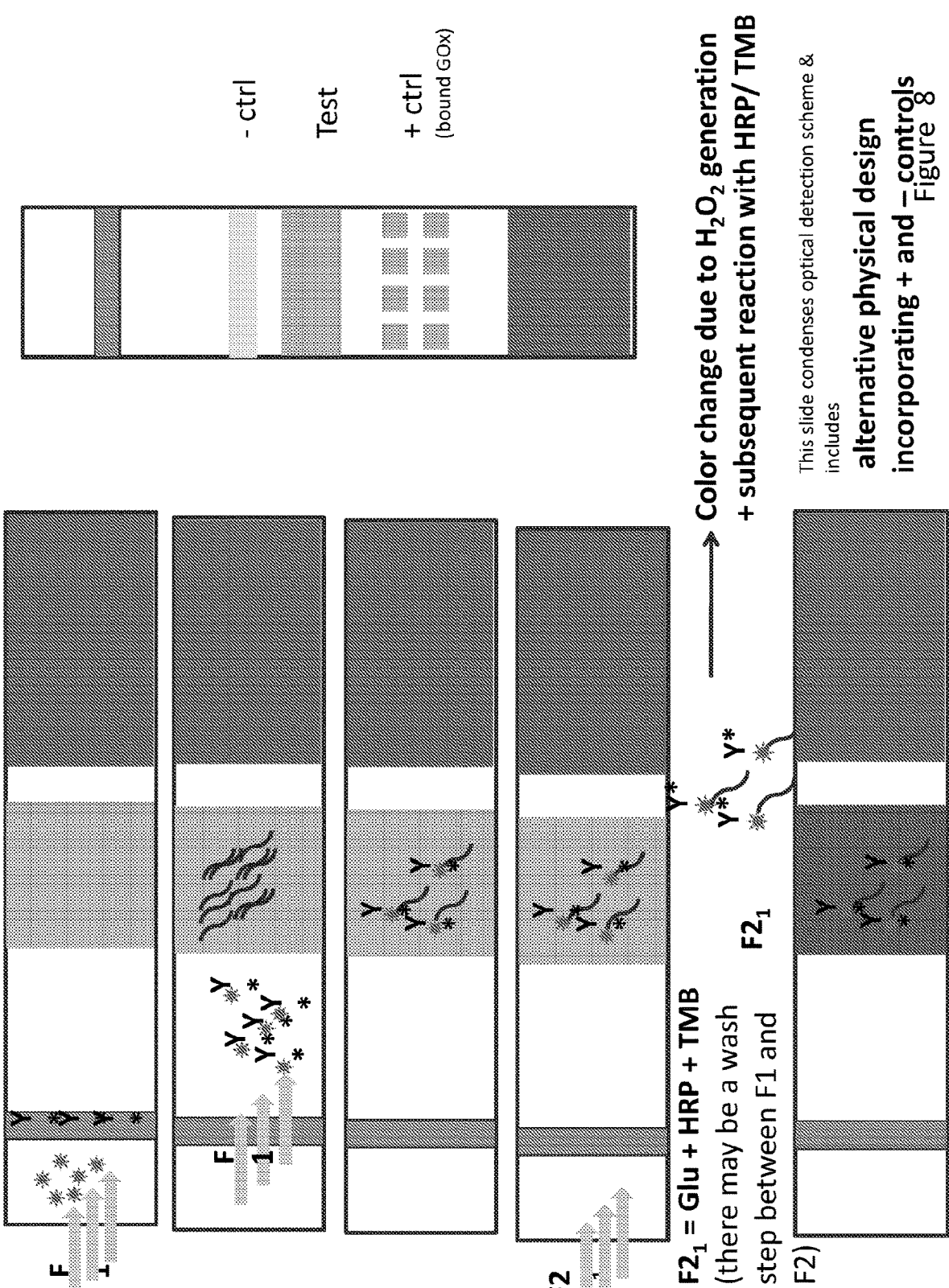
FIG. 8 shows a schematic top view of alternative physical design incorporating positive and negative controls in conjunction with optical detection.
Figure 10:
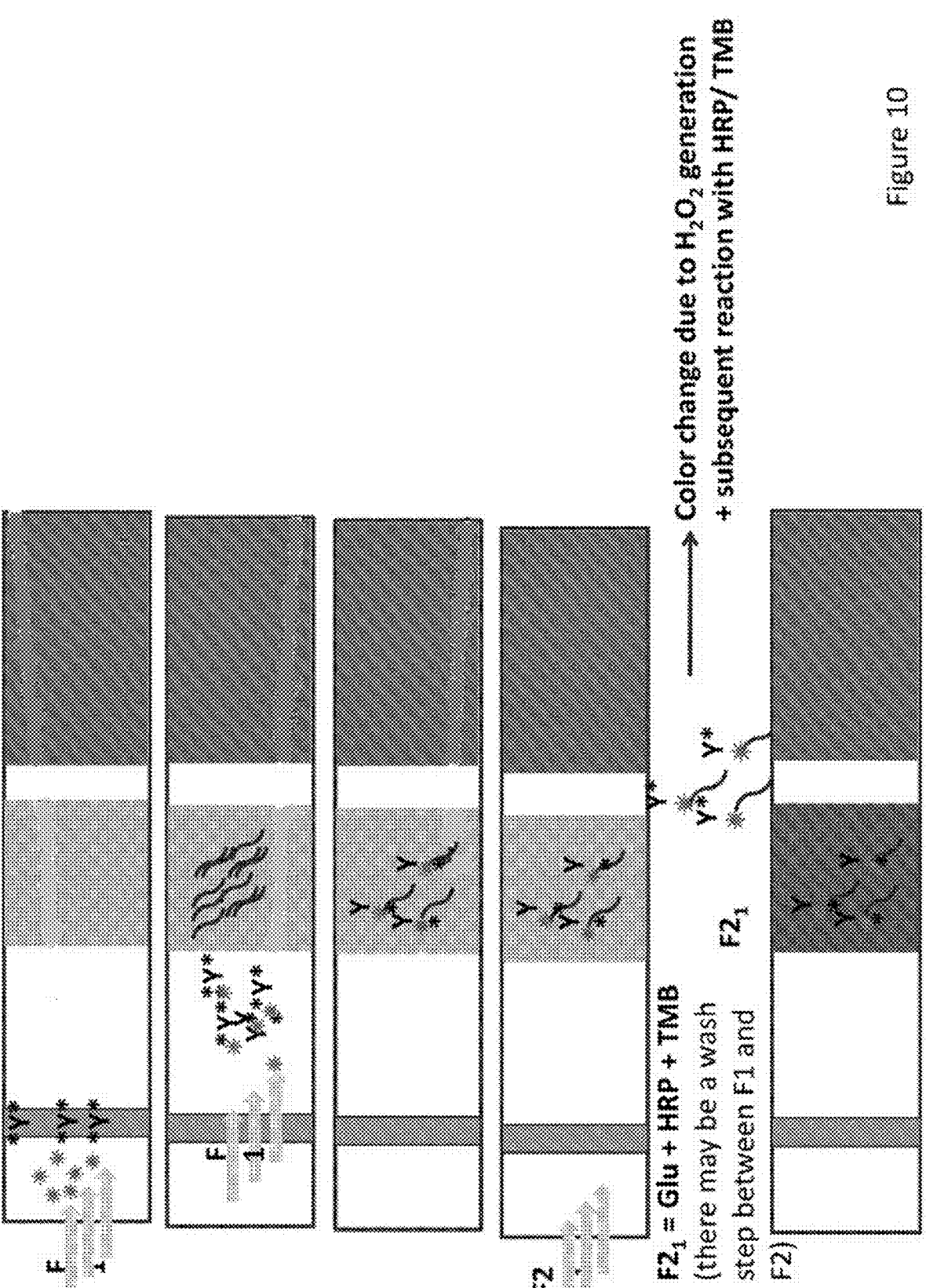
FIG. 10 shows a schematic top view procedural flow chart method for qualitative or quantitative detection of target analyte via optical means and HRP bound to Ab-GOx.
Figure 11:
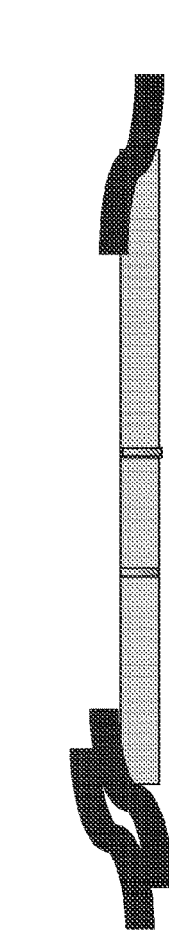
FIG. 11 shows components commonly used in conjunction with lateral flow devices.
Figure 12:
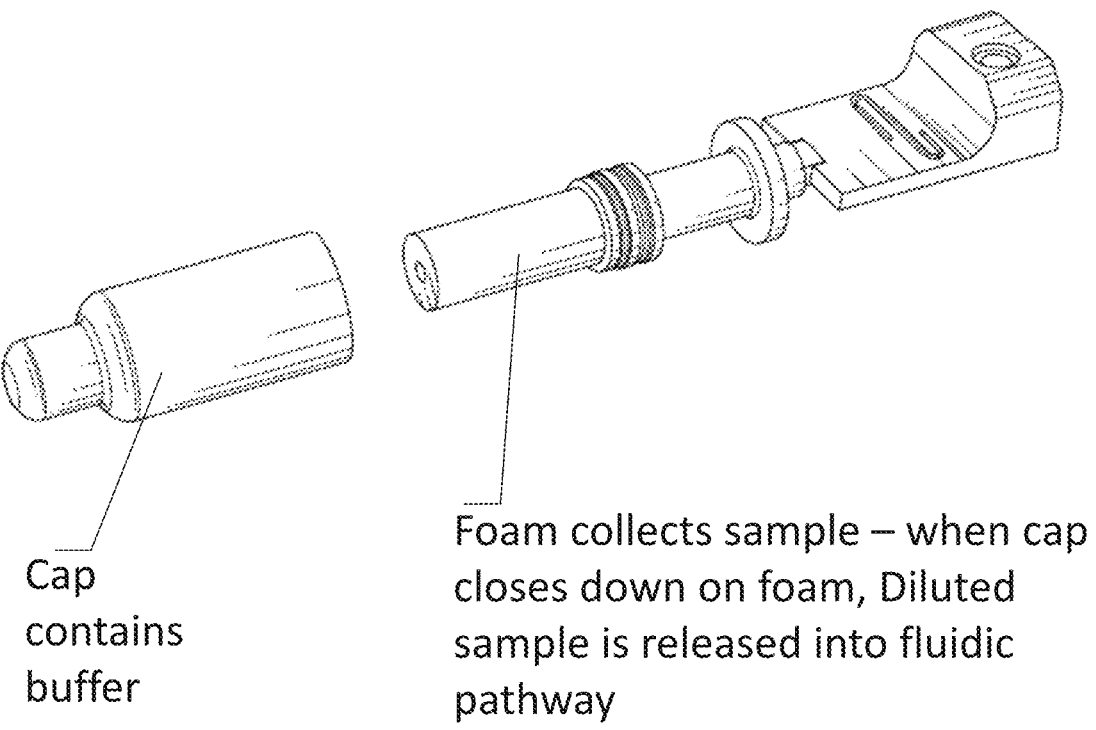
FIG. 12 shows a schematic of a sample integrator.

In a particular embodiment, the antibody is combined with glucose oxidase to provide an antibody-GOx conjugate. In another embodiment, alternate conjugate strategies using chemical linkers for site specific conjugation to GOx are utilized, e.g., a non-cleavable thioether and peptide linkage. As shown in FIG. 2, the aptamer captures the target analyte (protein) and Ab-GOx will bind only if protein is present. On application of a constant potential, GOx oxidizes glucose, transfers an electron to oxygen, produces hydrogen peroxide, and generates a current output via an electrode that reacts with hydrogen peroxide.

In a particular embodiment, the antibody is combined with oxidases to provide an antibody-Ox conjugate made from galactose oxidase, D-glucose:D-fructose oxidoreductase, and cellobiose oxidase.

In a particular embodiment, the antibody is combined with dehydrogenases to provide an antibody-DH conjugate made from glucose dehydrogenase, glucose 6-phosphate dehydrogenase, fructose dehydrogenase, sucrose dehydrogenase, glucoside dehydrogenase, alcohol dehydrogenase, sorbitol dehydrogenase, lactate dehydrogenase, and malate dehydrogenase.

In a particular embodiment, the detecting agent antibody is combined with glucose oxidase to provide an antibody- GOx conjugate and the third binding agent antibody is combined with horseradish peroxidase to provide an antibody-HRP conjugate. In another embodiment alternate conjugate strategies using chemical linkers for site specific conjugation to GOx or HRP are utilized, e.g., a non-cleavable thioether and peptide linkage. In embodiments of this three binding agent assay, the first and second binding agents may be specific to at least one protein wherein the third binding agent is an antibody linked with horseradish peroxidase.

Representative non-limiting colorimetric labels that can be utilized in the systems and assays described herein include colored latex (polystyrene) particles, colored polymeric particles, colored cellulose particles, metallic (e.g., gold) sols including gold nanoparticles, non-metallic elemental (e.g., Selenium, carbon) sols and dye sols.

D. Detection Device

Any suitable method of detecting the signal may be utilized. In certain embodiments, the detection device is a portable (e.g., hand-held), battery-powered device.

In certain embodiments, the detection device permits analysis of an analyte in sample by, for example, coulometry, amperometry and/or potentiometry.

In one embodiment, the device is selected from an amperometric device, a coulometric device, a potentiometric device or a voltammetric device.

The device may have a multiplicity of electrodes, e.g., at least two, at least three, at least four, at least five, at least six or more electrodes.

In one embodiment, the electrode is unmodified. In other embodiments, the electrode is modified, e.g., using metal (oxide) NPs, polymers, and other carbonaceous material In one embodiment, the device comprises three (3) electrodes including a working electrode, a counter electrode and a reference electrode.

In one embodiment, the device measured the reactant or product concentration, e.g., the hydrogen peroxide concentration produced or oxygen concentration consumed.

In another embodiment, the device is based on the use of redox mediators (Mox and MRED). According to this embodiment, the concentration of the analyte involved in the reaction is related to the response for the oxidation or reduction of the mediator In yet another embodiment, the device permits the direct electron transfer between a GOx-FADH2-nanomaterial conjugate and an electrode. According to this embodiment, the analyte concentration is directly proportional to the redox current generated at a polarized electrode set at a low operating potential (generally close to the enzyme's reversible redox potential) without the need for a mediator.

In embodiments where the signal is electrochemical, the detecting device may be an electrochemical device capable of performing an amperometric measurement or a potentiostat-based measurement tool.

In a particular embodiment, the detection device is a glucometer or personal glucose meter (PGM). Conventionally, a PGM is a portable handheld device used to measure blood glucose levels for users with Type I or Type II diabetes. Typically, the user purchases small strips (about 20-30 mm×about 5-9 mm) that interface with the PGM. The user draws a tiny amount of blood (a few microliters) from a finger or other area using a lancer, applies a blood droplet sample onto the exposed end of the strip, and then inserts the connector end of the strip into the PGM connector port. A chemical reaction occurs between the blood sample and the chemistry on the strip, which is measured by the PGM to determine the blood glucose level in units of mg/dL or mmol/L, or Kg/L. After measuring blood sugar levels, repeatedly, the used test strip is removed from the PGM and a new test strip is loaded into the connector port.

In one embodiment, the glucometer in the systems and methods herein in a standard, commercially available, hand-held glucometer. Non-limiting examples of commercially available glucometers include Accu Chek® (Roche Diabetes Care, Inc., Indianapolis, Indiana), Van Touch®, Bionime® Presto® (AgaMatrix, Salem, NH), Wavesense Presto® (Ag-aMatrix, Salem, NH), Counter® (Ascensia, Basel, Switzer-land), CounterPlus® (Ascensia, Basel, Switzerland), Free-Style® (Abbott Diabetes Care Inc. Abbott Park, Ill), True® (Trividia Health, Fort Lauderdale, Florida).

In certain embodiments, the glucometer is a limited-use or disposable glucometer or chronoamperometric device.

A glucometer typically includes a base unit that houses control and test electronics required to test the blood glucose levels in a blood sample. In other embodiments, the glu-cometer has been modified in one or more ways to enhance functionality for the detection of analytes, either generally or from saliva.

In a particular embodiment, the detection device is a glucometer or chronoamperometric device having a base unit having a cassette or test strip slot and a reader config-ured to analyze a biological sample (e.g., a saliva sample). In one embodiment, the glucometer measures the glucose signal (e.g., quantitatively). The base unit may vary in shape and size. The test strip slot is configured to accept a glucose style test strip or cassette such as those described herein, which may be removably inserted into the test strip slot. The glucometer may also have a means for storing data and transmitting data.

The glucose measurement may be performed by standard amperometric detection of glucose using glucose oxidase. In this embodiment, the glucose concentration in the biological fluid is converted into a voltage or current signal using a sensor. The sensor uses a platinum and silver electrode to form part of an electric circuit where hydrogen peroxide is electrolyzed. The hydrogen peroxide is produced as a result of the oxidation of glucose on a glucose oxide membrane. The current flowing through the circuit provides a measure-ment of the concentration of hydrogen peroxide, giving the glucose concentration.

The glucose measurement may be performed by standard amperometric detection of glucose using glucose oxidase. In this embodiment, the glucose concentration in the biological fluid is converted into a voltage or current signal using a sensor. The sensor uses carbon electrode(s) to form part of an electric circuit where hydrogen peroxide is electrolyzed. The hydrogen peroxide is produced as a result of the oxidation of glucose on a glucose oxide membrane. The current flowing through the circuit provides a measurement of the concentration of hydrogen peroxide, giving the glu-cose concentration.

In certain embodiments, the system comprises one or more signal processing applications or electronic amplifiers in the circuit to amplify the signal.

In another embodiment, signal collection and process may be obtained via a static or pulsed process, with pulsing from about 1 second pulse to about 5 minute wait, about 1 second pulse to about 2 minute wait, about 2 second pulse to about 1 minute wait, or about 2 sec pulse to about 30 second wait.

In one embodiment, the device includes a display unit for displaying the result. The display may display the most recent test and, optionally, previous tests are displayed. In certain embodiments, the glucometer includes a voice con-trol function for ease of use by vision-impaired subjects. The glucometer may include other features unrelated to glucose measurement, e.g., measurement of other physiological functions. The glucose readings displayed on the glucometer will positively correlate to enzyme concentration on the sensor surface which in turn correlates to number of analytes (e.g., protein(s) present in the biological sample).

The glucometer may have a software element. Various software algorithm for glucometers are known.

In one embodiment, the glucometer has a wireless trans-mitter is configured to communicate a message to a second device, e.g., a mobile device, such as a cellular phone or a tablet computer. In one embodiment, the message is sent to the second device over a short distance communication protocol, e.g., a Bluetooth protocol. The message may also be, for example, a text message or email.

In one embodiment, the glucometer produces a result rapidly after testing has begun, e.g., less than about 5 minutes, less than about 1 minute 30 seconds, less than about 15 seconds or less than about 5 seconds.

The accuracy of the glucometer may vary but is generally does not exceed 20% error and more particularly, does not exceed about 15%, about 10%, about 5% or less than about 5% error, e.g., about 4%, about 3%, about 2% or about 1% or less error. In certain embodiments, cross-sensitivity of the glucometer is reduced or limited based on experimental determination and verification of new correction factors. In one embodiment, the accuracy of the glucometer ranges between about 85% and about 95%.

In one embodiment, the glucometer permits the user to save the latest values of the tests and calculate the average value of glucose for two (2) weeks, thereby permitting monitoring over time.

In certain embodiments, modified chronoamperometric methods are disclosed differing from either a) constant chronoamperometry (enforcing potential, for example, for a few minutes while simultaneously acquiring current) or b) delayed chronoamperometry (allowing substrate to incubate on electrode for a period of time, for example, for a few minutes, and subsequently subjecting to constant chrono-amperometric investigation, for example, for a few minutes while simultaneously acquiring current) permit faster and/or more sensitive measurements (e.g. afford lower limit of detection) related to detection of a target analyte.

Such modified chronoamperometric methods are employed to collect signal (current, charge), increase signal, improve signal to noise, improve sensitivity (e.g. limit of detection), reduce time to signal, multiplex on multiple working electrodes, and/or reduce background. Variables include but are not limited to enforced potential, pulse time, delay before measurement, measurement time, time at open circuit, number of cycles, measurement sampling rate, etc. Other variables will be known to those skilled in the art.

In certain embodiments, modified chronoamperometric methods are employed (e.g., pulsed detection) in combina-tion with the titration of compounds or counterions (e.g., $MgCl_2$).

In certain embodiments, the glucose meter is "display-less" in order to minimize the complexity and cost of the meter unit. According to this embodiment, the glucose meter is wirelessly enabled and send the result or readout to a second device, e.g., a cell phone or personal computer.

Optionally, the glucometer also includes a transmitter configured to wirelessly transmit data, encoded within an audio signal, regarding results of the analysis, and a con-troller configured to facilitate the encoding.

Also disclosed herein is a remote computing device which may be used in the systems and methods herein that are a glucometer, and remote computing device. In one embodiment, the remote communicating device may be, for example, a smartphone or any other suitable device such as a communications device, and which may constitute an output device.

The glucometer transmits the measurements through the transmitter unit, for example over a wireless audio-based channel, to the remote computing device.

The remote computing device may further communicate information to remote devices, such as a central repository device, through a network such as internet- or mobile-based device to a recipient list. For example, the detection device may transmit medical data through the remote computing device. The data may thereafter be communicated to a remote caregiver, e.g., via a computer or handheld device, such as a smartphone.

In this embodiment a software algorithm is disclosed that triggers electrochemical reactions in detection system such that one or more detectable chemical species are the reaction product of a biological sample, within a cassette or test strip and detection device.

In one embodiment, mathematical operations are performed algorithmically localized computing on the detection device such that chemical reactions that afford detectable reaction products proceed between the biological sample, cassette or test strip components and detection device.

In one embodiment, mathematical operations are performed using cloud computing on servers in a physical location external to the location of the detection device such that chemical reactions that afford detectable reaction products proceed between the biological sample, cassette or test strip components and detection device.

In one embodiment, a data card containing additional algorithms non initially programmed on detection device is inserted into a data card slot on detection device such that chemical reactions occur that afford detectable reaction products proceed between the biological sample, cassette or test strip components and detection device.

In one embodiment, a non-transitory computer-readable storage medium is disclosed, encoded with executable instructions for execution by a processor to detect a target analyte.

In embodiments where the signal is optical, e.g., colorimetric, the detecting device may be a camera or mobile phone.

The detecting device may detect, for example, hue, intensity, fluorescence, electrons, voltage changes, impedance changes or the like.

In certain embodiments, the signal can be detected without the need for a detecting device, i.e., the signal can be visualized by the naked eye.

In certain embodiments, detection may involve the formation of a precipitate, e.g., via alkaline phosphatase enzyme mediated reactions in conjunction with precipitate rendering NBT-BCIP.

In one embodiment, glucose oxidase catalyzes the oxidation of glucose to form hydrogen peroxide, which is then quantified by amperometric measurements (e.g. change in electrical current) through one or more electrodes. As the amount of glucose in the sample is in excess, the amperometric quantification is for the target analyte.

In certain embodiments, the result is recorded as a loss of the detectable complex. In other embodiments, the result is record as a gain of detectable complex.

The detection device may optionally comprise a collection chamber, for receiving the sample, and/or a diluter unit.

The detection reader or the electrochemical detection reader can include a casing or a housing that houses a computing device, and a display. The display can include liquid crystal display (LCD) displays, gas plasma-based flat panel displays, organic light emitting diode (OLED) displays, electrophoretic ink (E-ink) displays, LCD projectors, or other types of display devices.

The detection reader can be adapted to removably receive the cassette or the strip. In some examples, the detection reader can include a receiver apparatus that is disposed within the housing and acc The detector device may include data storage, Bluetooth, wireless capabilities, transmission capabilities or the like. The system may comprise an electronic device, data base, or cloud server for receiving information from the detection device about the signal.

In certain embodiments, the system comprises an algorithm that triggers monitoring of the electrochemical reactions in the detection system. In certain embodiment, the system comprises an algorithm that determines the concentration of the at least one analyte. The algorithm may be localized or cloud-based.

Applications or other functionality can be executed in a networked environment according to examples. The networked environment can include the detection device and one or more client device(s) in communication over a network. The network can include the internet, one or more intranets, extranets, wide area networks (WANs), local area networks (LANs), wired networks, wireless networks, or any combination of two or more such networks. The network can include satellite networks, cable networks, Ethernet networks, cellular networks, and telephony networks.

The detection device can execute a detection application for detection (e.g., amperometric detection), and other applications, services, processes, systems, engines, or functionality not discussed in detail herein. The detection device including the detection application can include, afford or perform other forms of electrochemical characterization, such as impedance spectroscopy, and/or optical characterization (e.g., via spectrophotometry, intensity, fluorescence, chemiluminescence, UV/Vis). One or more measurements can be stored in a data store (e.g., recorded as a function of time). Data transmitted via the network may be qualitative or quantitative. Test results (raw, processed, etc.), control data, and potentially other types of data can be stored or transmitted.

The client device can include a processor-based system, such as a computer system, that can include a desktop computer, a laptop computer, a personal digital assistant, a cellular telephone, a smartphone, a tablet computer system, an IoT device, or any other device with like capability.

In some examples, a system is provided. The system can include a detection device comprising a computing device. The detection reader can be adapted to removably receive the cassette. The system can include program instructions executable in the computing device that, when executed by the computing device, cause the computing device to, among other things, detect an insertion of the cassette. The program instructions can cause the actuator arm of the detection reader or the electrochemical detection reader to be actuated thereby causing the release of glucose from the glucose pod.

The program instructions can generate output data. The output data can include data that is calibrated to the presence or concentration of the target analyte(s), which can be not glucose, within a biological sample. The program instructions can cause the output data to be rendered on the display of the detection reader, or cause a user interface to be generated and send to the client device to render the output data on a display of the client device.

A number of software components are stored in the memory of a computing device and are executable by a processor. In this respect, the term "executable" means a program file that is in a form that can ultimately be run by the processor. Examples of executable programs can be a compiled program that can be translated into machine code in a format that can be loaded into a random access portion of the memory and run by the processor, source code that can be expressed in proper format such as object code that is capable of being loaded into a random access portion of the memory and executed by the processor, or source code that can be interpreted by another executable program to generate instructions in a random access portion of the memory to be executed by the processor. An executable program can be stored in any portion or component of the memory including random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory can include both volatile and nonvolatile memory and data storage components. Volatile components are those that do not retain data values upon loss of power. Nonvolatile components are those that retain data upon a loss of power. Thus, the memory can comprise random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM can comprise static random access memory (SRAM), dynamic random access memory (DRAM), or magnetic random access memory (MRAM) and other such devices. The ROM can comprise a programmable read-only memory (PROM), an erasable programmable read-only memory (EPROM), an electrically erasable programmable read-only memory (EEPROM), or other like memory device. Also, the processor can represent multiple processors and/or multiple processor cores and the memory can represent multiple memories that operate in parallel processing circuits, respectively.

Although the detection reader, the electrochemical detection reader, and any applications or services described herein can be embodied in software or code executed by general purpose hardware that is specially configured or programmed as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components. Such technologies are generally well known by those skilled in the art and, consequently, are not described in detail herein.

In one embodiment, the assay comprises a lateral flow assay and an electrochemical detection system. In a particular embodiment, the lateral flow assay comprises at least one target binding site. Optionally, the at least one target binding site on the membrane is positioned at, above or below an electrode. Optionally, the lateral flow assay further comprises at least one control site comprising at least one control element, in order to monitor the performance of the system. Optionally, the control site may be positioned above another electrode.

In a particular embodiment, the electrochemical detection is only performed upon insertion of the strip into the electrochemical device providing the differential voltage and detecting the current output provided by the strip and accompanying electrode.

II. Methods of Use

Disclosed is a method of detecting at least one target analyte using the systems and assays disclose herein. Also disclosed is a method of treating a subject using the systems and assays disclosed herein, as well as preparing the systems and assays disclosed herein.

In certain embodiments, the methods may be conducted in numerous environments, including the home, in the office, or in operational field or in resource limited environments with the low limit of detection and high accuracy required to be truly useful with respect to analyte detection. POC testing can be essential for rapid detection of the disease at early stages to facilitate better disease diagnosis, monitoring and management. In other embodiments, the methods can be conducted in a healthcare setting such as a clinic or emergency room.

The detection of the analyte is performed between 5 and 30° C. In a particular embodiment, the detection of the analyte is performed between 17 and 25° C.

In one embodiment, the method comprises (i) obtaining a sample; (ii) optionally, processing the sample; (iii) adding the sample to the system disclosed herein; (iv) allowing the target analyte if present to bind to a capture binding agent, thereby generating a signal and (v) detecting the presence of target analyte in the sample by detecting the signal. In certain embodiments, a diagnosis is possible where the concentration of the target analyte, as indicated by the signal, is higher than a reference value.

In one embodiment, a method of sample preparation is provided comprising (i) obtaining a sample; (ii) processing the sample; (iii) adding the sample to the system or assay disclosed herein; (iv) allowing the target analyte if present to bind to a capture agent, thereby generating a signal and (v) detecting the presence of target analyte in the sample by detecting the signal.

The processing in (ii) may vary in the above embodiments. The processing may be done prior to adding the sample to the system or assay. In one embodiment, the processing comprises diluting the sample.

In embodiment, the processing comprising adding one or more assay components or reagents to the sample. In a particular embodiment, the processing comprises adding capture agent and/or detection agent to the sample before it is added to the assay.

In a particular embodiment, the processing comprises adding a biotin-conjugated capture agent (e.g., an aptamer or antibody) and a labeled detection agent (e.g., aptamer or antibody) to the system or assay disclosed herein.

In one embodiment, the processing comprises adding a substrate (e.g., an enzyme substrate) to the system or assay disclosed herein. The substrate may be, for example, sucrose, fructose, maltose, galactose, cellulose, or any combination that includes an enzyme, oxidase, amylase or invertase. The concentration of the sugar may vary. In one embodiment, the sugar is present at a concentration between 0.01 mM and 5 M and more particularly, about 0.3 and about 0.8, and even more particularly, about 0.05 M. In other embodiments, the glucose is present within the strip as opposed to added by the user.

In one embodiment, the target analyte is mixed with a substrate (e.g., glucose) and a dye such as 3,3',5,5'-Tetramethylbenzidine (TMB). In a particular embodiment, the target analyte is mixed with glucose at a concentration between about 0.01 mM and about 5 M and TMB at a concentration between about 0.001 mM and 5 M.

In other embodiments, the target analyte is mixed with horseradish peroxidase at a concentration between about 0.0000001 mM and about 1 M.

In other embodiments, the target analyte is mixed with catalase at a concentration between about 0.0000001 mM and about 1 M.

In a particular embodiment, the allowing in (iii) comprises an incubation period, e.g., an incubation period of between about several seconds to about 10 minutes.

In a particular embodiment, the method may further comprises one or more washing steps, for instance, post incubation period and before detection period, wherein the washing step(s) requires to use to remove or wick of some portion of the solution or to remove any unbound sample. In some embodiments, the method comprises less than five washing steps, less than three washing steps, less than two washing steps, or one washing step.

In certain embodiment, the analysis of the chronoamperometric collected data enables differentiation of an analyte containing sample from a control sample with no analyte. For example, the area of curve, the end point measurement, the initial slope of the curve, the derivatives of curves, selected single or multiple time point before the data plateaus, are collected and reveal differences between the samples measured.

In one embodiment, a method is provided for treating a subject, comprising (i) providing a biological sample from the subject (e.g., saliva), (ii) optionally, processing the sample; (iii) adding the sample to the systems or assays disclosed herein; (iv) if a target analyte (e.g., whole virus) is present, detecting the target analyte to provide a result, and (v) administering an approved therapeutic agent to the subject, if warranted, thereby treating the subject.

In a particular embodiment, the result is calibrated against a disease state (e.g., an infection) or a healthy state. In a particular embodiment, the result is associated with an infectious with a virus, a bacteria, a fungi or other microorganism. In certain embodiments, the result is associated with the presence of an allergen. In other embodiments, the result is associated with inflammation, cancer or heart disease.

In a particular embodiment, the detecting in (iv) is via a glucometer or mobile phone.

The approved therapeutic agent may vary. In one embodiment, the approval therapeutic agent is a small molecule agent (e.g., an anti-viral agent) or a biologic agent (e.g., a protein, antibody, therapeutic vaccine).

In a particular embodiment, the therapeutic agent is an anti-viral agent.

In one embodiment, the anti-viral agent is an attachment inhibitor, an entry inhibitor, an uncoating inhibitor, a protease inhibitor, an integrase inhibitor, a nucleoside or nucleotide reverse transcriptase inhibitor or a replication or transcription complex blocker.

In a particular embodiment, the therapeutic agent is an anti-inflammatory agent.

In one embodiment, the anti-inflammatory agent is a non-steroidal anti-inflammatory drug (NSAID). In a particular embodiment, the anti-inflammatory agent is a derivative of acetic acid, anthranilic acid, enolic acid, or propionic acid. In one embodiment, the anti-inflammatory agent is selected from celecoxib, naproxen, meloxicam, nabumetone, oxaprozin and piroxicam.

In a particular embodiment, the therapeutic agent is an anti-cancer agent.

In one embodiment, the anti-cancer agent is selected from an from an alkylating agent (or alkylating-like agent), an antimetabolite, an antitumor antibiotic, a mitotic inhibitor, a protein kinase inhibitor, a plant alkaloid, a hormonal agent, a topoisomerase inhibitor (e.g., topoisomerase I inhibitor, topoisomerase II inhibitor) or the like.

In a particular embodiment, the anticancer agent is selected from an alkylating agent selected from a mustard gas derivative, an ethylenimine, an alkylsulfonate, a hydrazine, a triazine, a nutrosurea, or a metal salt.

In a particular embodiment, the anticancer agent is an antimetabolite selected from a folic acid antagonist, a pyrimidine antagonist, a purine antagonist or an adenosine deaminase inhibitor.

In a particular embodiment, the anticancer agent is an antitumor antibiotic selected from an anthracycline, chromomycin or the like.

In certain embodiments, the anticancer agent is selected from cyclophosphamide, the nitrosoureas, cisplatin, methotrexate, cytarabine, 5-fluorouracil, doxorubicin, daunorubicin, bleomycin, vincristine, vinblastine, vindesine or a combination thereof.

In one embodiment, the method further comprising transmitting the result to a third party for diagnosis and optionally, prescribing of the approved therapeutic agent.

In one embodiment, if the treatment regime does not produce a detectable improvement in one or more symptoms or clinical measures of disease (e.g., a reduction in viral count within a defined period such as several days), the treatment may be discontinued in favor of an alternative treatment regime or in certain embodiments, supplement the treatment regime with a second treatment regime.

In one embodiment, the method comprises (i) providing a biological sample from a subject, wherein the biological sample is blood; (ii) adding the biological sample to a test strip, wherein the strip contains a first and second binding agent capable of create a detectable complex with at least one target analyte in the biological sample, if present; (iii) introducing the test strip into a glucometer or similar device; (iv) incubating the biological sample with the test strip; (v) detecting the level of detectable complex, if any, in the form of hydrogen peroxide generated from glucose oxidation of excess glucose present; and (vi) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, saliva, sweat, ocular fluid including aqueous humor, blood, fecal matter, sebum, respiratory droplets, semen, vaginal mucus, cerumen, epidermal cells, nasal sample, cerebral spinal fluid, pleural effusion, nasopharyngeal specimens, or combination thereof; (ii) swabbed biological sample; (iii) adding the biological sample to a strip, wherein the test strip contains a first and second binding agent capable of create a detectable complex with at least one target analyte in the biological sample, if present; (iv) introducing the test strip into a glucometer or similar chronoamperometric device; (v) incubating the biological sample with the test cassette or strip; (vi) detecting the level of detectable complex, if any, in the form of hydrogen peroxide generated from glucose oxidation of excess glucose present; and (vii) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is blood, in a tube which dilutes the biological sample by 1× to 1,000,000,000× and contains the second binding agent; (ii) adding the biological sample to a test strip, wherein the test strip contains the first binding agent capable of create a detectable complex with at least one target analyte in the biological sample, if present; (iii) introducing the test strip into a glucometer or chronoamperometric device; (iv) incubating the biological sample with the test strip; (v) detecting the level of detectable complex, if any, in the form of hydrogen peroxide generated from glucose oxidation of excess glucose present; and (vi) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, sweat, ocular fluid including aqueous humor, blood, fecal matter, sebum, respiratory droplets, semen, vaginal mucus, cerumen, epidermal cells, or nasopharyngeal specimens, in a tube which dilutes the biological sample by 1× to 1,000,000,000× and contains the second binding agent; (ii) swabbed biological sample; (iii) adding the biological sample to a test strip, wherein the test strip contains the first binding agent capable of create a detectable complex with at least one target analyte in the biological sample, if present; (iv) introducing the test strip into a glucometer or chronoamperometric device; (v) incubating the biological sample with the test strip; (vi) detecting the level of detectable complex, if any, in the form of hydrogen peroxide generated from glucose oxidation of excess glucose present; and (vii) correlating the level of the detectable complex, if produced, with the quantity of the target analyte in the at least one biological sample, if any, thereby providing a diagnostic assessment.

In one embodiment, the method comprises (i) providing a biological sample from a subject, wherein the biological sample is blood; (ii) adding the biological sample to a test strip, wherein the test strip contains a first binding agent capable of create a detectable complex with at least one target analyte, if present, in the biological sample in competition with the target analyte conjugated to glucose oxidase; (iii) introducing the test strip into a glucometer or similar device; (iv) incubating the biological sample with the test strip; (v) detecting the level of detectable complex, if any, in the form of hydrogen peroxide generated from glucose oxidation of excess glucose present; and (vi) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, saliva, sweat, ocular fluid including aqueous humor, blood, fecal matter, sebum, respiratory droplets, semen, vaginal mucus, cerumen, epidermal cells, nasal sample, cerebral spinal fluid, pleural effusion, or nasopharyngeal specimens; (ii) swabbed biological sample; (iii) adding the biological sample to a test strip, wherein the test strip contains a first binding agent capable of create a detectable complex with at least one target analyte in the biological sample, if present, in competition with the target analyte conjugated to glucose oxidase; (iv) introducing the test strip into a glucometer or chronoamperometric device; (v) incubating the biological sample with the test strip; (vi) detecting the level of detectable complex, if any, in the form of hydrogen peroxide generated from glucose oxidation of excess glucose present; and (vii) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is blood, in a tube which dilutes the biological sample by 1× to 1,000,000,000× and contains the second binding agent; (ii) adding the biological sample to a test strip, wherein the test strip contains the first binding agent capable of create a detectable complex with at least one target analyte in the biological sample, if present, in competition with the target analyte conjugated to glucose oxidase; (iii) introducing the test strip into a glucometer or similar device; (iv) incubating the biological sample with the test strip; (v) detecting the level of detectable complex, if any, in the form of hydrogen peroxide generated from glucose oxidation of excess glucose present; and (vi) correlating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, sweat, ocular fluid including aqueous humor, blood, fecal matter, sebum, respiratory droplets, semen, vaginal mucus, cerumen, epidermal cells, or nasopharyngeal specimens, in a tube which dilutes the biological sample by 1× to 1,000,000,000× and contains the second binding agent; (ii) swabbed biological sample; (iii) adding the biological sample to a test strip, wherein the test strip contains the first binding agent capable of create a detectable complex with at least one target analyte in the biological sample, if present, in competition with the target analyte conjugated to glucose oxidase; (iv) introducing the test strip into a glucometer or chronoamperometric device; (v) incubating the biological sample with the test strip; (vi) detecting the level of detectable complex, if any, in the form of hydrogen peroxide generated from glucose oxidation of excess glucose present; and (vii) calibrating the level of the detectable complex, if produced, with the quantity of the target analyte in the at least one biological sample, if any, thereby providing a diagnostic assessment.

In one embodiment, the method comprises obtaining multiple test results for the same user taken at different times and comparing these to monitor or predict or follow the likely development of a disease or condition. In a particular embodiment, the method comprises obtaining at least two, at least three, at least four or at least five test results.

In certain embodiments, the one or more results of the method may be continuously or periodically communicated to a remote entity to determine whether the one or more results are above a threshold level or cut point.

In certain embodiments, the results may be compared to a pre-determined reference level. The pre-determined level may be obtained from the general population or from a selected population of subjects. For example, the selected population may be comprised of apparently healthy patients, such as individuals who have not previously had any sign or symptoms indicating the presence of an disease, e.g., an infection. A "pre-determined reference level" may be determined, for example, by determining the expression level of the target analyte in a corresponding biological sample obtained from one or more control subject(s) (e.g., not suffering from infection or known not to be susceptible to such a disease). When such a pre-determined reference level is used, a higher or increased levels determined in a biological sample (i.e. a test sample obtained from the subject) is indicative for example that said patient is at risk of developing the disease Optionally, method may further comprise the step of recommending or instructions for a treatment and/or administering a treatment. In one embodiment, the method comprises identifying that the subject has a level of target analyte above a threshold of cut off level and determining that the subject is therefore a candidate for prophylaxis and/or treatment, e.g., of an infection or pathological condition. The step of "determining" encompasses detecting or quantifying, wherein "detecting" means determining if the target analyte is present or not in the biological sample and "quantifying" means determining the amount of the target analyte present in the biological sample.

The method of the invention may have therapeutic uses for example it may be used for the detection of various pathological conditions or may be used for monitoring the disease stage of a subject or its response to therapy.

In certain embodiments, the method may further comprise using statistical methods to predict the potential for detection of a target analyte to result in disease or progression of disease and/or to permit prognosis of disease (i.e., prediction of the course of a disease).

In certain embodiments, the method may be carried out across a group of population of patients, e.g., in order to permit stratifying the approach to treatment thereof or to satisfy a public health or other monitoring goal.

In one embodiment, a method is disclosed for monitoring the efficiency of a therapeutic regimen in a subject suffering from a pathological condition comprising using the methods and/or system disclosed herein wherein said target molecule is an antigen associated with the pathological condition and wherein the amount of said detectable moiety is indicative of the level of the pathological condition and thereby of the efficiency of the therapeutic regimen in the subject.

In certain embodiments, the method comprises monitoring the effectiveness of one more therapeutic agents (e.g., anti-viral agents, anticancer agents, etc.) over a period of time (e.g., days, weeks) and permits the user to seek an alternative therapeutic approach if the therapeutic agent is not sufficiently effective over a period of time.

In one embodiment, if the treatment regime does not produce a reduction in condition within a defined period (e.g., days), the user may discontinue the treatment regime in favor of an alternative treatment regime or in certain embodiments, supplement the treatment regime with a second treatment regime. In one embodiment, the system permits obtaining two or more results, three or more results or five or more results with respect to the quantity of a target analyte for the same user at different times, to permit monitoring of a trend in analyte level over time.

In one method, the method comprises (i) providing a biological sample from a subject, wherein the biological sample is blood; (ii) adding the biological sample to a test strip, wherein the strip contains a first and second binding agent capable of create a detectable complex with at least one target analyte in the biological sample, if present; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, saliva, sweat, ocular fluid including aqueous humor, blood, fecal matter, sebum, respiratory droplets, semen, vaginal mucus, cerumen, epidermal cells, nasal sample, cerebral spinal fluid, pleural effusion, or nasopharyngeal specimens; (ii) swabbed biological sample; (iii) adding the biological sample to a strip, wherein the test strip contains a first and second binding agent capable of create a detectable complex with at least one target analyte in the biological sample, if present; (iv) incubating the detectable complex with horseradish peroxidase and a dye such as 3,3',5,5-tetramethylbenzidine on the strip; (v) detecting the level of detectable complex, if any, in the form a color change, and (vi) correlating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is blood, in a tube which dilutes the biological sample by 1× to 1,000,000,000× and contains the second binding agent; (ii) adding the biological sample to a test strip, wherein the test strip contains the first binding agent capable of create a detectable complex with at least one target analyte in the biological sample, if present; (iii) incubating the detectable complex with horseradish peroxidase and a dye such as 3,3',5,5-tetramethylbenzidine on the strip; (iv) detecting the level of detectable complex, if any, in the form a color change, and (v) correlating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, sweat, ocular fluid including aqueous humor, blood, fecal matter, sebum, respiratory droplets, semen, vaginal mucus, cerumen, epidermal cells, or nasopharyngeal specimens, in a tube which dilutes the biological sample by 1× to 1,000,000,000× and contains the second binding agent; (ii) adding the biological sample to a test strip, wherein the test strip contains the first binding agent capable of create a detectable complex with at least one target analyte in the biological sample, if present; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) providing a biological sample from a subject, wherein the biological sample is blood; (ii) adding the biological sample to a test strip, wherein the test strip contains a first binding agent capable of create a detectable complex with at least one target analyte, if present, in the biological sample in competition with the target analyte conjugated to glucose oxidase; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, saliva, sweat, ocular fluid including aqueous humor, blood, fecal matter, sebum, respiratory droplets, semen, vaginal mucus, cerumen, epidermal cells, nasal sample, cerebral spinal fluid, pleural effusion, or nasopharyngeal specimens; (ii) swabbed biological sample; (iii) adding the biological sample to a test strip, wherein the test strip contains a first binding agent capable of create a detectable complex with at least one target analyte in the biological sample, if present, in competition with the target analyte conjugated to glucose oxidase; (iv) incubating the detectable complex with horseradish peroxidase and a dye such as 3,3',5,5-tetramethylbenzidine on the strip; (v) detecting the level of detectable complex, if any, in the form a color change, and (vi) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is blood, in a tube which dilutes the biological sample by 1× to 1,000,000,000× and contains the second binding agent; (ii) adding the biological sample to a test strip, wherein the test strip contains the first binding agent capable of create a detectable complex with at least one target analyte in the biological sample, if present, in competition with the target analyte conjugated to glucose oxidase; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, sweat, ocular fluid including aqueous humor, blood, fecal matter, sebum, respiratory droplets, semen, vaginal mucus, cerumen, epidermal cells, or nasopharyngeal specimens, in a tube which dilutes the biological sample by 1× to 1,000,000,000× and contains the second binding agent; (ii) adding the biological sample to a test strip, wherein the test strip contains the first binding agent capable of create a detectable complex with at least one target analyte in the biological sample, if present, in competition with the target analyte conjugated to glucose oxidase; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises obtaining multiple test results for the same user taken at different times and comparing these to monitor or predict or follow the likely development of a disease or condition. In a particular embodiment, the method comprising obtaining at least two, at least three, at least four or at least five tests results.

In certain embodiments, the one or more results of the method may be continuously or periodically communicated to a remote entity to determine whether the one or more results are above a threshold level or cut point.

In certain embodiments, the results may be compared to a pre-determined reference level. The pre-determined level may be obtained from the general population or from a selected population of subjects. For example, the selected population may be comprised of apparently healthy patients, such as individuals who have not previously had any sign or symptoms indicating the presence of an disease, e.g., an infection. A "predetermined reference level" may be determined, for example, by determining the expression level of the target analyte in a corresponding biological sample obtained from one or more control subject(s) (e.g., not suffering from infection or known not to be susceptible to such a disease). When such a predetermined reference level is used, a higher or increased levels determined in a biological sample (i.e. a test sample obtained from the subject) is indicative for example that said patient is at risk of developing the disease Optionally, method may further comprise the step of recommending or instructions for a treatment and/or administering a treatment. In one embodiment, the method comprises identifying that the subject has a level of target analyte above a threshold of cut off level and determining that the subject is therefore a candidate for prophylaxis and/or treatment, e.g., of an infection or pathological condition. The step of "determining" encompasses detecting or quantifying, wherein "detecting" means determining if the target analyte is present or not in the biological sample and "quantifying" means determining the amount of the target analyte present in the biological sample.

The method of the invention may have therapeutic uses for example it may be used for the detection of various pathological conditions or may be used for monitoring the disease stage of a subject or its response to therapy.

In certain embodiments, the method may further comprise using statistical methods to predict the potential for detection of a target analyte to result in disease or progression of disease and/or to permit prognosis of disease (i.e., prediction of the course of a disease).

In certain embodiments, the method may be carried out across a group of population of patients, e.g., in order to permit stratifying the approach to treatment thereof or to satisfy a public health or other monitoring goal.

In one embodiment, a method is disclosed for monitoring the efficiency of a therapeutic regimen in a subject suffering from a pathological condition comprising using the methods and/or system disclosed herein wherein said target molecule is an antigen associated with the pathological condition and wherein the amount of said detectable moiety is indicative of the level of the pathological condition and thereby of the efficiency of the therapeutic regimen in the subject.

In certain embodiments, the method comprises monitoring the effectiveness of one more therapeutic agents (e.g., anti-viral agents, anticancer agents, etc.) over a period of time (e.g., days, weeks) and permits the user to seek an alternative therapeutic approach if the therapeutic agent is not sufficiently effective over a period of time.

In one embodiment, if the treatment regime does not produce a reduction in condition within a defined period (e.g., days), the user may discontinue the treatment regime in favor of an alternative treatment regime or in certain embodiments, supplement the treatment regime with a second treatment regime. In one embodiment, the system permits obtaining two or more results, three or more results or five or more results with respect to the quantity of a target analyte for the same user at different times, to permit monitoring of a trend in analyte level over time.

In one embodiment, the method comprises (i) providing a biological sample from a subject, wherein the biological sample is blood; (ii) adding the biological sample to a test strip, wherein the strip contains a first, second, and third binding agent capable of create a detectable complex with at least one target analyte in the biological sample, if present; (iii) incubating the detectable complex with a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, saliva, sweat, ocular fluid including aqueous humor, blood, fecal matter, sebum, respiratory droplets, semen, vaginal mucus, cerumen, epidermal cells, nasal sample, cerebral spinal fluid, pleural effusion, or nasopharyngeal specimens; (ii) swabbed biological sample; (iii) adding the biological sample to a test strip, wherein the strip contains a first, second, and third binding agent capable of create a detectable complex with at least one target analyte in the biological sample, if present; (iv) incubating the detectable complex with a dye such as 3,3',5,5-tetramethylbenzidine on the strip; (v) detecting the level of detectable complex, if any, in the form a color change, and (vi) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is blood, in a tube which dilutes the biological sample by 1× to 1,000,000,000× and contains the second binding agent; (ii) adding the biological sample to a test strip, wherein the strip contains a first, second, and third binding agent capable of create a detectable complex with at least one target analyte in the biological sample, if present; (iii) incubating the detectable complex with a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, sweat, ocular fluid including aqueous humor, blood, fecal matter, sebum, respiratory droplets, semen, vaginal mucus, cerumen, epidermal cells, or nasopharyngeal specimens, in a tube which dilutes the biological sample by 1× to 1,000,000,000× and contains the second binding agent; (ii) adding the biological sample to a test strip, wherein the strip contains a first, second, and third binding agent capable of create a detectable complex with at least one target analyte in the biological sample, if present; (iii) incubating the detectable complex with a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) providing a biological sample from a subject, wherein the biological sample is blood; (ii) adding the biological sample to a test strip, wherein the test strip contains a first, and third binding agent capable of create a detectable complex with at least one target analyte in the biological sample, if present, if present, in the biological sample in competition with the target analyte conjugated to glucose oxidase; (iii) incubating the detectable complex a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, saliva, sweat, ocular fluid including aqueous humor, blood, fecal matter, sebum, respiratory droplets, semen, vaginal mucus, cerumen, epidermal cells, nasal sample, cerebral spinal fluid, pleural effusion, or nasopharyngeal specimens; (ii) swabbed biological sample; (iii) adding the biological sample to a test strip, wherein the test strip contains a first, and third binding agent capable of create a detectable complex with at least one target analyte in the biological sample, if present, if present, in the biological sample in competition with the target analyte conjugated to glucose oxidase; (iv) incubating the detectable complex with a dye such as 3,3',5,5-tetramethylbenzidine on the strip; (v) detecting the level of detectable complex, if any, in the form a color change, and (vi) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is blood, in a tube which dilutes the biological sample by 1× to 1,000,000,000× and contains the second binding agent; (ii) adding the biological sample to a test strip, wherein the test strip contains a first, and third binding agent capable of create a detectable complex with at least one target analyte in the biological sample, if present, if present, in the biological sample in competition with the target analyte conjugated to glucose oxidase; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

In one embodiment, the method comprises (i) collecting a biological sample from a subject, wherein the biological sample is urine, sweat, ocular fluid including aqueous humor, blood, fecal matter, sebum, respiratory droplets, semen, vaginal mucus, cerumen, epidermal cells, or nasopharyngeal specimens, in a tube which dilutes the biological sample by 1× to 1,000,000,000× and contains the second binding agent; (ii) adding the biological sample to a test strip, wherein the test strip contains a first, and third binding agent capable of create a detectable complex with at least one target analyte in the biological sample, if present, if present, in the biological sample in competition with the target analyte conjugated to glucose oxidase; (iii) incubating the detectable complex with horseradish peroxidase and a dye such as 3,3',5,5-tetramethylbenzidine on the strip; (iv) detecting the level of detectable complex, if any, in the form a color change, and (v) calibrating the level of the detectable complex, if produced, with the quantity of the target analyte in the at least one biological sample, if any, thereby providing a diagnostic assessment.

The therapeutic agent may vary. In one embodiment, the therapeutic agent is an agent such as a small molecule, protein, virus, bacteria nucleic acid, or biologic agent.

In one embodiment of the methods disclosed herein, the result has a specificity of about 90% or more, or more particularly, about 91% or more, about 92% or more, about 93% or more, about 94% or more, about 95% or more, about 96% or more, about 97% or more, about 98% or more, about 99% or more.

In one embodiment of the methods disclosed herein, the result has a selectivity of about 90% or more, or more particularly, about 91% or more, about 92% or more, about 93% or more, about 94% or more, about 95% or more, about 96% or more, about 97% or more, about 98% or more, about 99% or more.

In one embodiment of the methods disclosed herein, the result has an accuracy of about 90% or more, or more particularly, about 91% or more, about 92% or more, about 93% or more, about 94% or more, about 95% or more, about 96% or more, about 97% or more, about 98% or more, about 99% or more.

The methods disclosed herein are not limited to the steps described above and may comprise supplemental steps, either carried out before, after or between the steps described.

III. Methods of Preparation

Also disclosed are methods of preparing generic test strips or substrates for use in the systems and assays disclosed herein. The test strip can be manufactured using any suitable method. In one embodiment, the test cassette or trip is manufactured using injection molding or a roll to roll process, a screen-printing process, a drop-cast process or combinations thereof.

In one embodiment, a method is providing for producing a test strip for use in a diagnostic or detection system or assay such as those disclosed herein comprising (i) providing a membrane; (ii) binding a first binding agent to the membrane (e.g., streptavidin) and (iii) optionally, crosslinking the first binding agent to one or more additional first binding agents.

In a specific embodiment, the first binding agent is cross-linked to one or more additional binding agent by means of a polymer (e.g., PEG).

IV. Kits

Also disclosed are kits for carrying out the methods disclosed herein.

In one embodiment the kit comprises the assay disclosed herein, either as a standalone assay or part of the disclosed system. In certain embodiments, the kit includes multiple assays. In certain embodiments, the kit includes the detection device (e.g., glucometer).

Test cassettes or strips compositions as disclosed herein may be combined with other ingredients or reagents or prepared as components of kits or other retail products for commercial sale or distribution.

The kits of the invention may comprise a test strip or other solid support. In certain embodiments, the kit comprises a lateral or vertical flow test strip which may be provided as a separate element or on one or more of the binding agents are already found. In one embodiment, the lateral or vertical flow strip may comprise the first binding agent (e.g., streptavidin or avidin) bound thereto. Optionally, the first binding agent may be present on the lateral or vertical flow strip provided in the kit in cross-linked form.

Typically, the kits described above will also comprise one or more other containers, containing for example, wash reagents, and/or other reagents capable of quantitatively detecting the presence of bound target analyte.

The detecting agent and optionally, reporting agent may unlabeled or labeled.

Where the label is an enzyme, the kit may include substrates and cofactors required by the enzyme. In certain embodiments, the kit may contain a quantity of sugar (e.g., glucose) to be added to the assay by the user. If the label is a fluorophore, the kit may include a dye precursor that provides the detectable chromophore.

In a particular embodiment, the comprise a sealed, disposable cup with dried recognition elements in it (e.g., the capture agent, the detection agent. A compartmentalized kit includes any kit in which reagents are contained in separate containers, such as plastic containers. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the antibody(s) used in the assay, containers which contain wash reagents (such as phosphate buffered saline, Tris-buffers, and like), and containers which contain the detection reagent.

In certain embodiments, the kit may include a disposable dropper, dropper bottles for buffers, reagents, blotting/wicking material(s) and disposable test.

In certain embodiments, the kit components may be foil or paper packed, and may include desiccant.

The kit may also contain instructions for carrying out the assay, and/or a reference standard (e.g., purified collagen VII, e.g., recombinantly produced collagen VII), as well as other additives such as stabilizers, washing and incubation buffers, and the like. The kit will also contain instructions regarding administration and/or use of the kit.

The kit may also contain a reader.

In certain embodiments, the kit allows (i) the detection of the at least one target analyte at a limit of detection of about of about 1 target analyte per milliliter to >100,000 target analytes per milliliter; (i) the detection of the at least one target analyte with about 90% accuracy and/or (iii) provides a result in about 10 minutes or less, about 5 minutes or less, about 2 minutes or less or about 1 minute or less.

EXAMPLES

Example 1: Electrochemical Detection of H1N1

As shown in FIG. 14, a protocol is described which enables electrochemical detection of H1N1 via functionalized nitrocellulose strips above a working electrode in a 3 electrode detection system. The physical setup is shown on the bottom left and the chronoamperometric result is shown on the bottom right. Runs with virus indicate higher currents than that of controls curves wherein no virus is present.

Example 2: Electrochemical Detection of SARS-Cov-2

Figure 15:
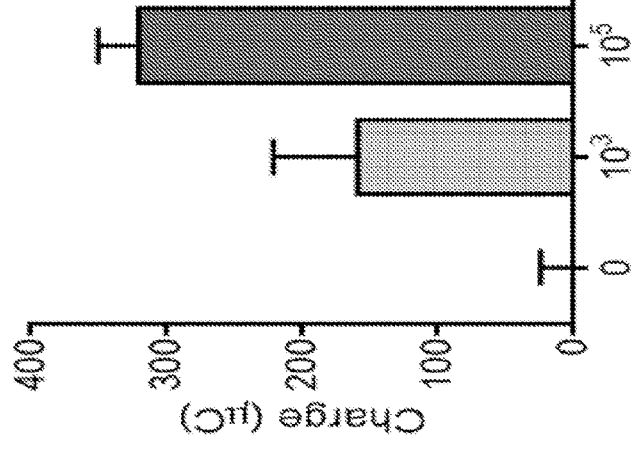
FIG. 15 shows a plot of electrochemical detection of two different SARS-CoV-2 concentrations. The three bars indicate viral concentrations [virus] as a number in pfu/mL, 0, 10E3 and 10E5.

As shown in FIG. 15, electrochemical detection of SARS-CoV-2 via functionalized nitrocellulose strips above a working electrode in a 3 electrode detection system reveals higher cumulative charge as calculated by the area under the chronoamperometric curve with higher virus titer.

Example 3: Electrochemical Detection of SARS-Cov-2

As shown in FIG. 16, specificity of electrochemical detection of SARS-CoV-2 via functionalized nitrocellulose strips above a working electrode in a 3 electrode detection system was compared by using the same assay for cross reactivity against RSV, OC43 and H1N1.

Example 4: Colorimetric Detection of H1N1

Figure 17:
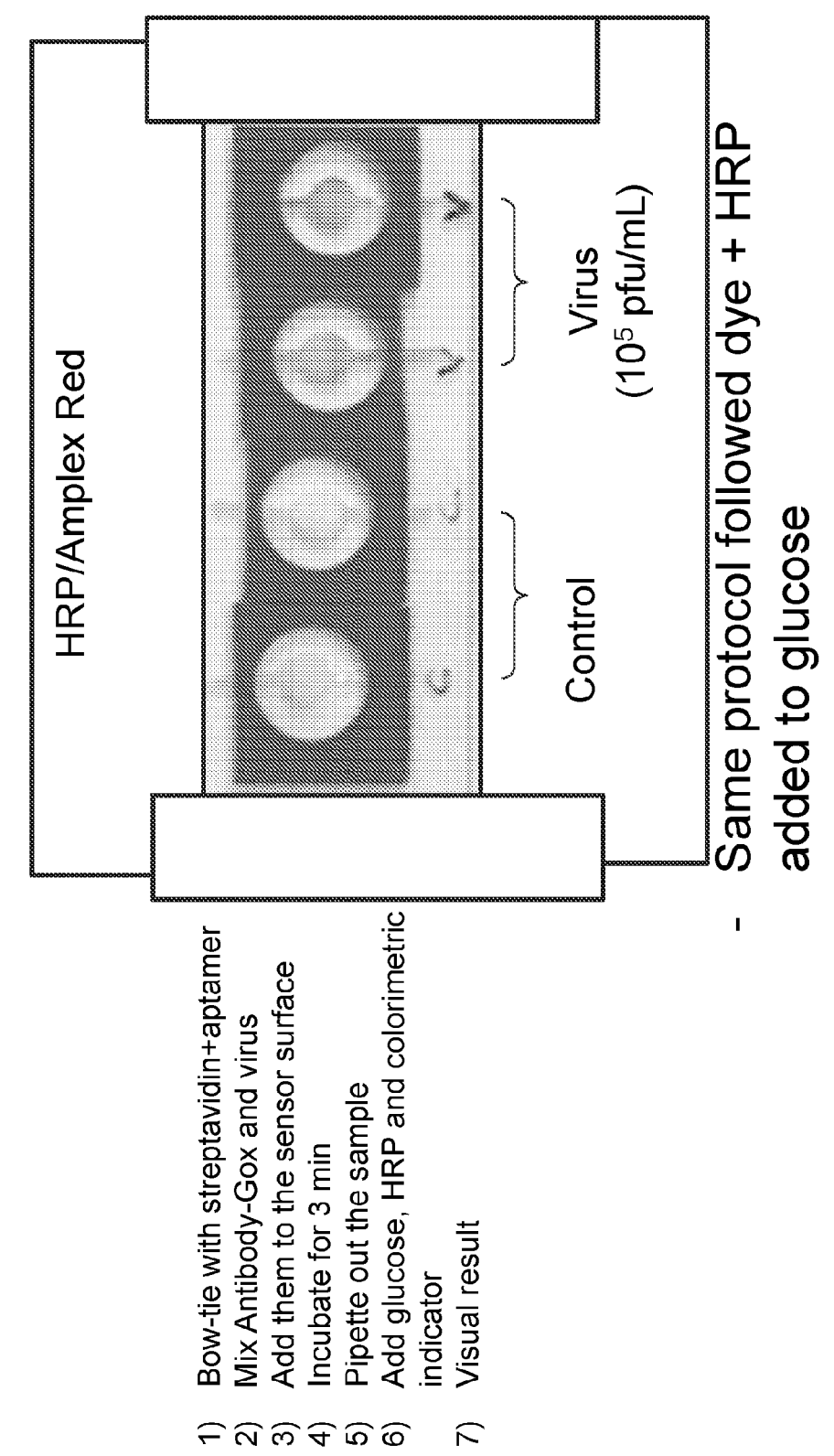
FIG. 17 shows a protocol for and an example of colorimetric detection of H1N1

As shown in FIG. 17, the same assay as described in EXAMPLE 1 was used to colorimetrically detect H1N1 by adding redox mediators and dyes to the glucose solution described herein. The glucose solution, when in the presence of target bound oxidase, results in hydrogen peroxide generation. As opposed to detection of the charge via electrochemical means, addition of HRP and Amplex Red, for example, result in a pink color.

Example 5: Colorimetric Detection of H1N1

As shown in FIG. 18, specific conditions are described that were used to colorimetrically detect H1N1 by adding redox mediators and dyes to the glucose solution described herein. The glucose solution, when in the presence of target bound oxidase, results in hydrogen peroxide generation. As opposed to detection of the charge via electrochemical means, addition of HRP and TMB or Amplex Red result in a blue or pink color, respectively.

Example 6: Colorimetric Detection of OPN

As shown in FIG. 19, specific conditions are described that were used to colorimetrically detect osteopontin by adding TMB and HRP to the glucose solution above the sandwich bound target complex.

Example 7: Colorimetric Detection of OPN

As shown in FIG. 20, more specific conditions are described that were used to colorimetrically detect osteopontin by adding TMB and HRP to the glucose solution above the sandwich bound target complex.

Example 8: Cross Linked Streptavidin

For the electrochemical detection of an analyte using a sandwiched sensing assay, streptavidin coated beads will be loaded, by dropcasting 10 μL of the solution in PBS, in a nitrocellulose membrane (e.g., with 0.45 μm pores was purchased from Thermoscientific). Next, a PEG of 3400 Mw chemically modified to contain two terminal biotins will be added to the nitrocellulose membrane. The ratio of streptavidin to biotin is 1:0.25. Next the membrane will be washed using 200 μL PBST and transferred to DropSens 710 electrodes. An antibody for analyte will be functionalized with biotin and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the chronoamperometric measurements will be performed after addition of 50 μL of 500 mM glucose solution.

PEG molecular weights of 1000 to 50,000, can be used but the preferred Mw is 3000-10,000. Similarly, a linear PEG with 2 biotins on the end or a Star PEG with 4 biotins on the end can be used.

For the electrochemical detection of an analyte using a sandwiched sensing assay, the nitrocellulose membrane surface and interior (4 mm diameter discs) will be functionalized with streptavidin (e.g., with 0.45 μm pores was purchased from Thermoscientific). Next, a PEG of 3400 Mw chemically modified to contain two terminal biotins will be added to the nitrocellulose membrane. The ratio of streptavidin to biotin is 1:0.25. Next the membrane will be washed using 200 μL PBST and transferred to DropSens 710 electrodes. An antibody for analyte will be functionalized with biotin and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the chronoamperometric measurements will be performed after addition of 50 μL of 500 mM glucose solution. PEG molecular weights of 1000 to 50,000, can be used but the preferred Mw is 3000-10,000. Similarly, a linear PEG with 2 biotins on the end or a Star PEG with 4 biotins on the end can be used For the optical detection of an analyte using a sandwiched sensing assay, the nitrocellulose membrane surface and interior (4 mm diameter discs) will be functionalized with streptavidin (e.g., with 0.45 μm pores was purchased from Thermoscientific). Next, a PEG of 3400 Mw chemically modified to contain two terminal biotins will be added to the nitrocellulose membrane. The ratio of streptavidin to biotin is 1:0.25. Next the membrane will be washed using 200 μL PBST. An antibody for analyte will be functionalized with biotin and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the optical measurement will be performed after addition of 50 μL of 500 mM glucose solution as well as HRP and Amplex Red. A pink/purple color forms indicating the presence of the analyte. PEG molecular weights of 1000 to 50,000, can be used but the preferred Mw is 3000-10,000. Similarly, a linear PEG with 2 biotins on the end or a Star PEG with 4 biotins on the end can be used.

For the optical detection of an analyte using a sandwiched sensing assay, streptavidin coated beads will be loaded, by dropcasting 10 μL of the solution in PBS, in a nitrocellulose membrane (e.g., with 0.45 μm pores was purchased from Thermoscientific). Next, a PEG of 3400 Mw chemically modified to contain two terminal biotins will be added to the nitrocellulose membrane. The ratio of streptavidin to biotin is 1:0.25. Next the membrane will be washed using 200 μL PBST. An antibody for analyte will be functionalized with biotin and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the optical measurement will be performed after addition of 50 μL of 500 mM glucose solution as well as HRP and Amplex Red. A pink/purple color forms indicating the presence of the analyte. PEG molecular weights of 1000 to 50,000, can be used but the preferred Mw is 3000-10,000. Similarly, a linear PEG with 2 biotins on the end or a Star PEG with 4 biotins on the end can be used.

Example 9: Cross-Linked Capture Agents

For the electrochemical detection of an analyte using a sandwiched sensing assay, streptavidin coated beads will be loaded, by dropcasting 10 μL of the solution in PBS, in a nitrocellulose membrane (e.g., with 0.45 μm pores was purchased from Thermoscientific). Next the membrane will be washed using 200 μL PBST and transferred to DropSens 710 electrodes. An antibody for analyte will be functionalized with at least two biotins and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the chronoamperometric measurements will be performed after addition of 50 μL of 500 mM glucose solution.

For the electrochemical detection of an analyte using a sandwiched sensing assay, the nitrocellulose membrane surface and interior (4 mm diameter discs) will be functionalized with streptavidin (e.g., with 0.45 μm pores was purchased from Thermoscientific). Next the membrane will be washed using 200 μL PBST and transferred to DropSens 710 electrodes. An antibody for analyte will be functionalized with at least two biotins and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the chronoamperometric measurements will be performed after addition of 50 μL of 500 mM glucose solution.

For the optical detection of an analyte using a sandwiched sensing assay, the nitrocellulose membrane surface and interior (4 mm diameter discs) will be functionalized with streptavidin (e.g., with 0.45 μm pores was purchased from Thermoscientific). Next the membrane will be washed using 200 μL PBST. An antibody for analyte will be functionalized with at least two biotins and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the optical measurement will be performed after addition of 50 μL of 500 mM glucose solution as well as HRP and Amplex Red. A pink/purple color forms indicating the presence of the analyte.

For the optical detection of an analyte using a sandwiched sensing assay, streptavidin coated beads will be loaded, by dropcasting 10 μL of the solution in PBS, in a nitrocellulose membrane (e.g., with 0.45 μm pores was purchased from Thermoscientific). Next the membrane will be washed using 200 μL PBST. An antibody for analyte will be functionalized with at least two biotins and a second different antibody for the analyte will be conjugated with GOx (Ab-GOx), synthesized using Abcam's Lightning-Link (GOx conjugate kit, #ab102887). The analyte and two antibodies will be mixed together and then 5 μL of this solution will be drop-casted and spread on the membrane surface and incubated for 5 min. The membrane will be washed using 200 μL PBST and the optical measurement will be performed after addition of 50 μL of 500 mM glucose solution as well as HRP and Amplex Red. A pink/purple color forms indicating the presence of the analyte.

Example 10. Electrochemical Prototype

Figure 21:
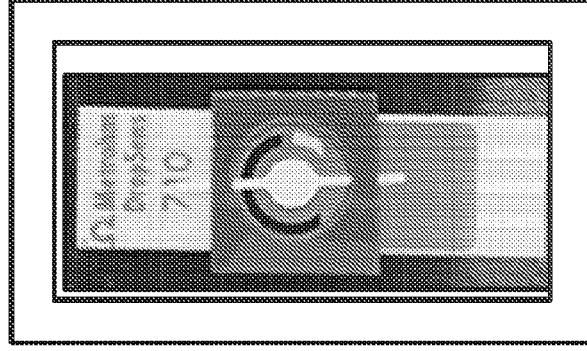
FIG. 21 shows a schematic of a top view of an electrochemical disposable test prototype.

As shown in FIG. 21, a schematic of a top view of an electrochemical disposable test prototype. This schematic comprises a waterproof barrier surrounding a 3 electrode system on a waterproof base and an immobilization region atop the working electrode.

Example 11. Optical Prototype

Figure 22:
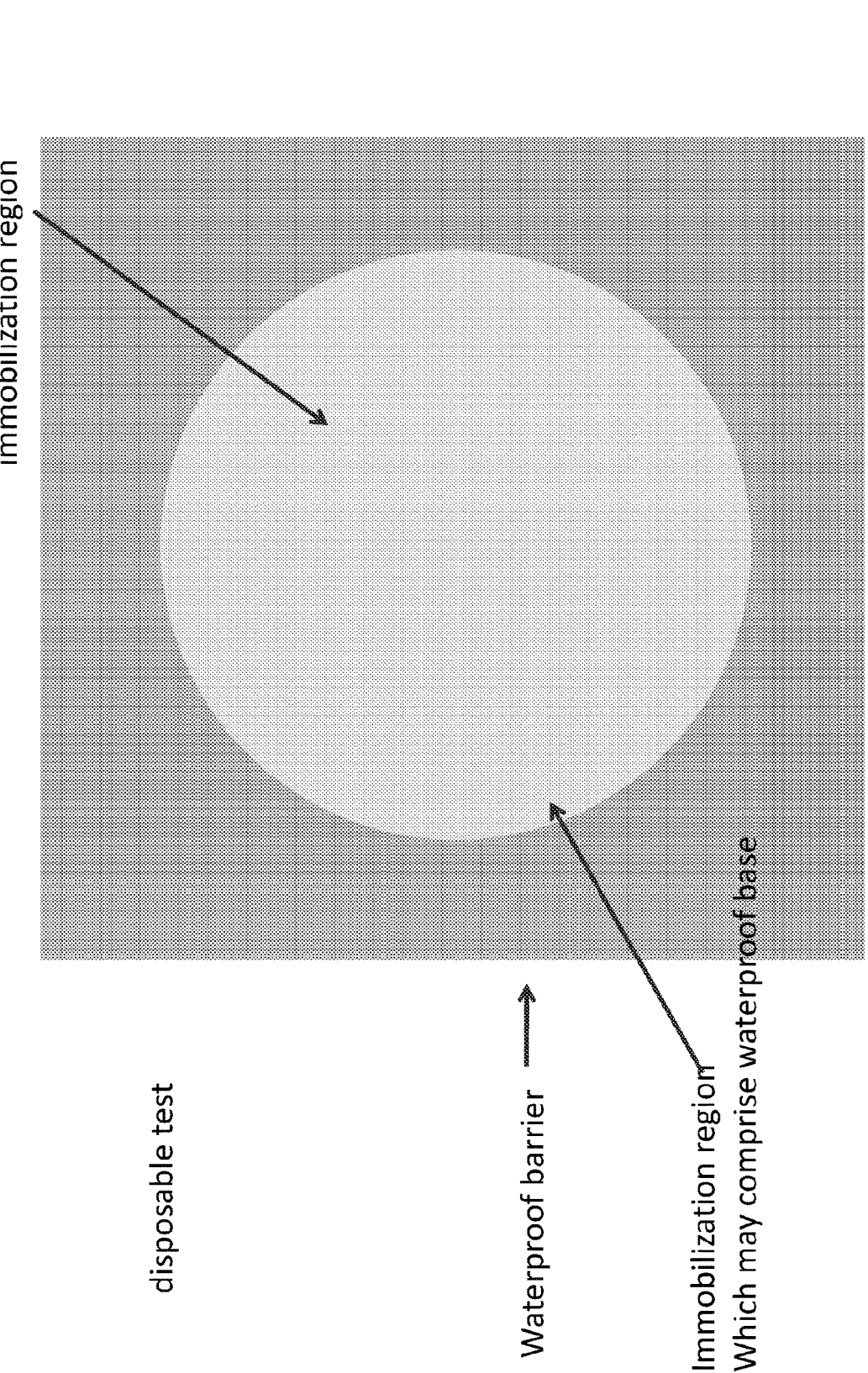
FIG. 22 shows a schematic of a top view of an optical disposable test prototype.

As shown in FIG. 22, a schematic of a top view of an optical disposable test prototype. This schematic comprises a disposable optical/colorimetric test prototype comprising a waterproof barrier surrounding an immobilization region atop of a waterproof base material. The waterproof barrier creates a chamber which lies within the waterproof barrier.

Example 12. Optical Prototype

Figure 23:
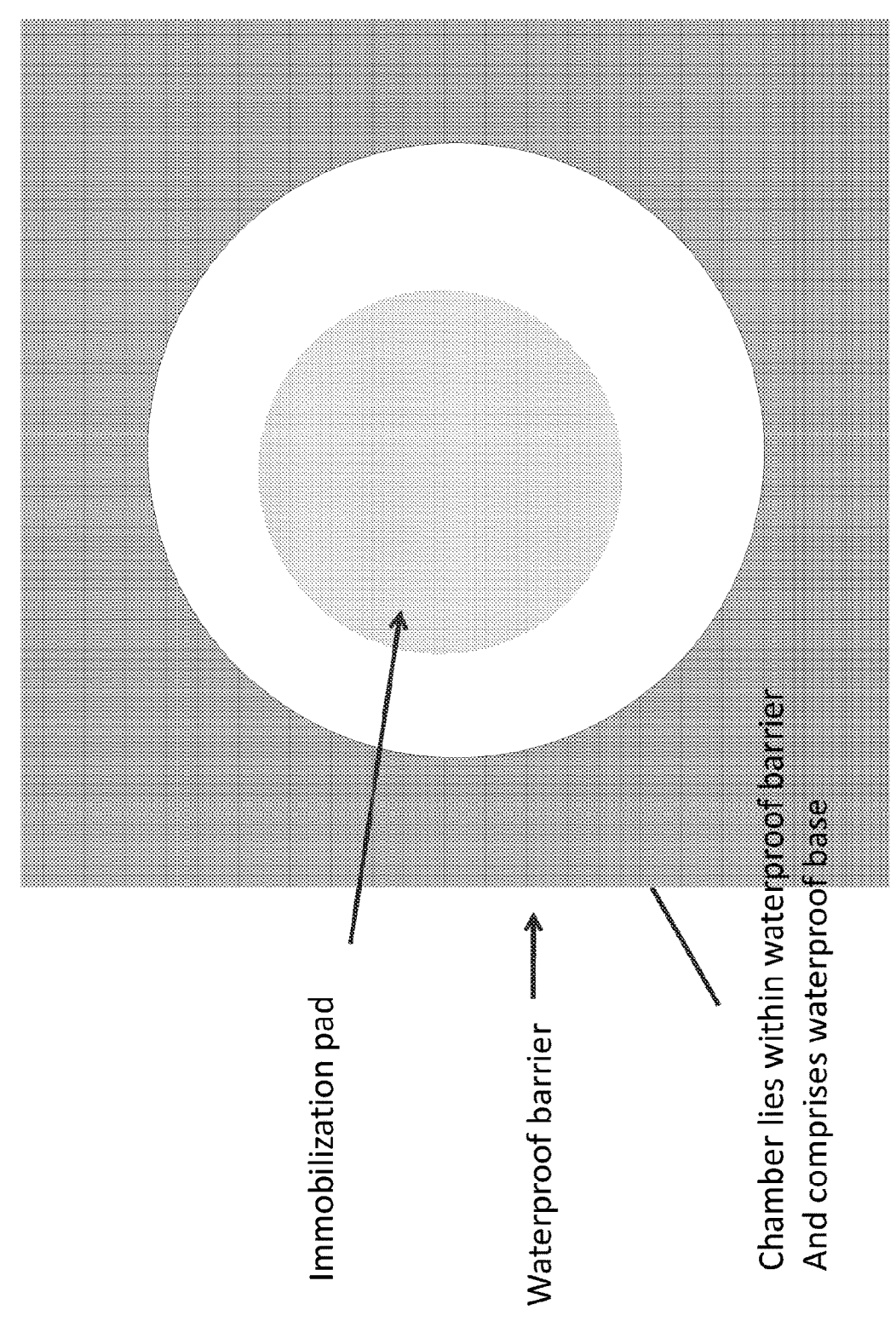
FIG. 23 shows a schematic of a top view of another optical disposable test prototype.

As shown in FIG. 23, a schematic of a top view of another optical disposable test prototype. This schematic comprises a disposable optical/colorimetric test prototype comprising a waterproof barrier surrounding an immobilization region placed on a waterproof base. The waterproof barrier creates a chamber which lies within the waterproof barrier.

Example 13. Optical Prototype

Figure 24:
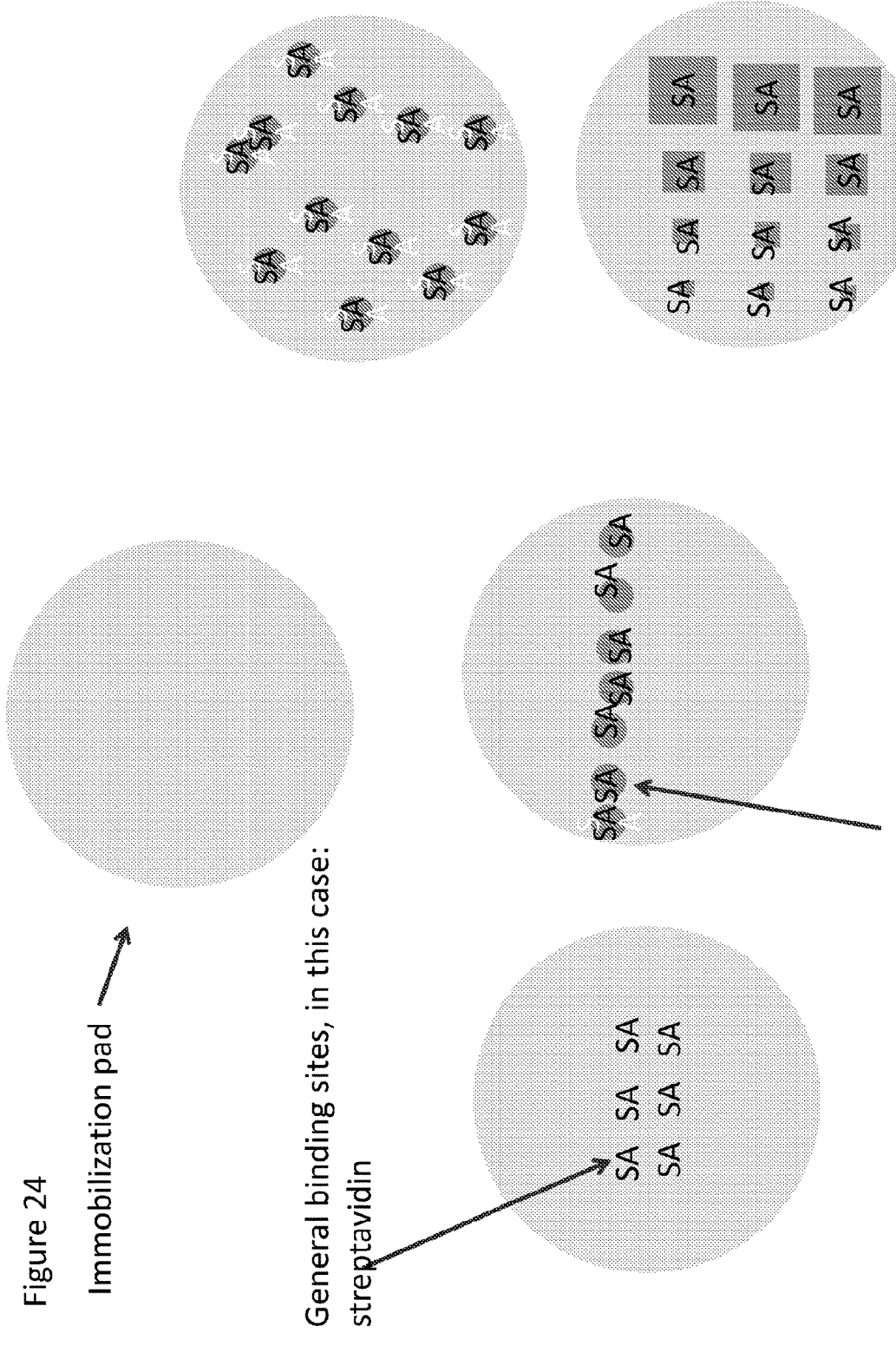
FIG. 24 shows a schematic of a top view of an immobilization region.

As shown in FIG. 24, a schematic of a top view of an immobilization region is shown. The immobilization region may have, for example, streptavidin as generalized binding sites that may be in the form of lines, an entire region, gradients, patterns, topographies, etc. that may assist in quantification of target.

Example 14. Optical Prototype

Figure 25:
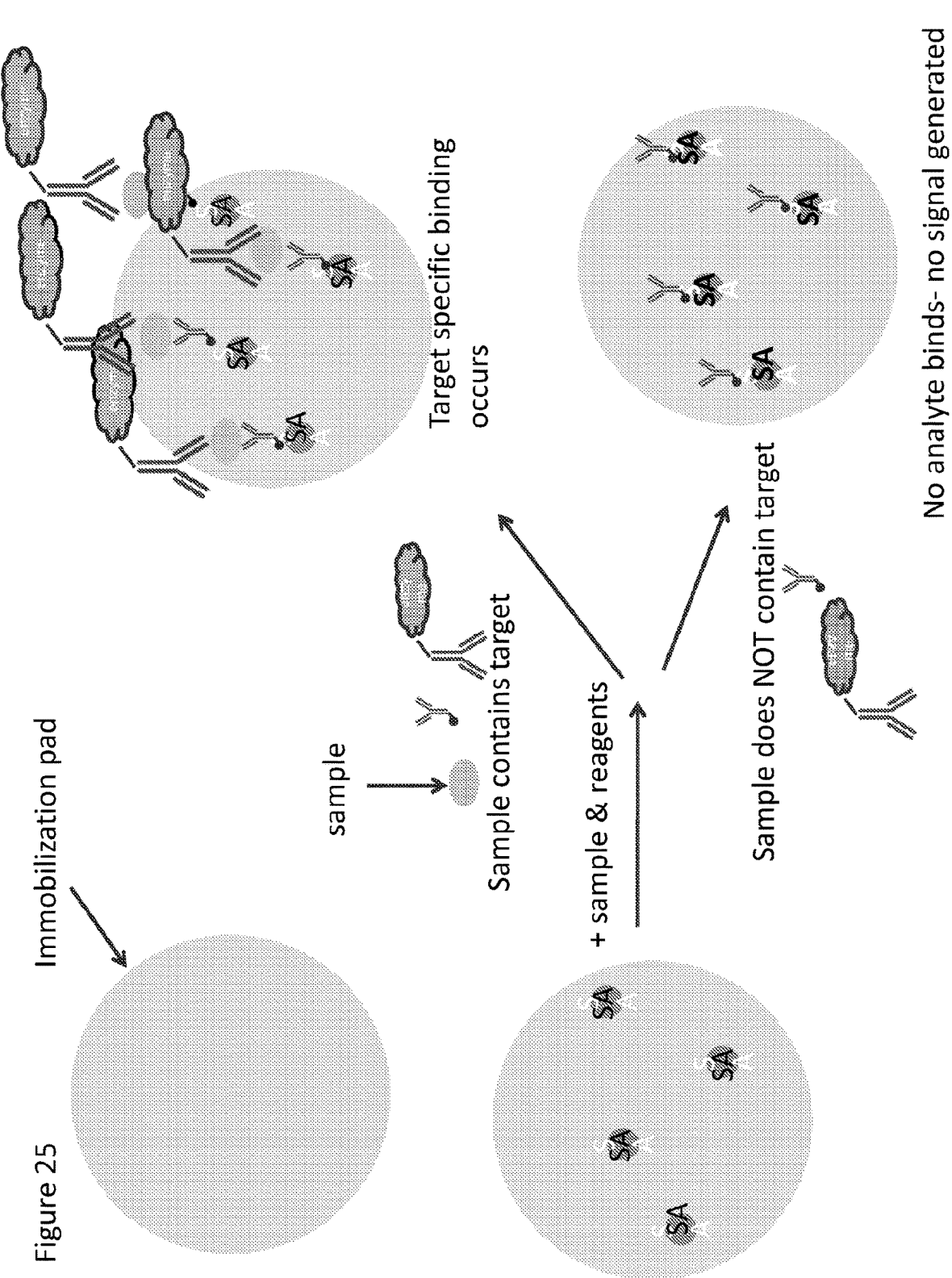
FIG. 25 shows a schematic of a top view of another immobilization region.

As shown in FIG. 25, a schematic of a top view of another immobilization region. The immobilization region may include generalized binding sites, such as via direct immobilization of streptavidin, or via streptavidin coated polystyrene beads. The generalized binding sites on the immobilization region may be exposed to a solution of antibodies, for example, biotinylated antibodies, as well as enzyme labeled antibodies, specific for an analyte of interest. If the analyte of interest is included in the solution/sample solution, the antibodies both may bind the target analyte and generate a detectable complex on/above the immobilization region. If the analyte of interest is not included, a detectable complex is not immobilized to the immobilization region.

Example 15

Figure 36:
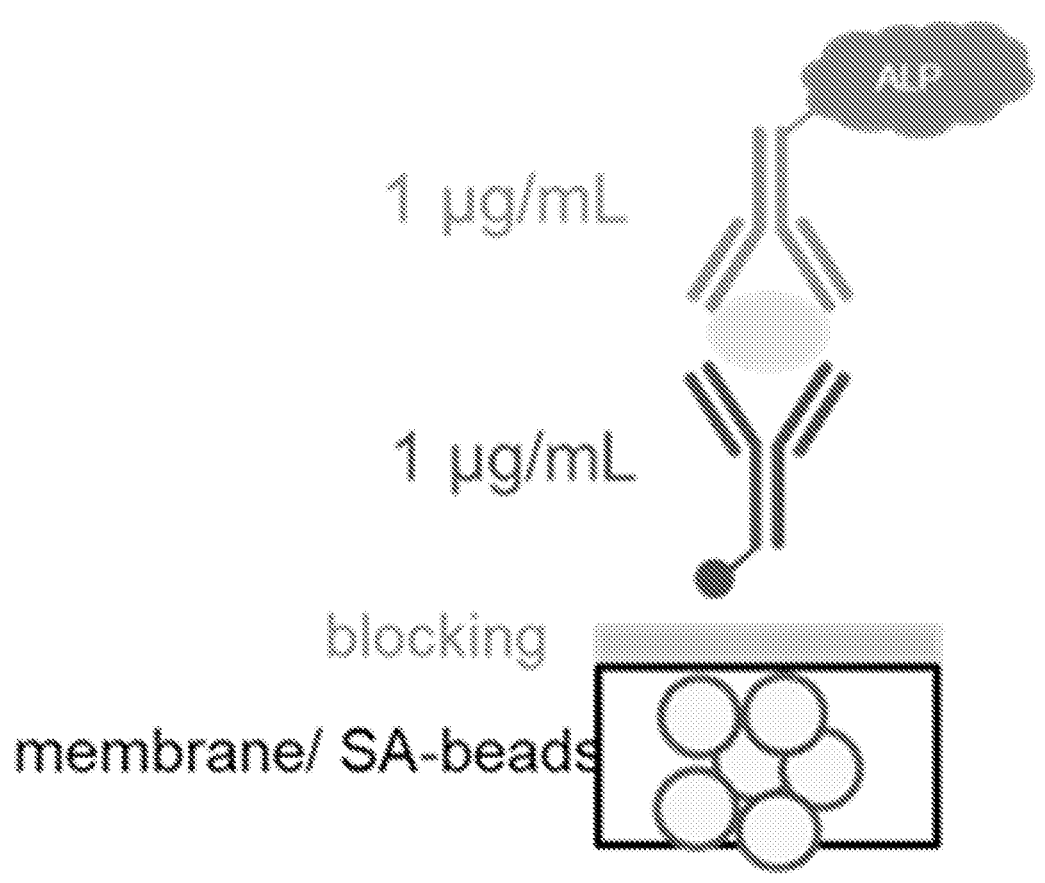
FIG. 36 shows a sandwich assay configuration for detection of IL-6. A complex is formed around the IL-6 target via two antibodies, one labeled with an enzyme, alkaline phosphatase, and one labeled with biotin. In this example, the biotin moiety binds tightly to streptavidin labeled beads embedded in a membrane, which may be blocked.
Figure 37:
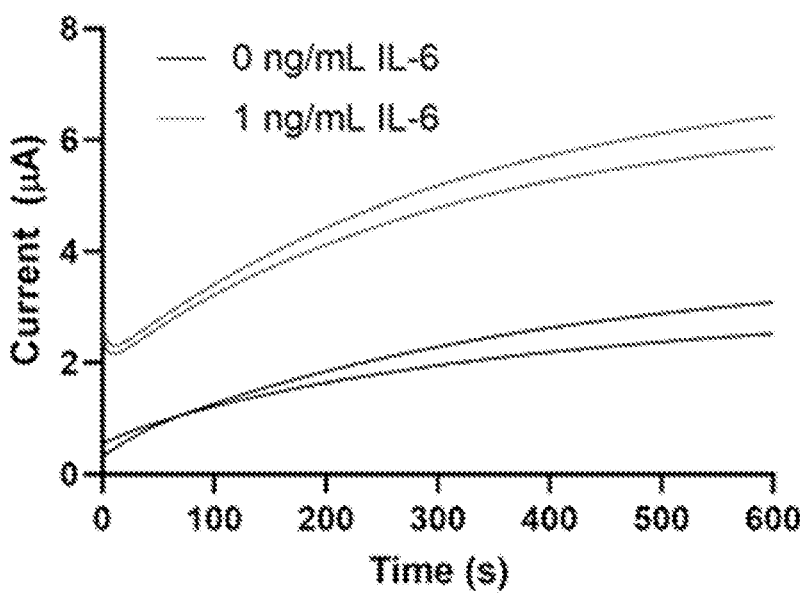
FIG. 37 shows standard chronoamperometric detection of IL-6 over 10 min using alkaline phosphatase as the detection enzyme.
Figure 38:
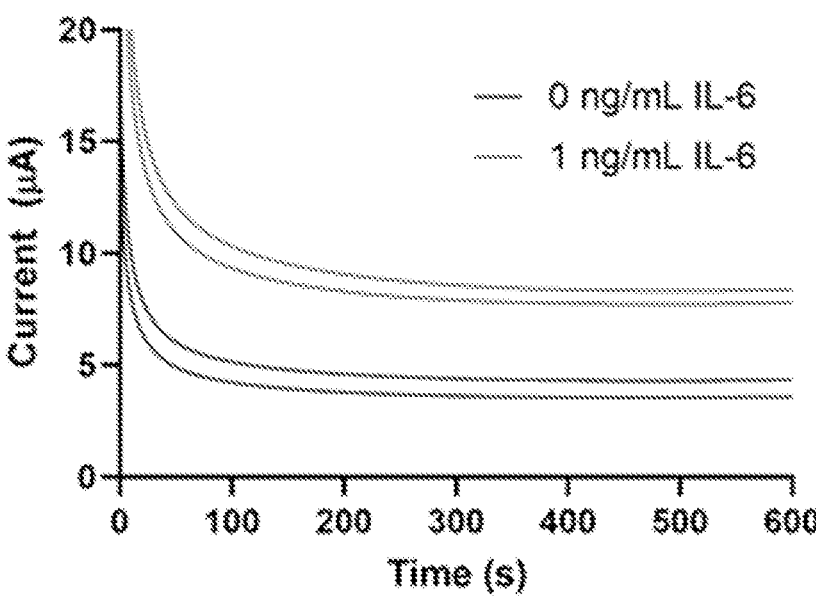
FIG. 38 shows chronoamperometric detection of IL-6 10 min after data in FIG. 37 was acquired (same electrode, 10 min pause, then overpotential reapplied over 10 min.

A solution containing 1 µg/mL TL-6 antibody bound to alkaline phosphatase, 1 µg/mL biotinylated IL-6 antibody, and IL-6 protein at 1 ng/mL or 0 ng/ml was prepared in assay buffer. A region of streptavidin-coated beads embedded in a lateral flow membrane sat atop an electrode. 15 ul of the test or control solution was added to a lateral flow membrane (FIG. 36). Solution flowed across the membrane. After 2 minutes, the membrane was washed with 200 uL buffer, which was collected via a wicking pad. 100 uL 20 mM 4-aminophenyl phosphate/diethanolamine substrate (pH 9.6) was then deposited on the membrane region atop the electrode and chronoamperometry was run. The first plot indicates the chronoamperometric result collected during 10 minutes (2 test and 2 control runs were performed; FIG. 37). The second plot indicates the chronoamperometric result collected on the same electrodes after 20 minutes (FIG. 38).

Example 16. Protype Cartridge

A prototype cartridge that affords sample collection, flow to target binding site, which is in contact with electrode(s), waste and substrate solution reservoirs, is shown in FIG. 39. The cartridge may be inserted into a virometer for electrochemical detection.

Example 17

Figure 26:
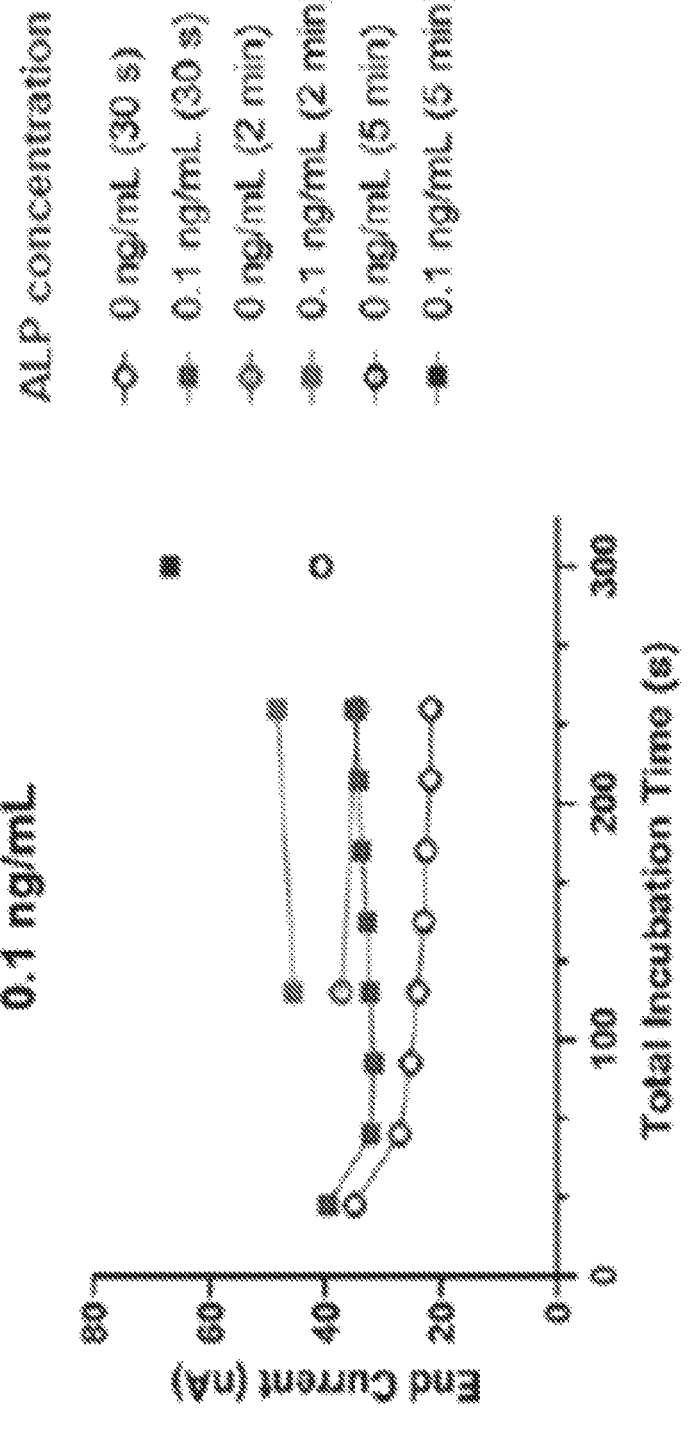
FIG. 26 shows final (end) current at 10 sec versus total incubation time of either 0 or 0.1 ng/ml ALP activity in APP/DEA buffer system.
Figure 27:
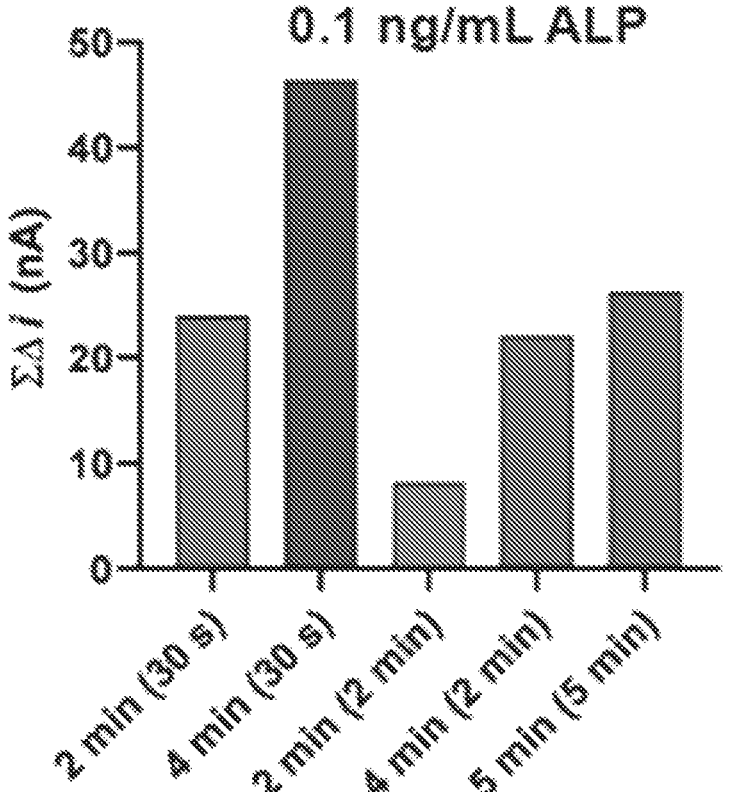
FIG. 27 shows cumulative current in nA as a function of total measurement time and measurement time interval period.

Alkaline phosphatase (ALP) was dissolved in diethanolamine (DEA) buffer to ten times targeted measurement concentration. 5 uL of the solution was applied to an electrode followed by 45 uL of substrate solution (10 mM 4-aminophenyl phosphate (APP)/DEA (1 M)+5 mM MgCl$_2$. Enzyme and substrate (ALP and APP) were incubated for various detection intervals ranging from 30 s to 5 min followed by 10-second chronoamperometric detection. For the 30 s intervals, a 0.2 V (vs. Ag) potential was applied for 10 sec and current was measured following an initial 30 s incubation. After the measurement, the cell was held at open circuit for 20 more seconds before repeating the 10-second measurement. This detection pattern was repeated for a period up to 240 s (eight intervals). For the 2 min detection intervals incubation, the 10-second chonoamperometry measurement was performed every 2 minutes for a period up to 240 s, or two intervals with the cell at open circuit for 110 seconds in between. For the 5 min detection interval, only one round of 10-second chronoamperometric detection was performed. Final (end) current at 10 sec is plotted versus the total incubation time of either 0 or 0.1 ng/ml ALP activity in APP/DEA buffer system (FIG. 26). Note that the background (0 ng/ml) end current decreases over time, whereas enzyme activity may initially decrease, but then increases over time. Repeated chronoamperometric detection shortens the total required measurement time to reach a desired current distinction, as shown in FIG. 27 comparing cumulative current in nA as a function of total measurement time and measurement time interval period.

Example 18

Figure 28:
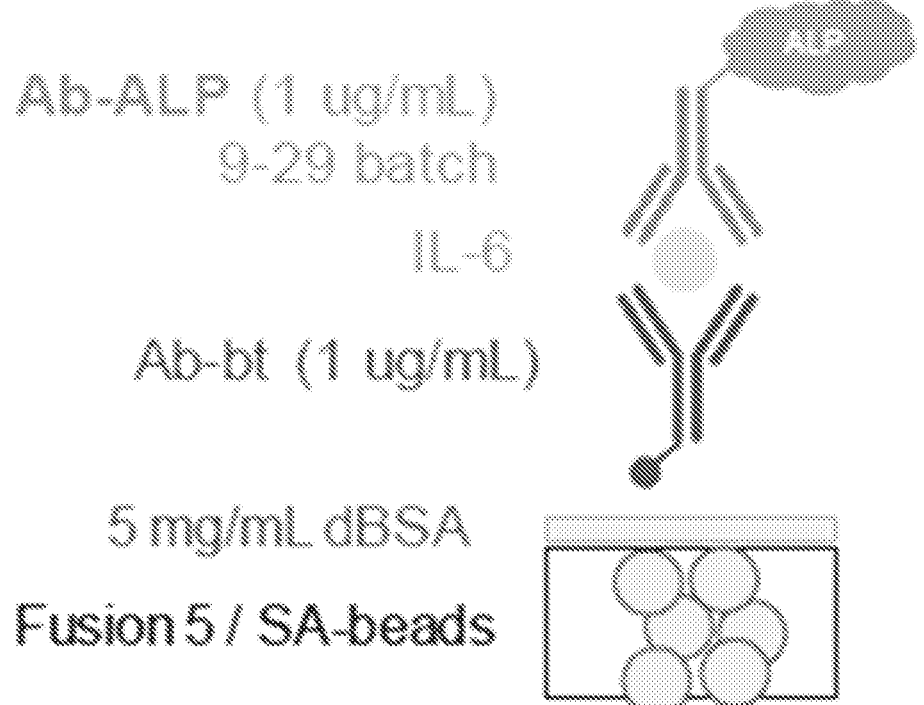
FIG. 28 shows a sandwich assay configuration for detection of IL-6.
Figure 29:
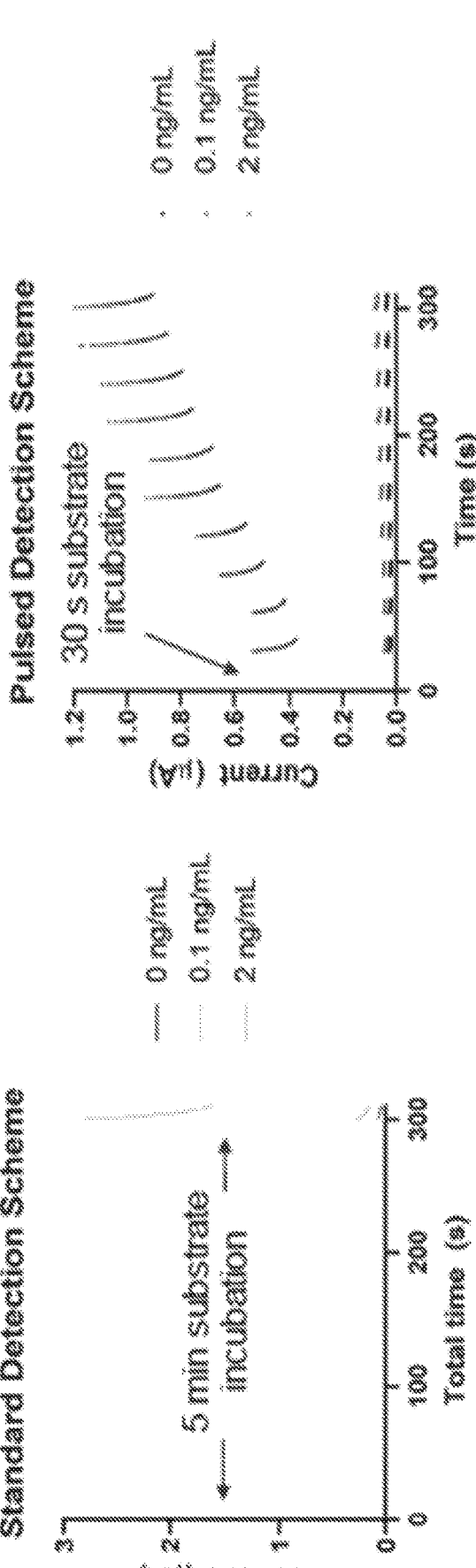
FIG. 29 shows a standard chronoamperometric detection and modified chronoamperometric detection schemes relying on either 5 min or 30 sec interval incubation periods before 10 sec acquisition time.
Figure 30:
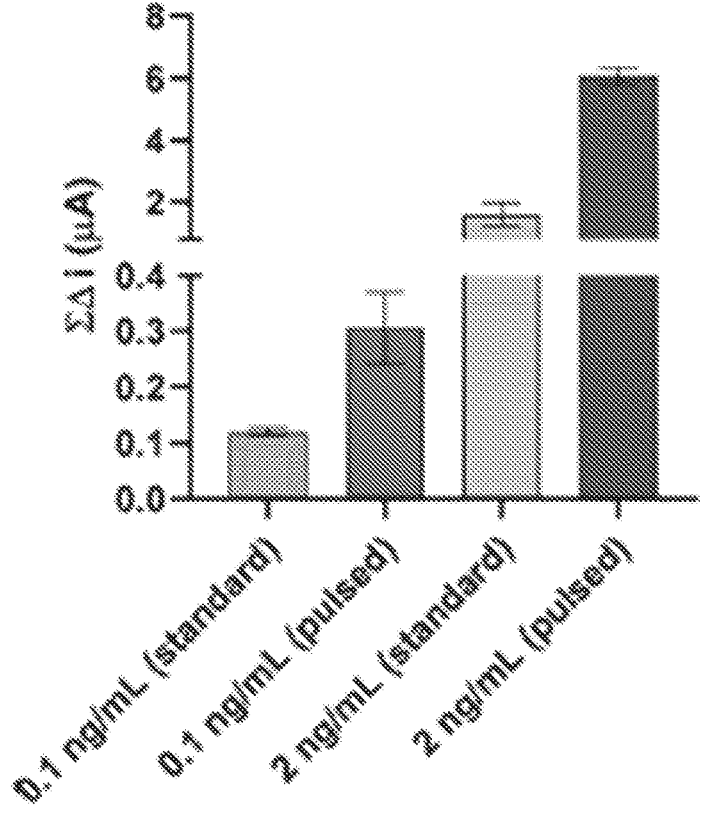
FIG. 30 shows a cumulative current difference in modified chronoamperometric detection as a function of IL-6 concentration.

A solution containing 1 µg/mL anti-IL-6 antibody bound to alkaline phosphatase, 1 g/mL biotinylated anti-IL-6 antibody, and IL-6 protein at 2 ng/ml, 0.1 ng/mL or 0 ng/ml was prepared in assay buffer. A region of streptavidin-coated beads embedded in a lateral flow membrane sat atop an electrode. 100 ul of the test or control solution was added to a lateral flow membrane. Solution flowed across the membrane. After 2 minutes, the membrane was washed with 200 uL buffer, which was collected via a wicking pad. 60 uL of 10 mM 4-aminophenyl phosphate/diethanolamine substrate (pH 9.8) was then deposited on the membrane region atop the electrode to measure concentration of IL-6 captured in a sandwich configuration (FIG. 28). In one case, chronoamperometry was run for 10 sec following 5 min substrate incubation. In another case, modified chronoamperometry was run by repeated application of a 0.2 V (vs Ag) potential (measuring current over these 10 seconds) every 30 s after introduction of the substrate solution for a total duration of 310 sec (FIG. 29) Results show 2.5-fold higher cumulative current distinction for modified chronoamperometric detection at 0.1 ng/ml and 3.8-fold higher cumulative current distinction for 2 ng/ml (FIG. 30) as compared to the single 10-second detection after a 5-minute incubation.

Example 19

Figure 31:
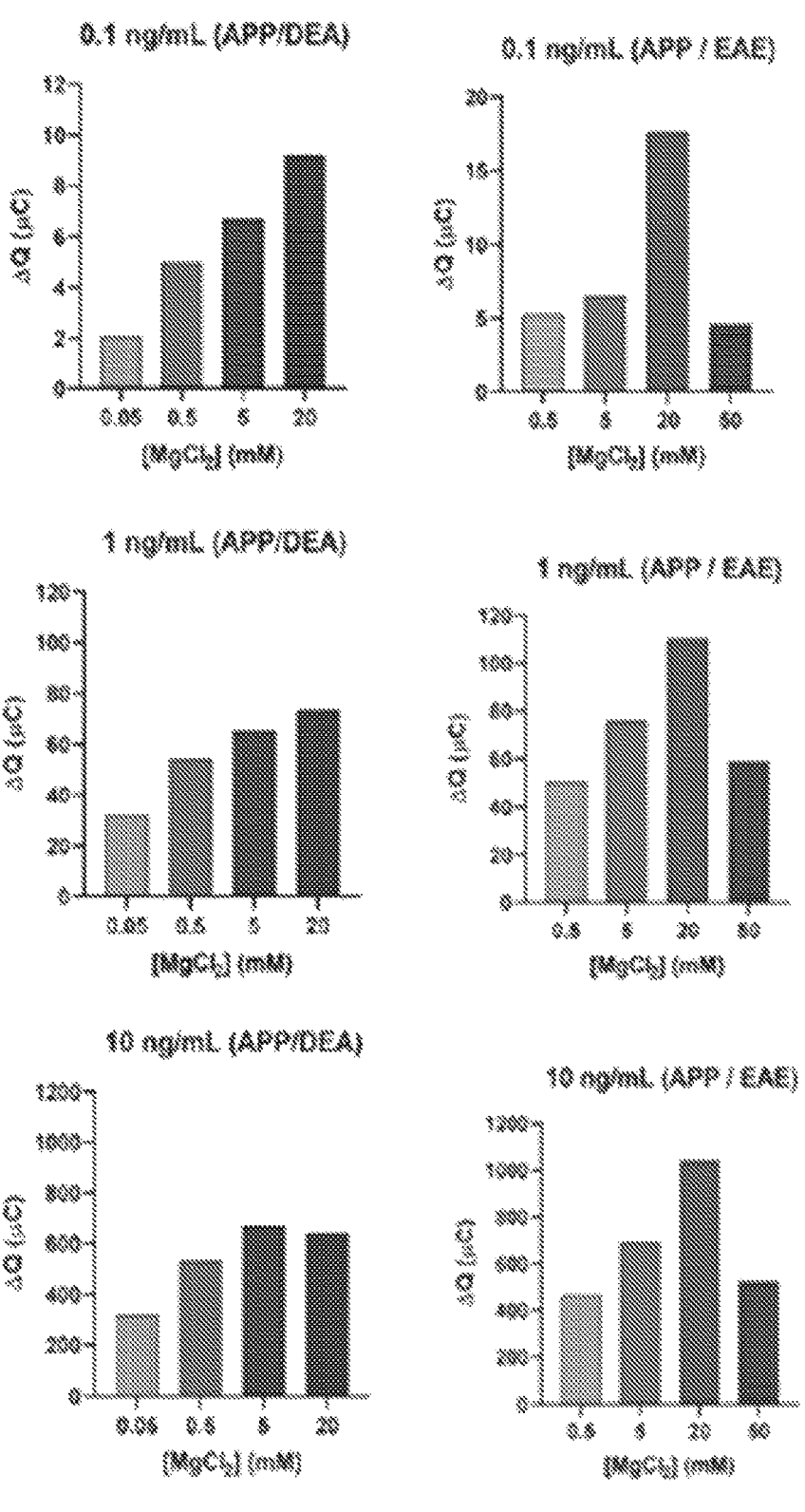
FIG. 31 shows a change in measured charge for 10 ng/ml ALP in APP/DEA as a function of varying concentration of $MgCl_2$. Concentrations of 0.0, 0.1 and 2 ng/ML TL-6 are shown in plots of current versus time.

Bovine sourced alkaline phosphatase (ALP) was dissolved in diethanolamine (DEA) buffer to ten times targeted measurement concentration. 5 uL of the solution was applied to an electrode followed by 45 uL of substrate solution (10 mM 4-aminophenyl phosphate (APP)/DEA or APP/2-(ethylamino)ethanol (EAE) with varying amounts of MgCl2. Enzyme and substrate (ALP and APP) were incubated for 5 min; 5 min chronoamperometry acquisition followed. Comparison of ALP activity (charge in µC) in APP/DEA and APP/EAE substrate/buffer systems as a function of MgCl$_2$ concentration indicates that MgCl$_2$ concentration significantly affects change in charge per any given enzyme concentration, as shown in FIG. 31.

Example 20

Figure 32:
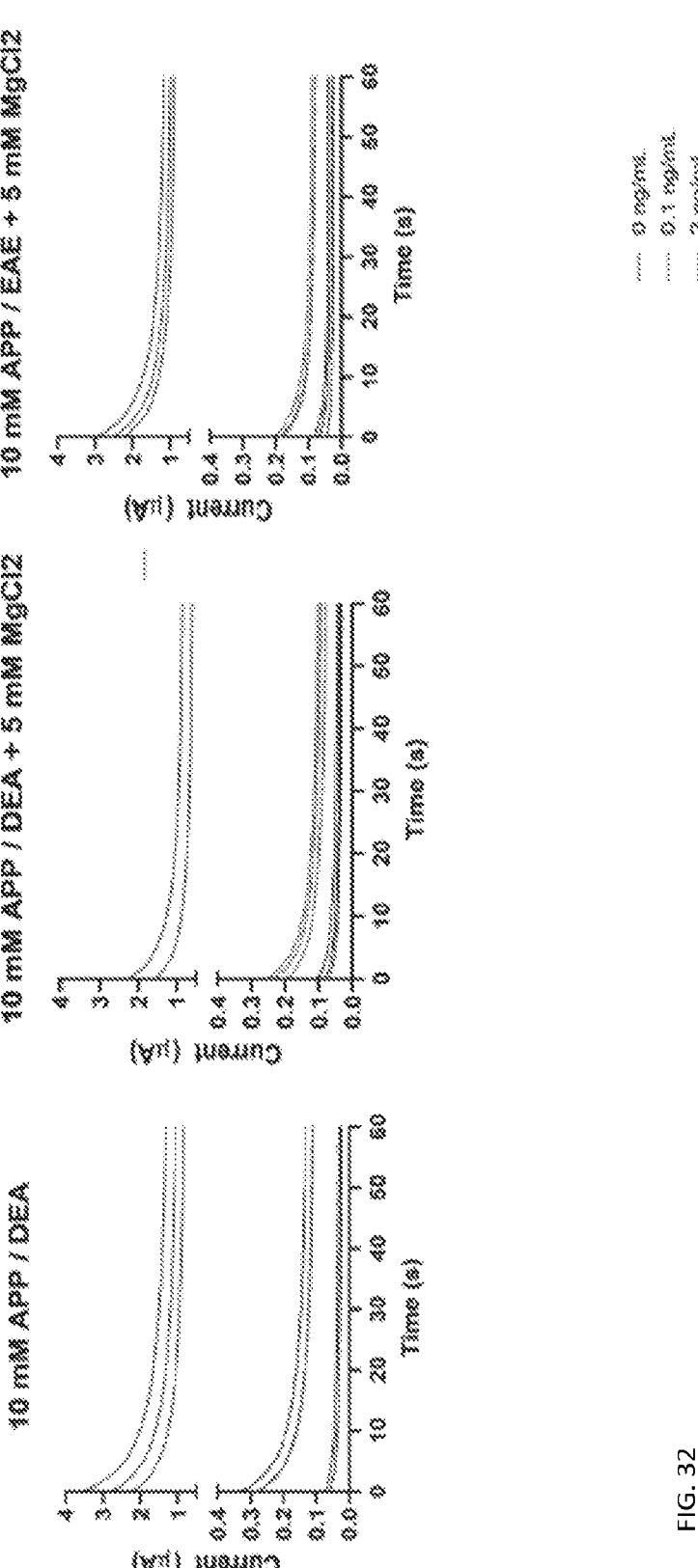
FIG. 32 shows current vs time for 10 mM APP in either DEA or EAE with or without 5 mM $MgCl_2$

Calf intestine sourced alkaline phosphatase was used in a sandwich assay measuring IL-6 concentration. A solution containing 1 µg/mL anti-IL-6 antibody bound to alkaline phosphatase, 1 µg/mL biotinylated anti-IL-6 antibody, and IL-6 protein at 2 ng/ml, 0.1 ng/mL or 0 ng/ml was prepared in assay buffer. A region of streptavidin-coated beads embedded in a lateral flow membrane sat atop an electrode. 100 ul of the test or control solution was added to a lateral flow membrane. Solution flowed across the membrane. After 2 minutes, the membrane was washed with 200 uL buffer, which was collected via a wicking pad. 60 uL 10 mM APP/DEA substrate (pH 9.8) with or without 5 mM MgCl$_2$ or 10 mM APP/EAE substrate (pH 9.8) with 5 mM MgCl$_2$ was then deposited on the membrane region atop the electrode to measure concentration of IL-6 captured in a sandwich configuration. Varying substrate solution/adding MgCl$_2$ did not significantly affect results in the IL-6 assay (FIG. 32).

Results indicate that enzymes either a) from different sources and/or b) modified for conjugation in commercially available kits may behave differently and their optimized concentration or optimized solution for running the chronoamperometric measurement may facilitate more sensitive detection of a target analyte.

Example 21

Figure 33:
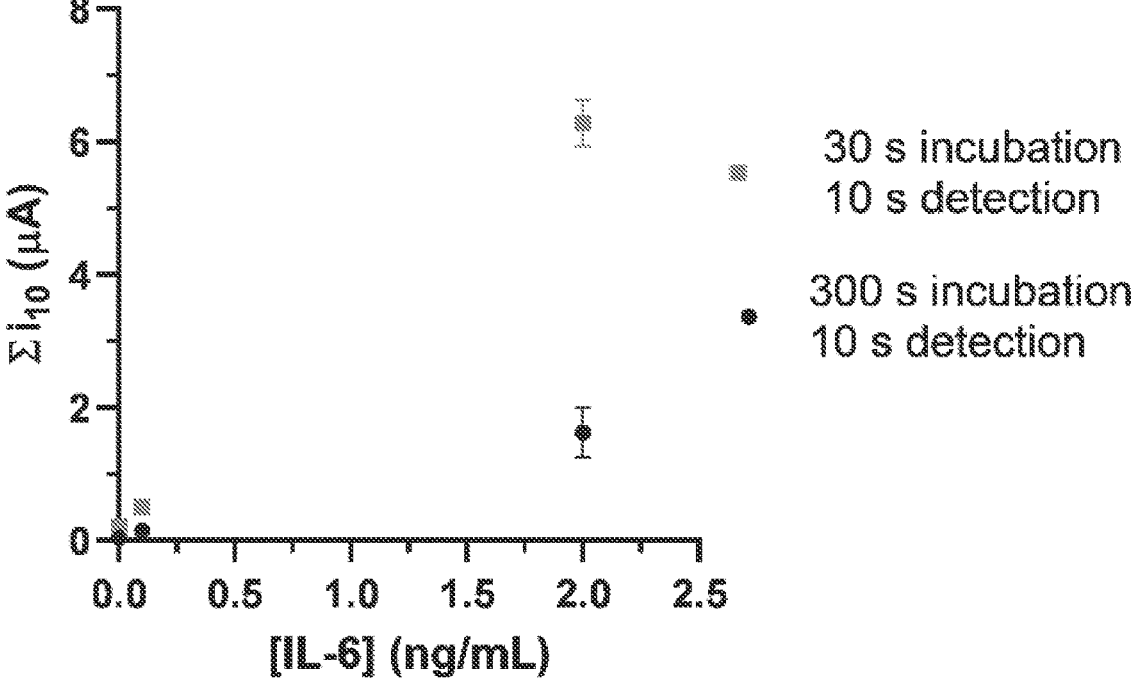
FIG. 33 shows data processing methods for repeated chronoamperometric detection with results utilizing the end current at 10 s.
Figure 34:
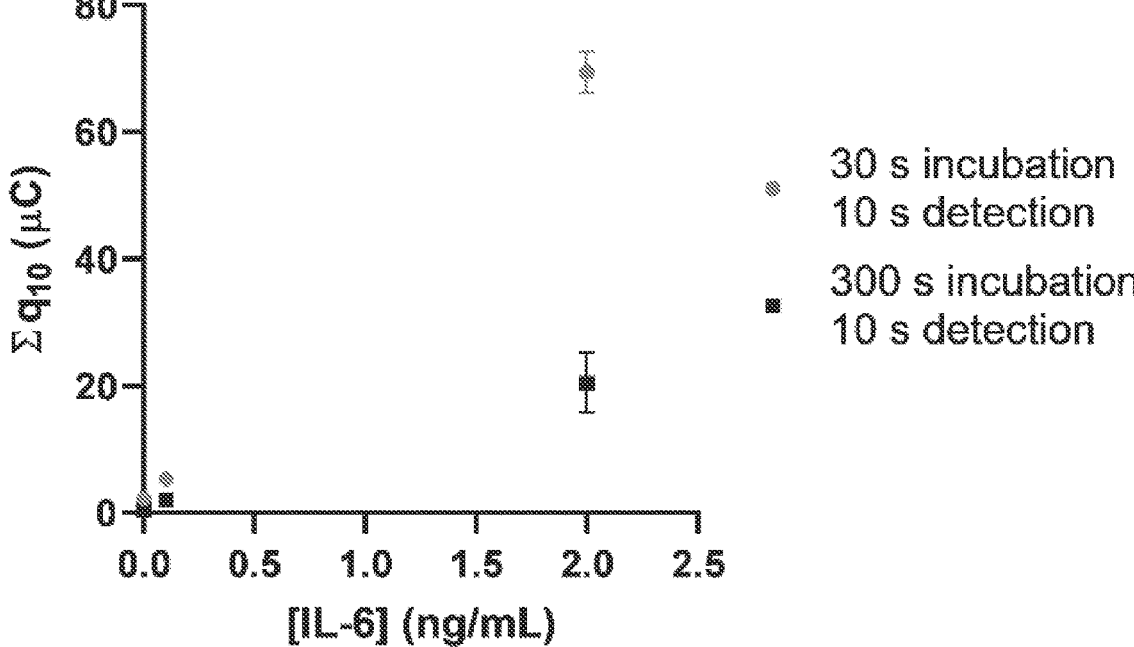
FIG. 34. Data processing methods for repeated chronoamperometric detection with results utilizing the charge at 10 s.
Figure 35:
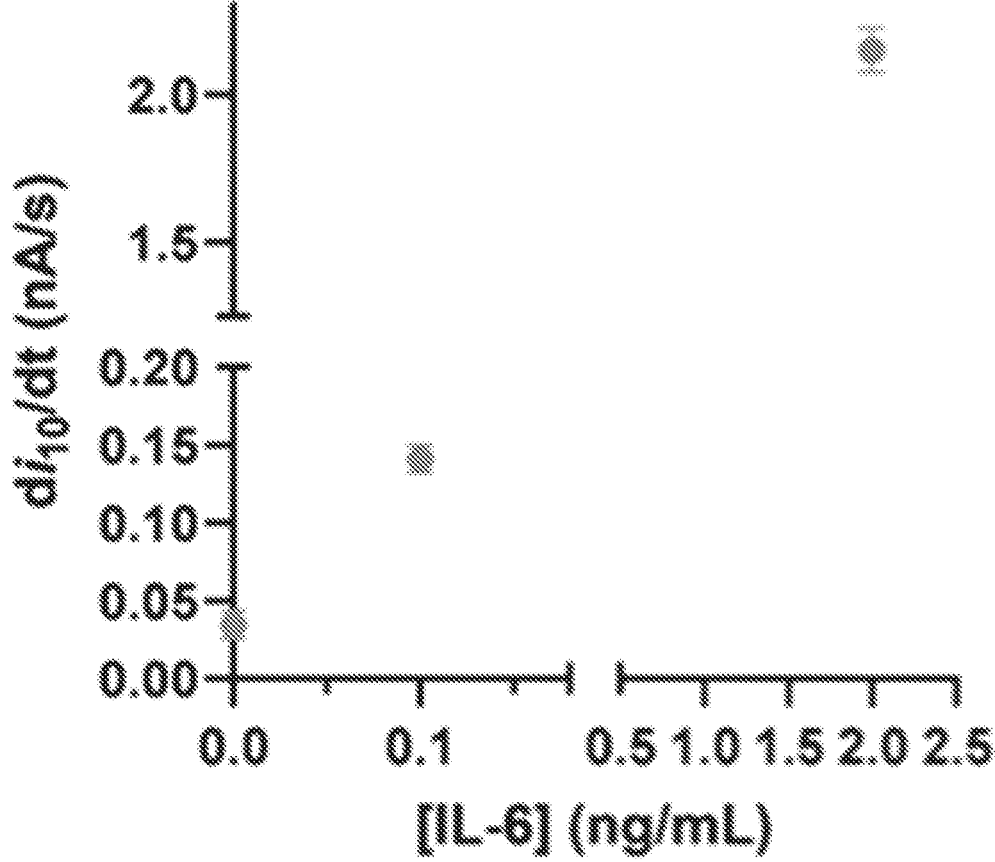
FIG. 35 shows data processing methods for repeated chronoamperometric detection with results utilizing the slope of end current at 10 s (integrated current over 10 seconds) versus total incubation time (300 s).

A solution containing 1 µg/mL anti-IL-6 antibody bound to alkaline phosphatase, 1 g/mL biotinylated anti-IL-6 antibody, and IL-6 protein at 2 ng/ml, 0.1 ng/mL or 0 ng/ml was prepared in assay buffer. A region of streptavidin-coated beads embedded in a lateral flow membrane sat atop an electrode. 100 ul of the test or control solution was added to a lateral flow membrane. Solution flowed across the membrane. After 2 minutes, the membrane was washed with 200 uL buffer, which was collected via a wicking pad. 60 uL of 10 mM 4-aminophenyl phosphate/diethanolamine substrate (pH 9.8) was then deposited on the membrane region atop the electrode to measure concentration of IL-6 captured in a sandwich configuration (FIG. 28). In one case, chrono-amperometry was run for 10 sec following 5 min substrate incubation. In another case, modified chronoamperometry was run by repeated application of a 0.2 V (vs Ag) potential (measuring current over these 10 seconds) every 30 s after introduction of the substrate solution for a total duration of 310 sec (FIG. 27). After acquiring current versus time data for the modified, repeated chronoamperometric detection, the results were analyzed by three methods. First by summation of the end current following each 10 sec detection period over the full 310-second detection (FIG. 33). Second, by integrating the chronoamperometry curves to obtain charge after each 10-sec detection period and taking the summation of each charge measurement over the full 310 s detection (FIG. 34). And third, by comparing the slope of the end current at 10 seconds versus the total time since substrate addition (310 seconds). These three data analysis methods are depicted in FIG. 33 (FIG. 35).

Figure 40:
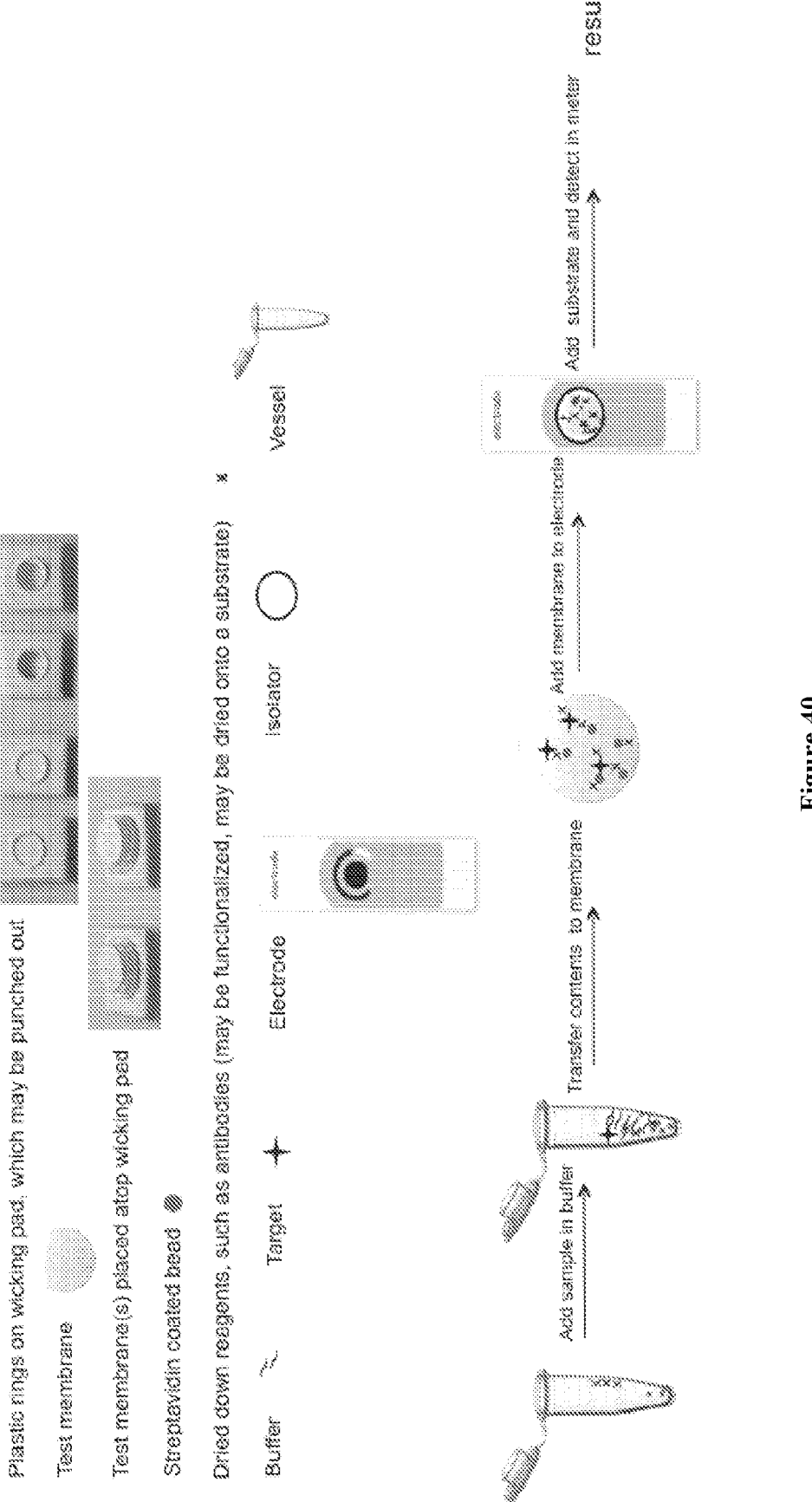
FIG. 40 shows a method of detecting a target molecule via 1) addition of a sample to a vessel with reagents capable of binding to the target molecule of interest in buffer, 2) transfer of vessel contents to a membrane (wash not shown), and 3) coupling of membrane and electrode. Addition of substrate to the membrane for subsequent electrochemical detection affords result. This protocol facilitates electrochemical detection of the target molecule.
Figure 41:
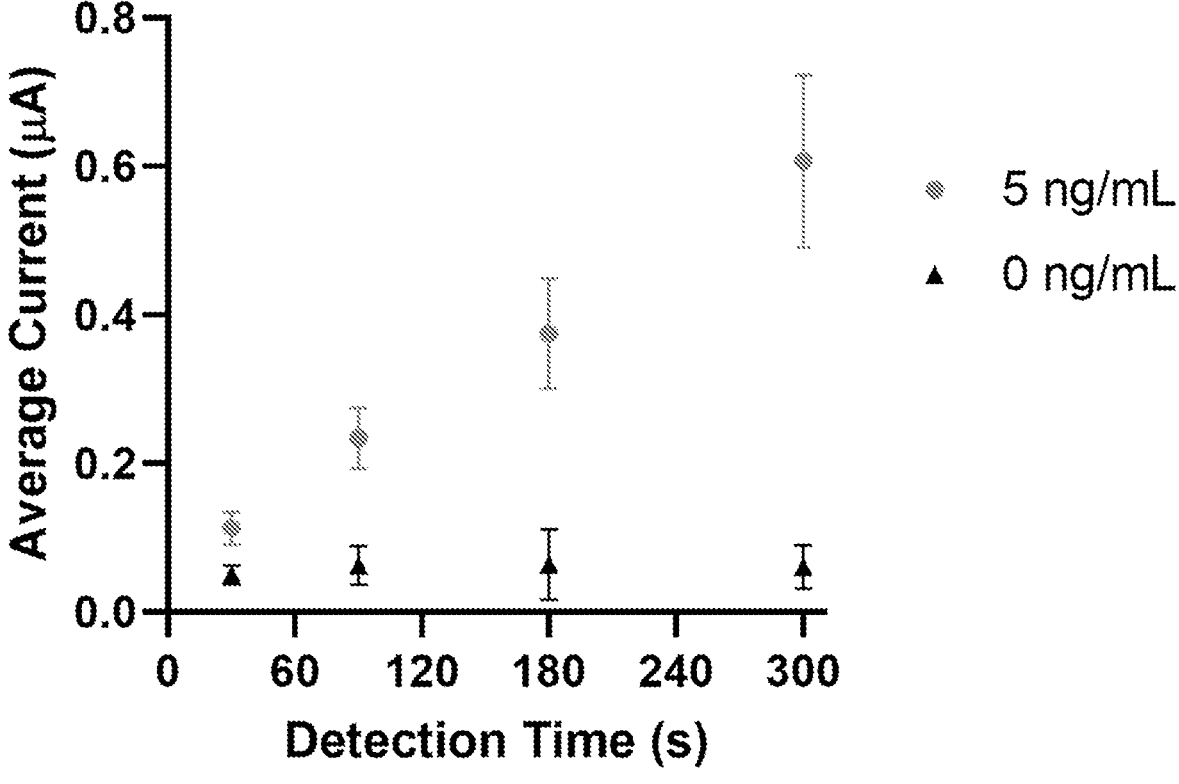
FIG. 41 shows 2 sec chronoamperometric detection at expanding time intervals of nucleocapsid protein captured on a membrane sitting atop an electrode. Error bars depict standard deviation of three samples. The data points and error bars represent the current mean and standard deviations.

Example 22: Method for Running a Rapid Immunoassay Through a Membrane with Subsequent Electrochemical Detection of Immunoassay Target A solution containing 1 μg/mL of anti-nucleocapsid protein antibody 1 bound to alkaline phosphatase, 1 μg/mL biotinylated anti-nucleocapsid protein antibody 2 (matched to a different target epitope than antibody 1), and nucleocapsid protein at 5 ng/mL or 0 ng/mL was prepared in assay buffer in a tube. As shown in FIG. 40, this was formulated to mimic addition of a biological sample, which may be diluted in buffer, to a vessel containing reagents and a capture and/or anchoring material. The mixed solution containing 500 or 0 μg nucleocapsid protein was transferred onto a blank test membrane (blocked or unblocked but not functionalized with any capture reagents) from above and subsequently washed with buffer, which was collected via a wicking material. In this example the membrane sat atop a plastic ring to raise it above the wicking pad, but the membrane may sit directly on the wicking pad, the membrane may sit atop another membrane material, or the membrane may be suspended above a collection device, etc. 60 uL of 10 mM 4-aminophenyl phosphate/diethanolamine substrate (pH 9.8) was then deposited on the membrane region atop the electrode to measure concentration of target present and captured. Chronoamperometry was run for 2 sec, 30 sec after substrate addition, then again at 90 sec, 180 sec and 300 sec by repeated application of a 0.2 V (vs Ag) potential. Results show detection of nucleocapsid protein via this method (FIG. 41).

Figure 42:
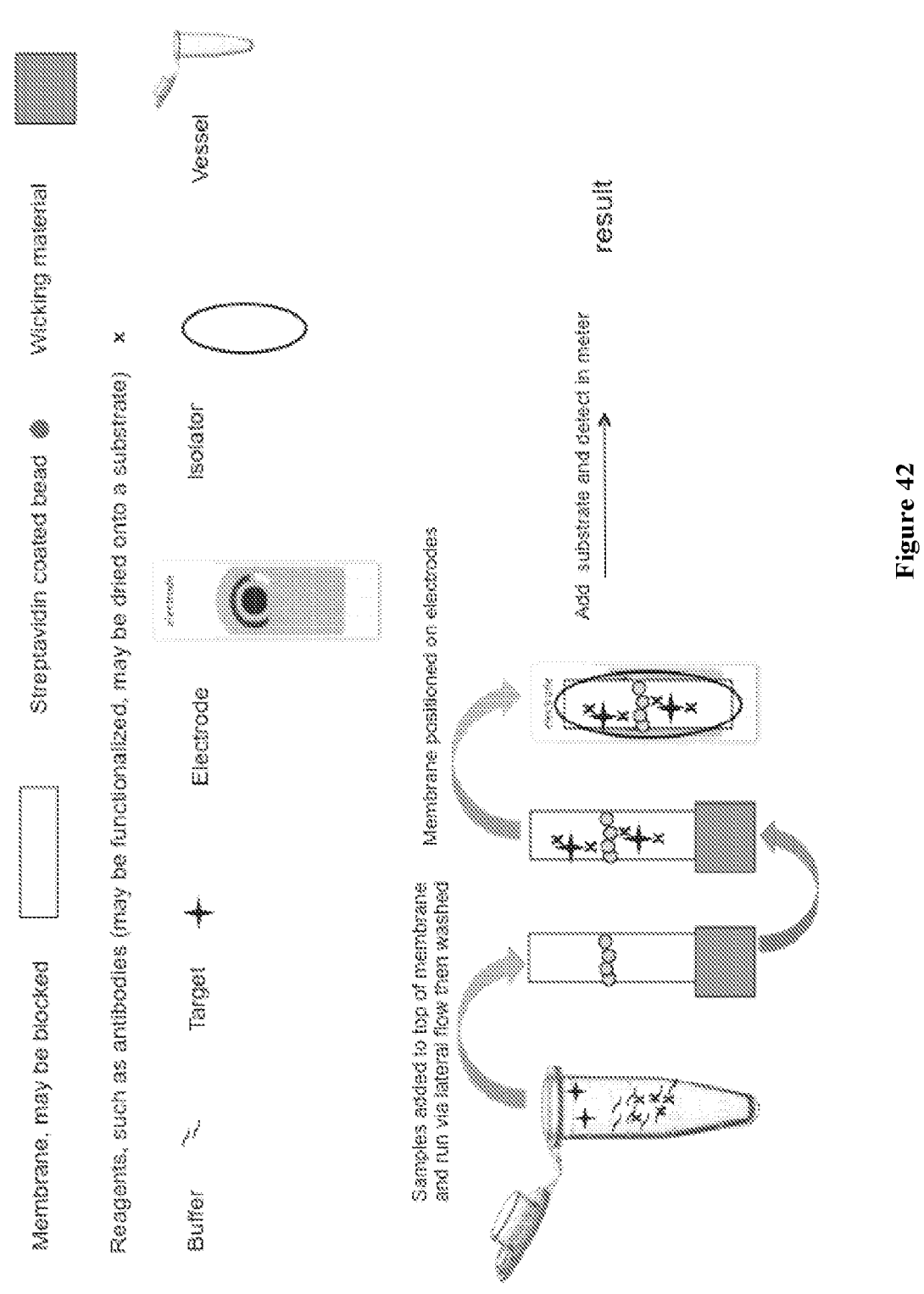
FIG. 42 shows a method of detecting a target molecule via first running a lateral flow immunoassay and subsequently, electrochemically detecting a target bound to a specified region on a membrane atop an electrode covered with substrate solution. The membrane may start positioned on the electrode in another embodiment. This method facilitates electrochemical detection of the target molecule.
Figure 43:
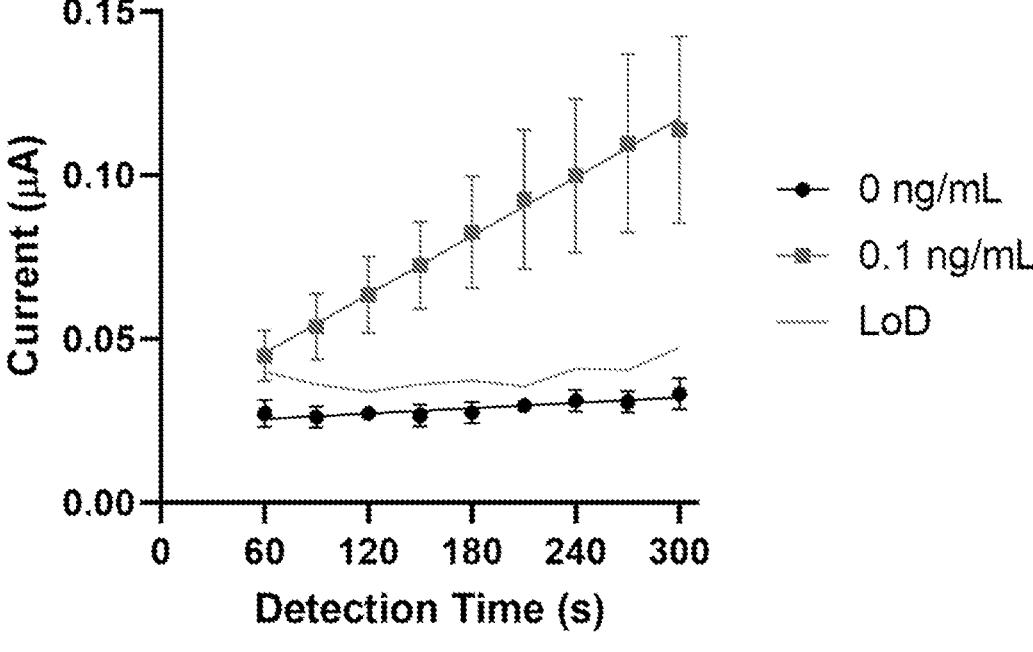
FIG. 43 shows results from a modified chronoamperometric detection scheme relying on a 30 sec interval and 2 sec acquisition time. Error bars depict standard deviation of three samples. The line labeled "LoD" represents the current values three standard deviations above the 0 ng/mL baseline.

Example 23: Method for Running an Immunoassay Along a Membrane with Subsequent Electrochemical Detection of Immunoassay Target A solution containing 1 μg/mL anti-IL-6 antibody 1 bound to alkaline phosphatase, 1 g/mL biotinylated anti-IL-6 antibody 2 (matched to a different target epitope than antibody 1), and TL-6 protein at 0.1 ng/mL or 0 ng/ml was prepared in assay buffer. 100 uL of the test or control solution was added to a lateral flow membrane that contained embedded streptavidin-coated beads. Solution (containing 10 or 0 μg TL-6 protein) flowed across the membrane and the membrane then was washed with buffer. Excess solution was collected via a wicking pad. 60 uL 10 mM 4-AP/DEA substrate was then deposited on the membrane region atop an electrode to measure concentration of TL-6 captured in a sandwich configuration (FIG. 42). Detection scheme comprised repeated chronoamperometry runs every 30 sec (each data point shows 2-second current) for 300 sec (FIG. 43). Fast detection was accomplished clearly within 2-3 minutes.

Figure 44:
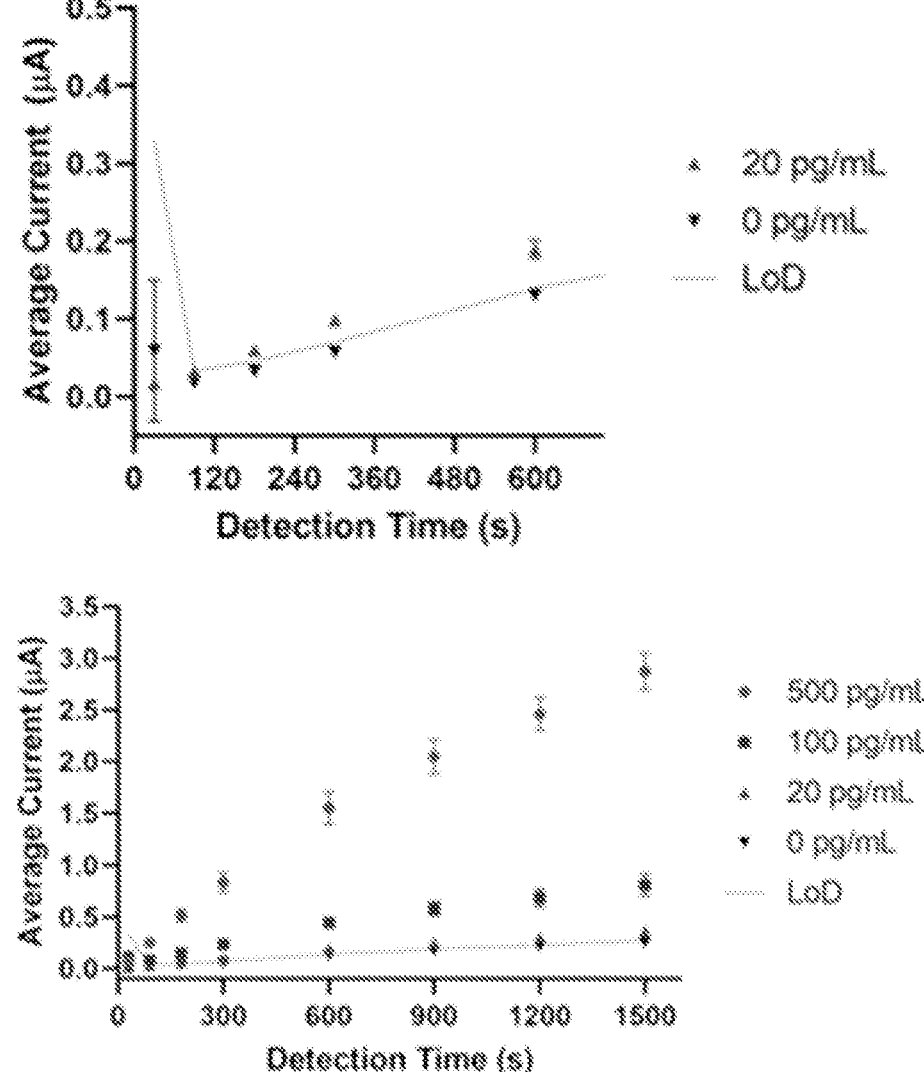
FIG. 44 shows results from modified chronoamperometry used to detect IL-6 down to 20 pg/ml. Top plot expands lowest concentration of 20 pg/ml vs 0 for clarity; bottom plot includes range of concentrations from 500 pg/ml down to 0. Error bars depict standard deviation of three samples. The line labeled "LoD" represents the current values three standard deviations above the 0 ng/mL baseline.

Example 24: Modified Chronoamperometry Used in Conjunction with an Immunoassay to Detect IL-6 Protein Down to 20 μg/ml A solution containing 1 μg/mL anti-IL-6 antibody 1 bound to alkaline phosphatase, 1 g/mL biotinylated anti-IL-6 antibody 2 (matched to a different target epitope than antibody 1), and TL-6 protein at 500, 100, 20 or 0 μg/mL was prepared in assay buffer. 100 uL of the test or control solution was added to a lateral flow membrane that contained embedded streptavidin-coated beads. Solution (containing 50, 10.2 or 0 μg IL-6 protein) flowed across the membrane and the membrane then was washed with buffer. Excess solution was collected via a wicking pad. The membrane was transferred to the surface of an electrode and 60 uL 10 mM 4-AP/DEA substrate was then deposited on the membrane to measure concentration of IL-6 captured in a sandwich configuration (FIG. 28). Electrochemical detection comprised 2 sec chronoamperometry runs at 30 sec, 90 sec, 180 sec, 300 sec, then every 300 sec up to 1500 sec. Each data point shows 2-second current mean and standard deviation in FIG. 44. Slope of end currents as a function of concentration is show in FIG. 45.

Figure 46:
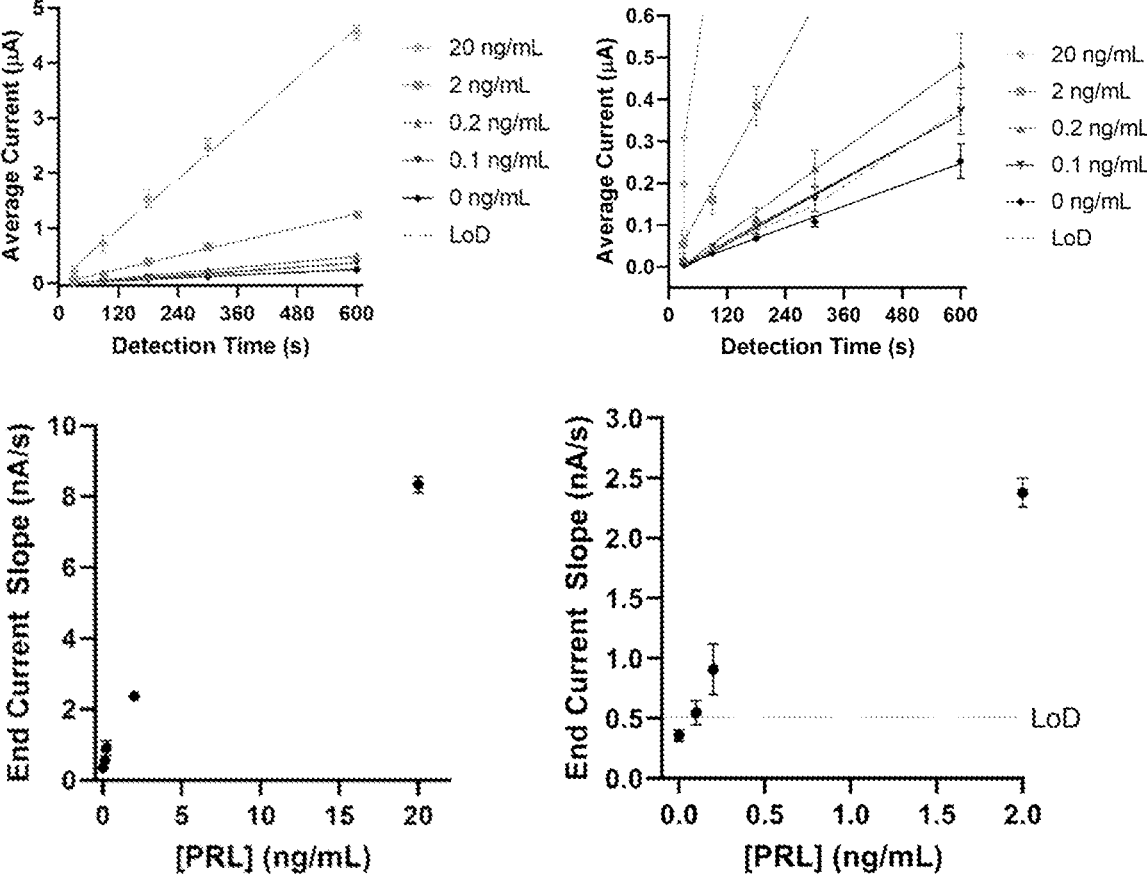
FIG. 46 shows results from modified chronoamperometry used to prolactin protein. Error bars depict standard deviation of three samples. The top left plot shows the current response for prolactin concentrations from 20 to 0 ng/mL. The top right plot depicts the same data as the left, zoomed in to show the 0.2, 0.1, and 0 ng/mL data more closely. The bottom left and right plots show the results when taking the slope of the end currents over the detection time in nA/s for the range of prolactin concentrations measured (20 to 0 ng/mL). The bottom right plot is a zoomed-in version showing the lowest four levels. Error bars depict standard deviation of three samples. The line labeled "LoD" represents the current values three standard deviations above the 0 ng/mL baseline.
Figure 47:
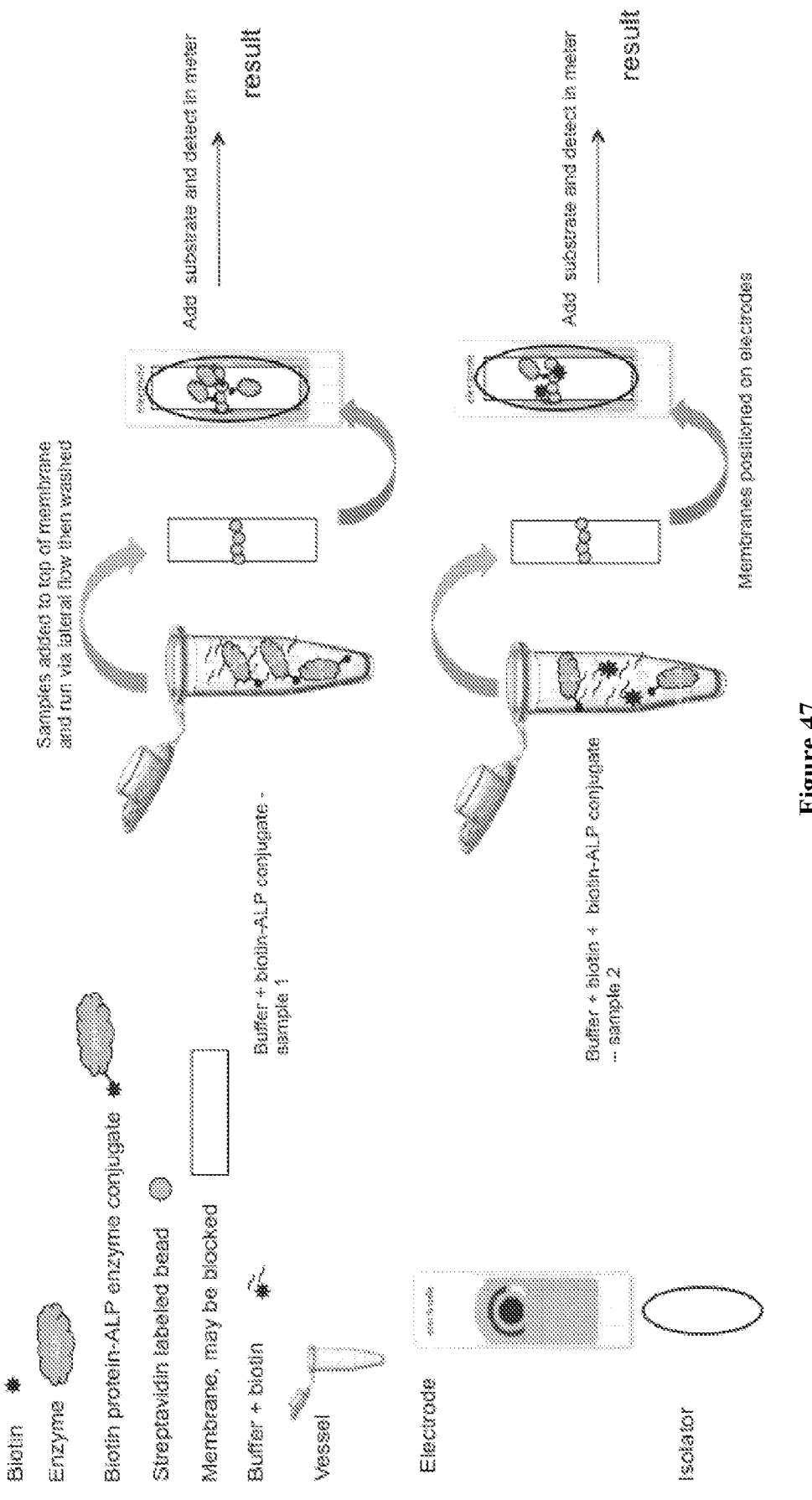
FIG. 47 shows a method of detecting a target molecule via first running a competitive immunoassay via lateral flow and subsequently electrochemically detecting a target bound to a specified region on a membrane. This method facilitates electrochemical detection of the target molecule by measuring a decrease in current according to how much target is present.

Example 25: Modified Chronoamperometry Used in Conjunction with an Immunoassay to Detect Prolactin Protein Down to 200 μg/ml A solution containing 1 μg/mL anti-prolactin antibody 1 bound to alkaline phosphatase, 1 g/mL biotinylated anti-prolactin antibody 2 (matched to a different target epitope than antibody 1), and prolactin protein at 20, 2, 0.2, 0.1 or 0 ng/mL was prepared in assay buffer. 100 uL of the test or control solution was added to a lateral flow membrane that contained embedded streptavidin-coated beads. Solution (containing 2 or 0 ng prolactin protein) flowed across the membrane and the membrane then was washed with buffer. Excess solution was collected via a wicking pad. The lateral flow membrane was transferred to the surface of an electrode and 60 uL 10 mM 4-AP/DEA substrate was then deposited on the membrane to measure concentration of IL-6 captured in a sandwich configuration (FIG. 28). Detection scheme comprised 2 sec chronoamperometry runs at 30 sec, 90 sec, 180 sec, 300 sec, 600 sec. Each data point below shows 2-second current mean and standard deviation; slope of end currents as a function of concentration also is show (FIG. 46).

Example 26

Figure 48:
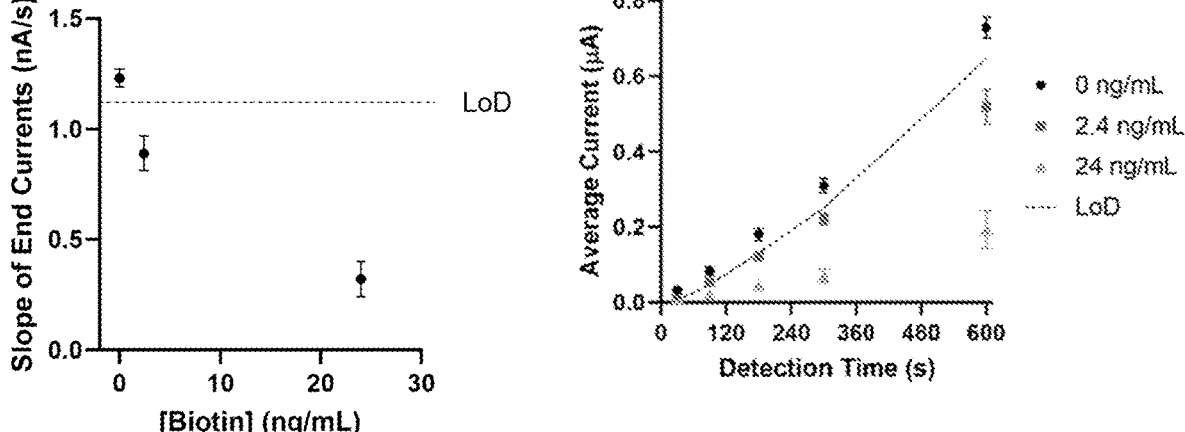
FIG. 48 shows results from modified chronoamperometry used to detect biotin via a competitive assay in conjunction with biotin conjugated alkaline phosphatase. Error bars depict standard deviation of three samples. The line labeled "LoD" represents the current values three standard deviations above the 0 ng/mL baseline.
Figure 49:
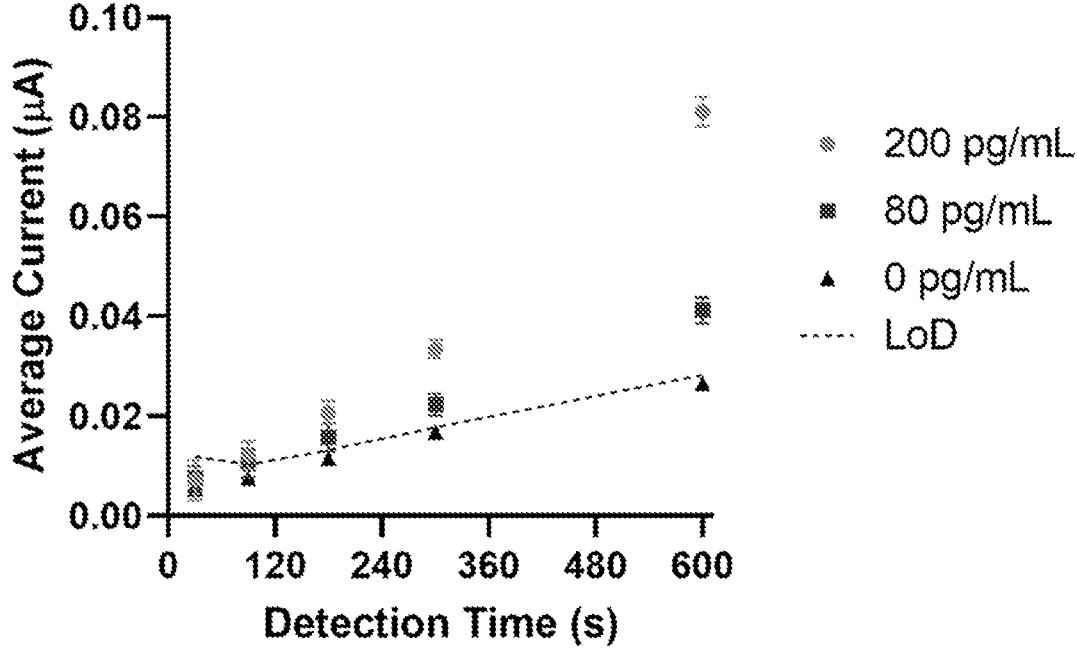
FIG. 49 shows results from modified chronoamperometry used to detect biotin conjugated alkaline phosphatase down to 80 pg/ml. Error bars depict standard deviation of three samples. The line labeled "LoD" represents the current values three standard deviations above the 0 ng/mL baseline.

Modified chronoamperometry used in conjunction with a competitive immunoassay to detect biotin down to 2.4 ng/mL and demonstrate a competitive assay. Solution containing 1 nM biotin conjugated alkaline phosphatase in assay buffer (control), and solutions containing 1 nM biotin conjugated alkaline phosphatase plus 10 nM or 100 nM biotin in assay buffer (test), were prepared. 100 ul of the test or control solution was added to a lateral flow membrane that contained embedded streptavidin-coated beads. Solution (containing 2.4 ng or 240 μg biotin) flowed across the membrane and the membrane then was washed with buffer. Excess solution was collected via a wicking pad. The lateral flow membrane was transferred to the surface of an electrode and 60 uL 10 mM 4-AP/DEA substrate was then deposited on the membrane to measure concentration of protein based on decreasing current (competitive detection scheme depicted in FIG. 43). Electrochemical detection comprised 2 sec chronoamperometry runs at 30 sec, 90 sec, 180 sec, 300 sec, and 600 sec. Each data point shows 2-second current mean and standard deviation in FIG. 48.

Figure 50:
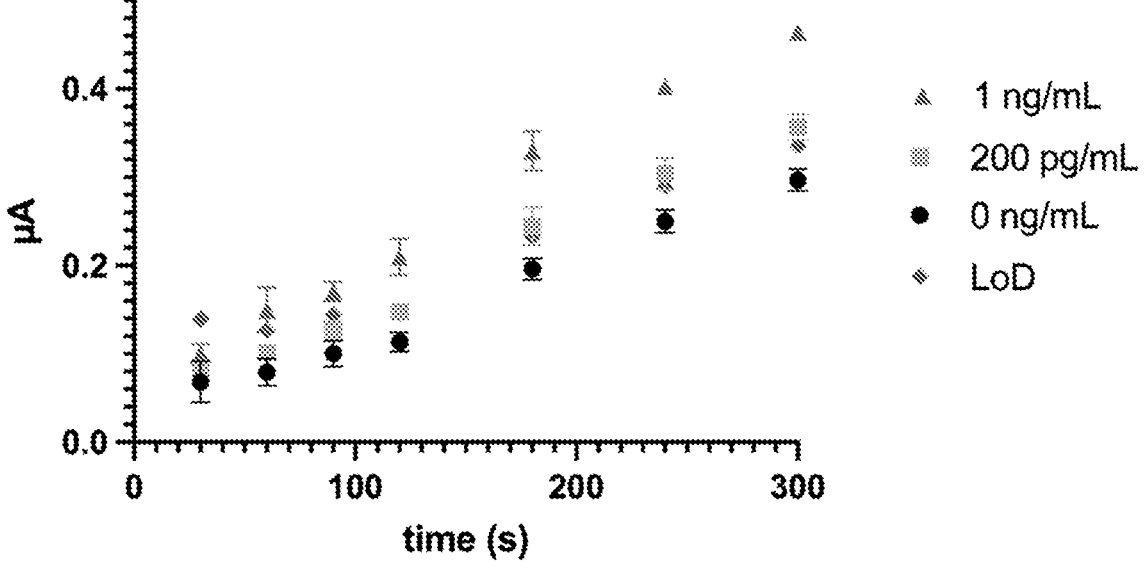
FIG. 50 shows results from modified chronoamperometry used to detect osteopontin down to 200 pg/ml using an electrode possessing a carbon working electrode, carbon counter electrode and Ag/AgCl reference electrode. Error bars depict standard deviation of three samples. The points labeled "LoD" represents the current values three standard deviations above the 0 ng/mL baseline.
Figure 51:
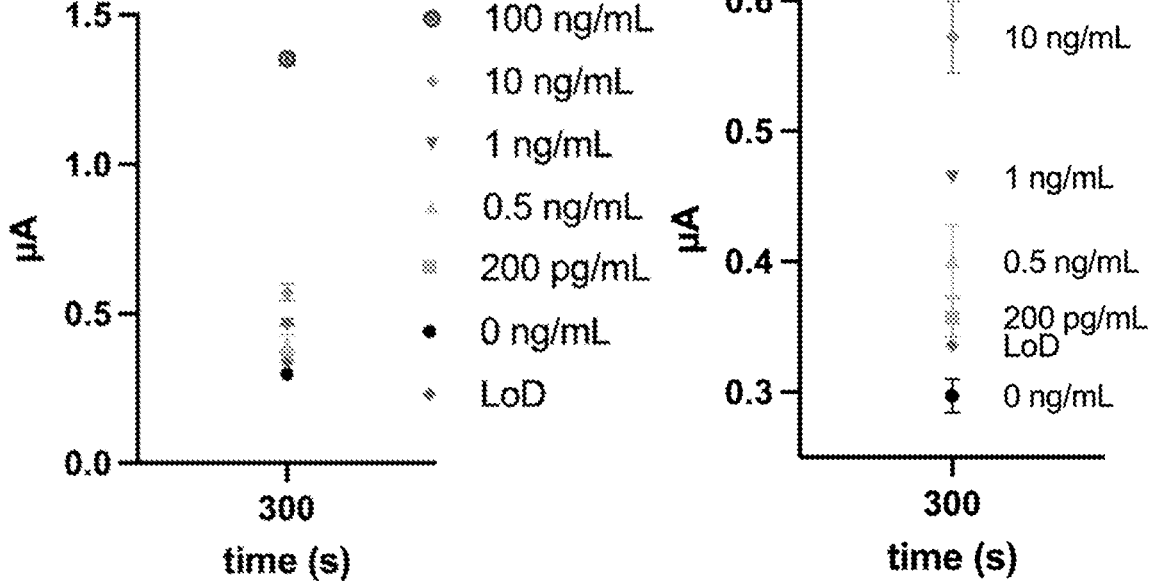
FIG. 51 shows results from modified chronoamperometry used to detect osteopontin at 100 ng/mL, 10 ng/mL, 1 ng/mL, 0.5 ng/mL, and 200 pg/mL using an electrode possessing a carbon working electrode, carbon counter electrode and Ag/AgCl reference electrode. Measurements illustrated at 300 seconds of detection time. Error bars depict standard deviation of three samples. The points labeled "LoD" represents the current values three standard deviations above the 0 ng/mL baseline.
Figure 52:
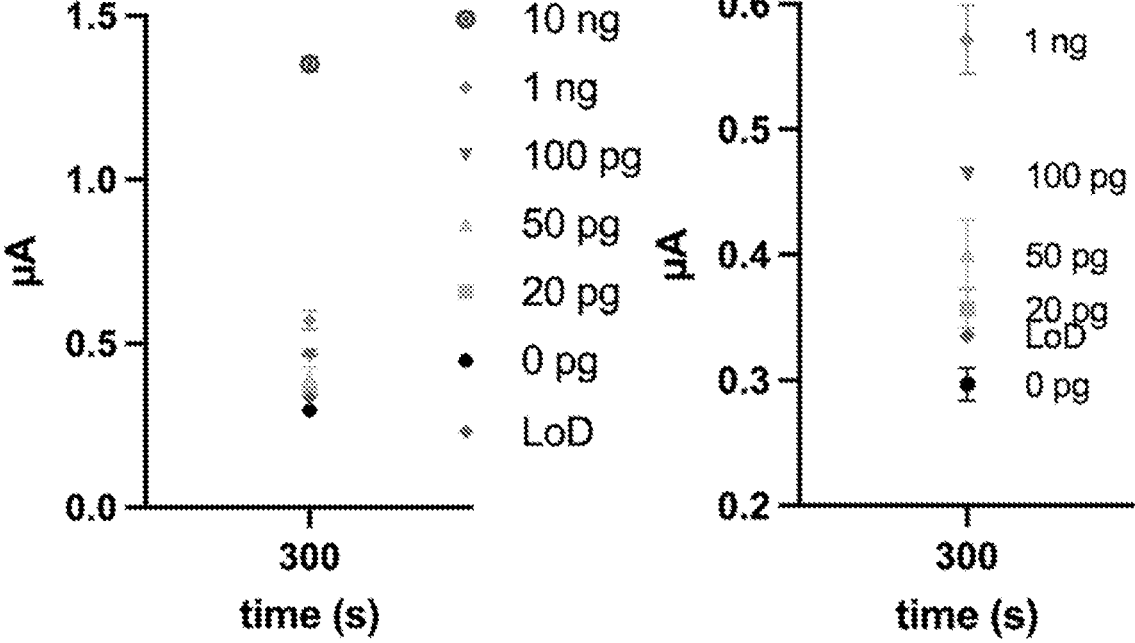
FIG. 52 shows results from modified chronoamperometry used to detect the theoretical maximum amount of osteopontin applied to the membrane at 10 ng, 1 ng, 100 pg, 50 pg, and 20 pg using an electrode possessing a carbon working electrode, carbon counter electrode and Ag/AgCl reference electrode. Measurements illustrated at 300 seconds of detection time. Error bars depict standard deviation of three samples. The points labeled "LoD" represents the current values three standard deviations above the 0 ng baseline.
Figure 53:
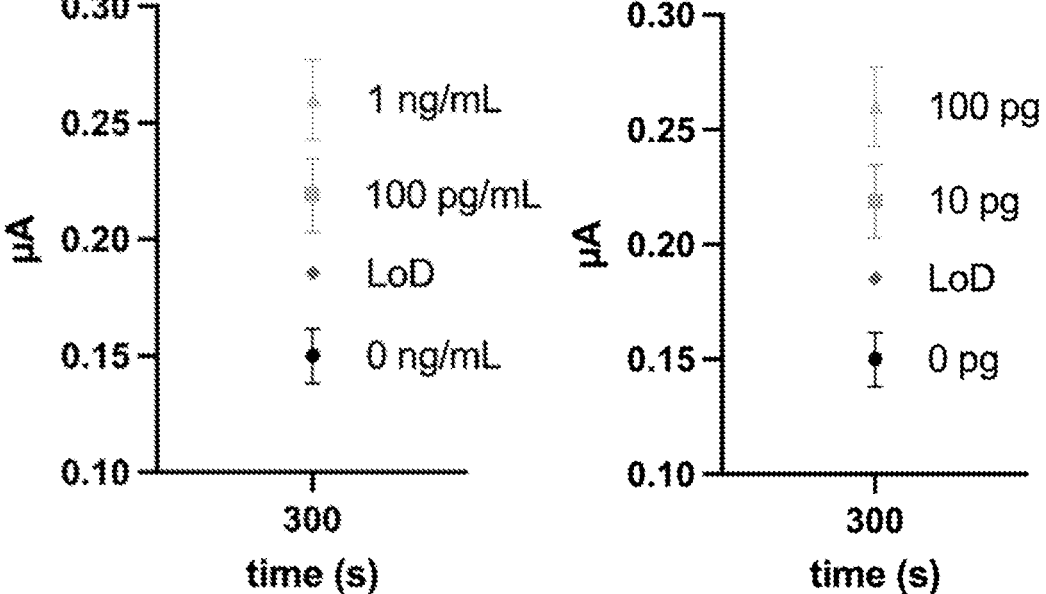
FIG. 53 shows results from modified chronoamperometry used to detect_osteopontin at 1 ng/mL, 100 pg/mL, and using an electrode possessing a platinum working electrode, platinum counter electrode and Ag/AgCl reference electrode, and the theoretical maximum amount of osteopontin applied to the membrane at 100 pg, and 10 pg. Measurements illustrated at 300 seconds of detection time. Error bars depict standard deviation of three samples. The points labeled "LoD" represents the current values three standard deviations above the 0 ng/mL baseline.
Figure 54:
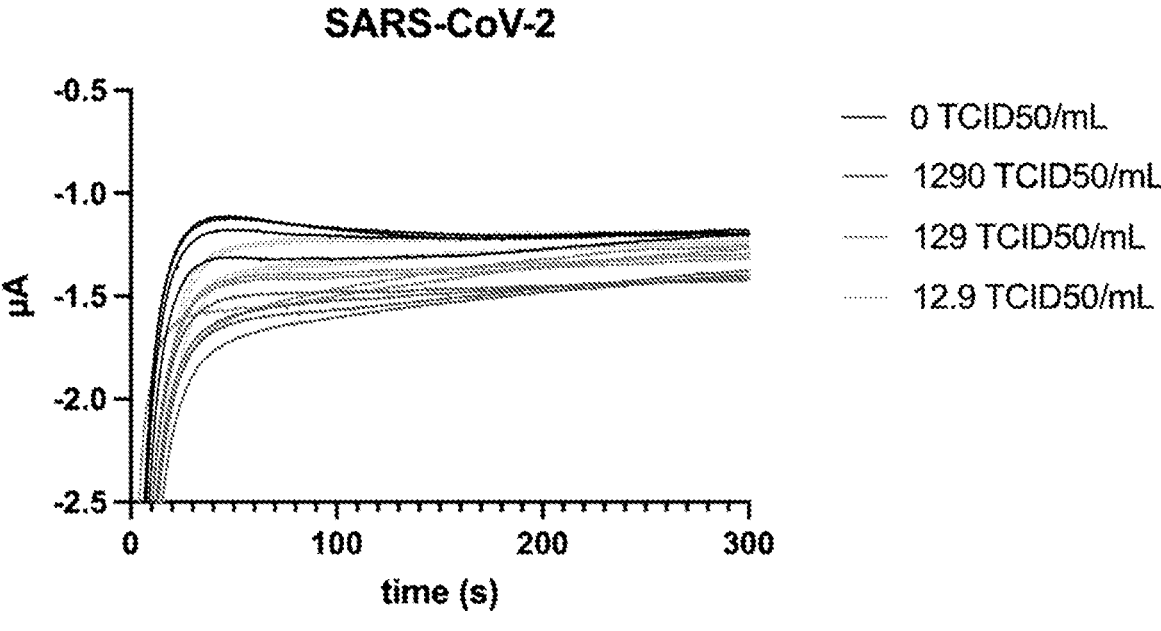
FIG. 54 shows results from chronoamperometry used to detect SARS-CoV-2 down to 12.9 TCID50/mL using an electrode possessing a carbon/Prussian blue working electrode, carbon counter electrode and Ag/AgCl reference electrode.
Figure 55:
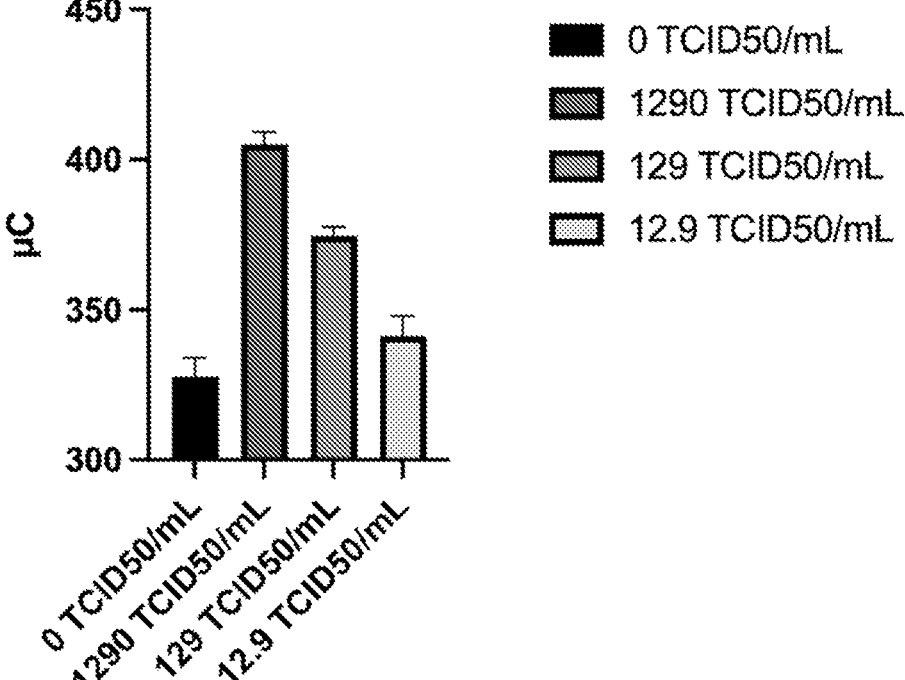
FIG. 55 shows total charge from chronoamperometry used to detect SARS-CoV-2 down to 12.9 TCID50/ml using an electrode possessing a carbon/Prussian blue working electrode, carbon counter electrode and Ag/AgCl reference electrode. Total charge (pcoulomb) taken from 30 to 300 seconds.
Figure 56:
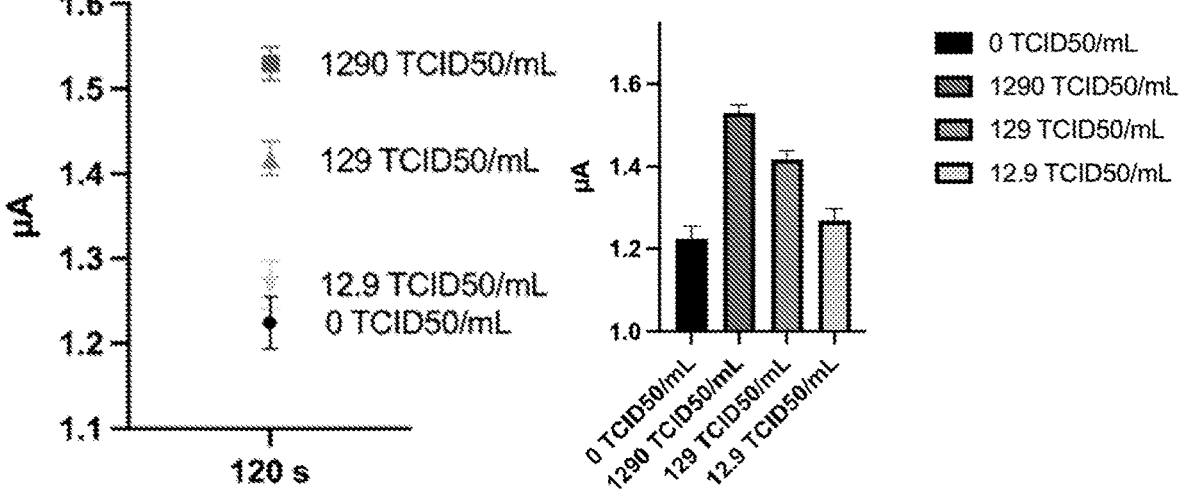
FIG. 56 shows the absolute value of the current ($|\mu A|$) at 120 seconds from chronoamperometry used to detect SARS-CoV-2 down to 12.9 TCID50/ml using an electrode possessing a carbon/Prussian blue working electrode, carbon counter electrode and Ag/AgCl reference electrode.
Figure 57:
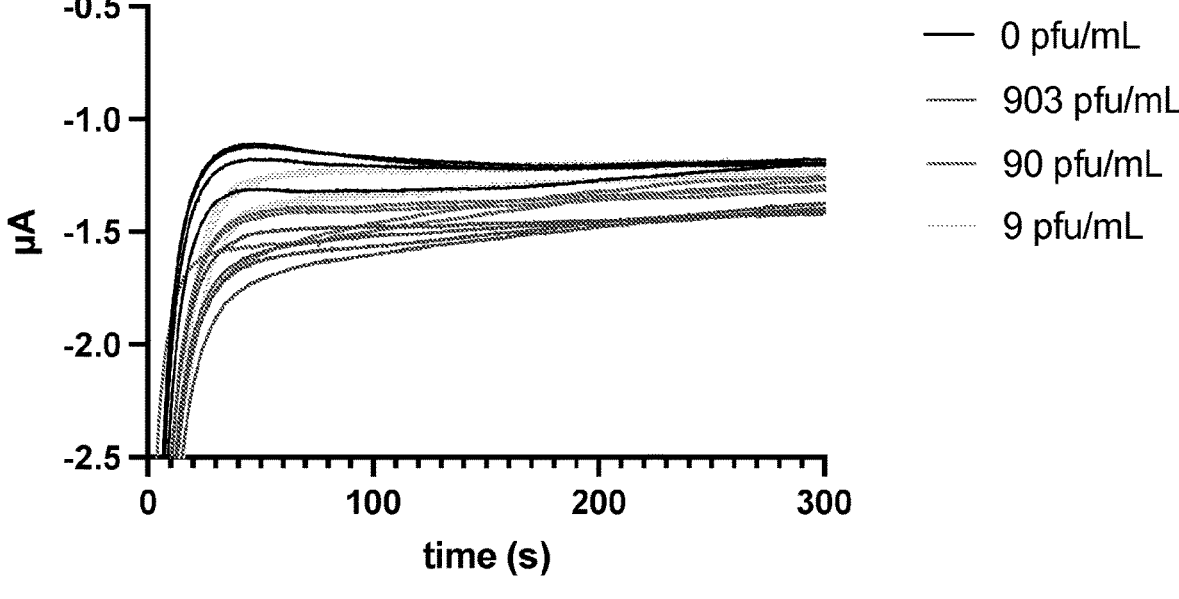
FIG. 57 shows results from chronoamperometry used to detect SARS-CoV-2 down to 9 pfu/ml using an electrode possessing a carbon/Prussian blue working electrode, carbon counter electrode and Ag/AgCl reference electrode. Data from FIG. 54 was converted to pfu/mL.
Figure 58:
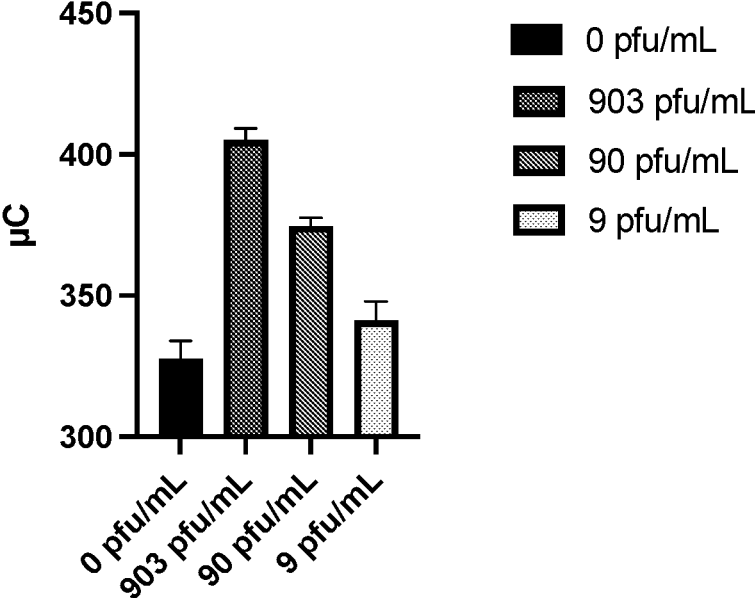
FIG. 58 shows total charge from chronoamperometry used to detect SARS-CoV-2 down to 9 pfu/ml using an electrode possessing a carbon/Prussian blue working electrode, carbon counter electrode and Ag/AgCl reference electrode. Total charge (pcoulomb) taken from 30 to 300 seconds. Data from FIG. 55 was converted to pfu/mL.
Figure 59:
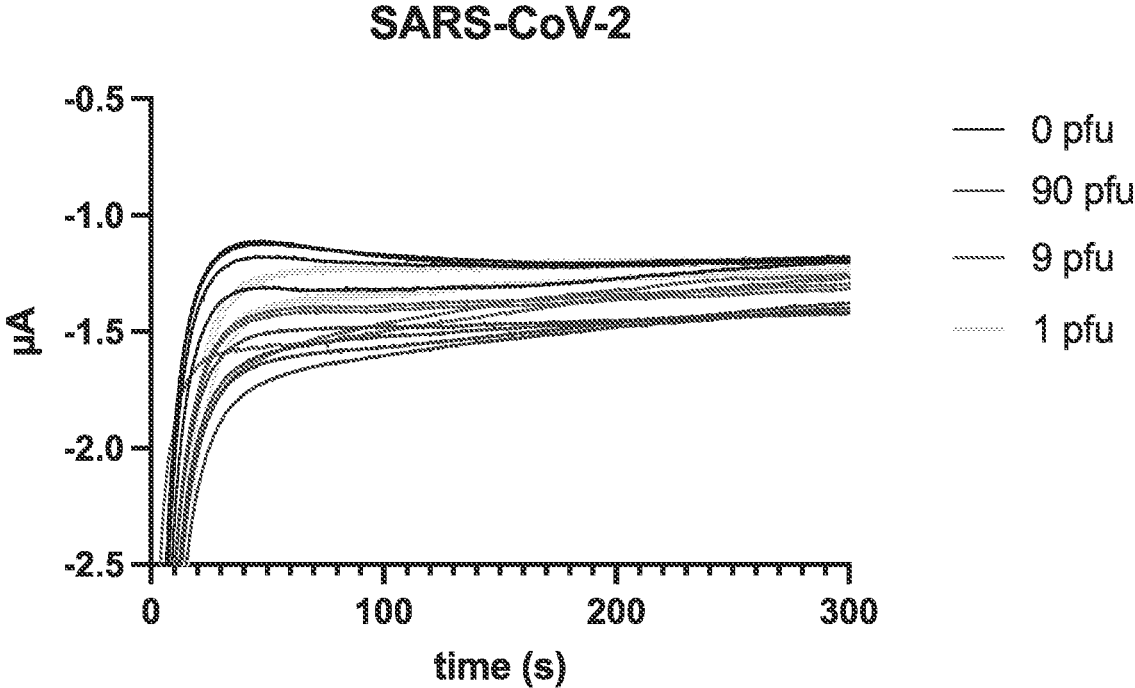
FIG. 59 shows results from chronoamperometry used to detect SARS-CoV-2 down to 1 plaque forming unit (pfu) using an electrode possessing a carbon/Prussian blue working electrode, carbon counter electrode and Ag/AgCl reference electrode. The theoretical maximum number of plaque forming units applied to the membrane. Data from FIG. 57 was converted to pfu.
Figure 60:
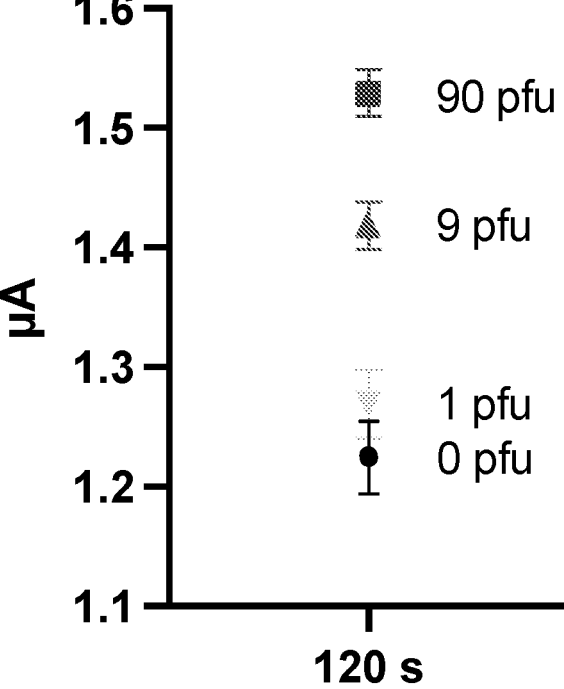
FIG. 60 shows the absolute value of the current ($|\mu A|$) at 120 seconds from chronoamperometry used to detect SARS- CoV-2 down to 1 plaque forming unit (pfu) using an electrode possessing a carbon/Prussian blue working electrode, carbon counter electrode and Ag/AgCl reference electrode. The theoretical maximum number of plaque forming units applied to the membrane. Data from FIG. 56 was converted to pfu.
Figure 61:
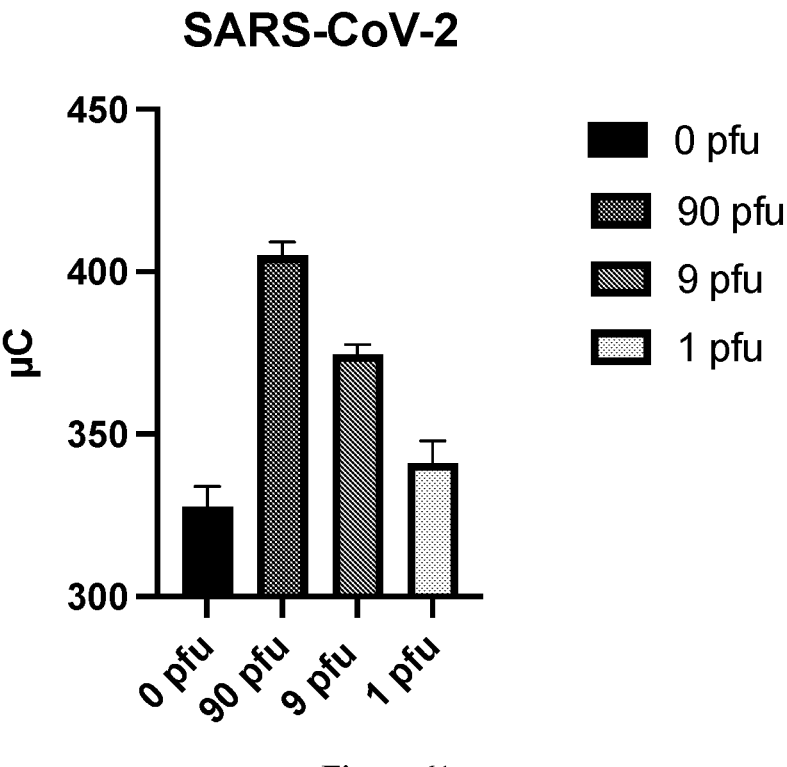
FIG. 61 shows total charge from chronoamperometry used to detect SARS-CoV-2 down to 1 plaque forming unit (pfu) using an electrode possessing a carbon/Prussian blue working electrode, carbon counter electrode and Ag/AgCl reference electrode. The theoretical maximum number of plaque forming units applied to the membrane. Total charge (pcoulomb) taken from 30 to 300 seconds. Data from FIG. 58 was converted to pfu.

Example 27: Modified Chronoamperometry Used in Conjunction with an Immunoassay to Detect a Protein Conjugate Down to 80 μg/ml A solution containing biotin conjugated alkaline phosphatase in assay buffer was prepared at 200 μg/mL, 80 μg/mL or 0 ng/mL. 100 uL of the test or control solution was added to a lateral flow membrane that contained embedded streptavidin-coated beads. Solution (containing 20, 8 or 0 μg protein conjugate) flowed across the membrane and the membrane then was washed with buffer. Excess solution was collected via a wicking pad. The lateral flow membrane was transferred to the surface of an electrode and 60 uL 10 mM 4-AP/DEA substrate including 5 mM MgCl$_2$ was then deposited on the membrane to measure concentration of conjugated protein. Detection scheme comprised 2 sec chronoamperometry runs at 30 sec, 90 sec, 180 sec, 300 sec, 600 sec. Each data point shows 2-second current mean and standard deviation in FIG. 50.

Example 28: Modified Chronoamperometry Used in Conjunction with an Immunoassay to Detect Osteopontin Protein Down to 100 μg/ml A solution containing 1 μg/mL anti-osteopontin antibody 1 conjugated to alkaline phosphatase, 1 μg/mL biotinylated anti-osteopontin antibody 2 (matched to a different target epitope than antibody 1), and osteopontin protein at 100, 10, 0.5, 0.2, 0.1 or 0 ng/mL was prepared in assay buffer. 100 uL of the test or control solution was added to a lateral flow membrane that contained embedded streptavidin-coated beads. Solution (containing 100, 20 or 0 μg osteopontin protein) flowed across the membrane and the membrane then was washed with buffer. Excess solution was collected via a wicking pad. The lateral flow membrane was transferred to the surface of an electrode and 50 uL 10 mM 4-AP/DEA substrate was then deposited on the membrane to measure concentration of osteopontin captured in a sandwich configuration. Detection scheme comprised 2 sec chronoamperometry runs at 30 sec, 90 sec, 120 sec, 180 sec, and 300 sec. Each data point below shows 2-second current mean and standard deviation; slope of end currents as a function of concentration also is show (FIGS. 50-53).

Example 29: Whole Virus Detection of Inactivated Coronavirus Detected Electrochemically Via Lateral Flow Based Sandwich Assay Targeting Both Spike and Membrane Viral Proteins A solution containing 1 mg/mL of anti-SARS-CoV-2 membrane(matrix) protein antibody conjugated to glucose oxidase, 1 mg/mL biotinylated anti-SARS-CoV-2 S1 spike protein antibody, and SARS-CoV-2 virus at 12900 TCID50/mL, 1290 TCID50/mL, 129 TCID50/mL or 0 TCID50/mL was prepared in assay buffer in a tube. The final viral concentrations were formulated to mimic addition of a biological sample (1290 TCID50/mL, 129 TCID50/mL, 12.9 TCID50/mL or 0 TCID50/mL), which may be diluted in buffer, to a vessel containing reagents and a capture and/or anchoring material. The mixed solution containing 1290 TCID50/mL, 129 TCID50/mL, 12.9 TCID50/mL or 0 TCID50/mL SARS-CoV-2 viral was transferred onto a blank test membrane (blocked or unblocked but not functionalized with any capture reagents) from above and subsequently washed with buffer, which was collected via a wicking material. In this example the membrane sat atop the electrode with the wicking pad at one end of the test membrane, the solution flows laterally. 50 μL of 500 mM glucose (pH 7.4) was then deposited on the membrane region atop the electrode to measure concentration of target present and captured. Chronoamperometry was run for 300 sec, 1 sec after substrate addition, by application of a −0.2 V (vs Ag/AgCl) potential. Results show detection of SARS-CoV-2 virus via this method (FIG. 54-61).

Example 30: Detection of IgG

A solution containing 1 μg/mL anti-IgG antibody bound to alkaline phosphatase, 1 g/mL biotinylated anti-IgG antibody, and IgG protein at 100 ng/ml, 50 ng/mL or 10 ng/ml will be prepared in assay buffer. The IgG was produced in response to a COVID infection. A region of streptavidin-coated beads embedded in a lateral flow membrane sat atop an electrode. 100 ul of the test or control solution will be added to a lateral flow membrane. Solution flowed across the membrane. After 2 minutes, the membrane will be washed with 200 uL buffer, which will be collected via a wicking pad. 60 uL of 10 mM 4-aminophenyl phosphate/diethanolamine substrate (pH 9.8) will be then deposited on the membrane region atop the electrode to measure concentration of IgG captured in a sandwich configuration (FIG. 28). In one case, chronoamperometry will be run for 10 sec following 5 min substrate incubation. In another case, modified chronoamperometry will be run by repeated application of a 0.2 V (vs Ag) potential (measuring current over these 10 seconds) every 30 s after introduction of the substrate solution for a total duration of 310 sec. Both chronoamperometry runs will show detection of the IgG compared to a control solution containing no IgG.

Example 31: Limit of Detection

In the above examples to detect a protein, small molecules, or virus, the limit of detection (LoD) was defined as a value three standard deviations above the 0 ng/mL baseline (control assay with no analyte added). One can also define the LoD as a value of two standard deviations above the 0 ng/mL baseline. LoD's are also be calculated based on the standard deviation of the response (Sy) of the curve and the slope of the calibration curve (S) (e.g., LoD=3.3(S y/S)).

The invention claimed is:

1. A system for detecting at least one target analyte in a biological sample added to the system, comprising: (i) an assay comprising at least one capture agent and at least one detector agent capable of creating a detectable complex with the at least one target analyte, if present, in the presence of added substrate; and (ii) a detection device for detecting the detectable complex, wherein the detection device comprises an enzyme-based amperometric sensor comprising at least one electrode, wherein the detectable complex forms above the least one electrode or migrates within the system to become located above at least one electrode; wherein the system has a limit of detection of about 100 target analytes/mL or less.

2. The system of claim 1, wherein the detectable complex is detected within about 30 minutes or less.

3. The system of claim 1, wherein the detectable complex is detected within a time frame selected from within about 10 minutes or less, about 5 minutes or less, about 2 minutes or less or about 1 minute or less.

4. The system of claim 1, wherein the target analyte is a protein or peptide.

5. The system of claim 1, wherein the target analyte is a viral protein or peptide.

6. The system of claim 1, wherein the target analyte is a nucleocapsid (N) protein of a coronavirus.

7. The system of claim 1, wherein the target analyte is an epitope of an N protein of a coronavirus.

8. The system of claim 1, wherein the target analyte is the N protein of SARS-COV-2 or a variant thereof.

9. The system of claim 1, wherein the target analyte is an epitope of the N protein of SARS-COV-2 or a variant thereof.

10. The system of claim 1, wherein the system detects two or more target analytes in the biological sample.

11. The system of claim 1, wherein the system detects two or more viral species in the biological sample.

12. The system of claim 1, wherein the target analyte is a cytokine.

13. The system of claim 1, wherein the target analyte is an interleukin or interferon.

14. The system of claim 1, wherein the target analyte is a hormone.

15. The system of claim 1, wherein the target analyte is a small molecule.

16. The system of claim 1, wherein the system has a limit of detection of about 1 ng/ML or less.

17. The system of claim 1, wherein the system has a limit of detection of about 500 μg/mL or less.

18. The system of claim 1, wherein the system has a limit of detection of about 100 μg/mL or less.

19. The system of claim 1, wherein the system has a limit of detection selected from about 20, about 10, or about 5 target analytes/mL or less.

* * * * *